US006841665B2

(12) United States Patent
Yang et al.

(10) Patent No.: US 6,841,665 B2
(45) Date of Patent: Jan. 11, 2005

(54) METHOD FOR SYNTHESIZING 5β, 6β-EPOXIDES OF STEROIDS BY A HIGHLY β-SELECTIVE EPOXIDATION OF ΔΔ$^5$-UNSATURATED STEROIDS CATALYZED BY KETONES

(75) Inventors: Dan Yang, Hong Kong (HK); Guan-Sheng Jiao, College Station, TX (US)

(73) Assignee: The University of Hong Kong, Hong Kong (CN)

( * ) Notice: Subject to any disclaimer, the term of this patent is extended or adjusted under 35 U.S.C. 154(b) by 195 days.

(21) Appl. No.: 10/091,627

(22) Filed: Mar. 6, 2002

(65) Prior Publication Data

US 2003/0018188 A1 Jan. 23, 2003

Related U.S. Application Data

(63) Continuation-in-part of application No. 09/788,201, filed on Feb. 16, 2001, now abandoned.
(60) Provisional application No. 60/183,396, filed on Feb. 18, 2000.

(51) Int. Cl.$^7$ ............................................. C07J 71/00

(52) U.S. Cl. ........................................................ 540/80

(58) Field of Search ............................................ 540/80

(56) References Cited

U.S. PATENT DOCUMENTS

| 3,676,433 | A |   | 7/1972 | Parikh |         |
|-----------|---|---|--------|--------|---------|
| 4,613,463 | A |   | 9/1986 | Sacks  |         |
| 5,508,452 | A |   | 4/1996 | Roussel et al. | |
| 5,763,623 | A | * | 6/1998 | Yang et al. | ......... 549/267 |

OTHER PUBLICATIONS

Bovicelli et al., "Oxidation of Natural Targets by Dioxiranes. Oxyfunctionalization of Steroids." J. Org. Chem., vol. 57, pp. 2182–2184, 1992.*
Cicala et al., "Stereo- and Regioselectivities in the Epoxidation of Some Allylic alcohols by the Dioxirane Intermediate Generated in the Reaction of Potassium Caroate with Acetone." J. Org. Chem., vol. 47, pp. 2670–2673, 1982.*
Holland et al., "1,3 Acyl Migration to an Epoxide. Reversible Rearrangement of 5,6 beta–Epoxyepicholesteryl Acetate." J. Org. Chem., vol. 48, pp. 3134–3136, 1983.*
Yang et al., "Design of Efficient Ketone Catalysts for Epoxidation by Using the Field Effect." J. Org. Chem., vol. 63, pp. 8952–8956, 1998.*
Collins, D., et al., "6α– and 6β–Acetic Acid Derivatives of Cholest–4–en–3–one and Pregn–4–ene–3, 20–dione," Aust. J. Chem., vol. 29, pp. 2077–2085 (1976).
Kesavan, V., et al., "A Highly β–Stereoselective Catalytic Epoxidation of Δ5–Unstaturated Steriods with a Novel Ruthenium (II) Complex under Aerobic Conditions," J. Org. Chem., vol. 63, pp. 6999–7001 (1998).

Marchon, J., et al., "Stereospecific Epoxidation by Air of Cholest–5–ene Derivatives catalysed by a Ruthenium Porphyrin," J. Chem. Soc., Chem. Commun, pp. 298–299 (1988).
Marchon, J., et al., "A Convenient Systhesis of 5,6β–Epoxides of Some Cholesteryl Esters and Δ5–Ketosteroid Derivatives by Catalytic β–Stereoselective Epoxidation," Communications, pp. 389–391 (1989).
Marples, B., et al., "Dioxirane Mediated Steroidal Alkene Epoxidations and Oxygen Insertion into Carbon–Hydrogen Bonds," Tetrahedron Letters, vol. 32, No. 4, pp. 533–536 (1991).
Parish, E., et al., "A One–Step Synthesis of 6β–Hydroxy–Δ 4–3–Ketones. Novel Oxidation of Homoallyic Sterols with Permanganate Ion," J. Org. Chem., vol. 61, pp. 5665–5666 (1996).
Salvador, J., et al., "Oxidations with Potassium Permanganate–Metal Sulphates and Nitrates. β–Selective Epoxidation of 5Δ–Unsaturated Steroids," Tetrahedron Letters, vol. 37, No. 5, pp. 687–690 (1996).
Symala, M., et al., "A Novel and Highly β–Selective Epoxidation of Δ5–Unstaturated Steroids with Permanganate Ion," J. Org. Chem., vol. 57, pp. 1928–1930 (1992).
Yang D., et al., "Epoxidation of Olefins Using Methyl(trifluoromethyl)dioxirane Generated in Situ," J. Org. Chem., vol. 60, pp. 3887–3889 (1995).
Yang D., et al., "Novel Cyclic Ketones for Catalytic Oxidation Reactions," J. Org. Chem., vol. 63, pp. 9888–9894 (1998).
Yates, P., et al., "Studies of the Synthesis of 5–Hydroxy 6–Keto Steroids and Related 6–Keto Steroids," Can. J. Chem., vol. 65, pp. 2203–2216 (1987).
Yang, D., et al., "Highly β–Selective Epoxidation of Δ5–Unsaturated Steroids Catalyzed by Ketones," Chem. Eur. J., vol. 6, No. 19, pp. 3517–3521 (2000).
Yang X. et al., *Biochemistry*, 2000, vol. 39, pp. 4915–4923.
Yang, D., et al., "Diastereoselective Epoxidation of Cyclohexene Derivatives by Dioxiranes Generated in Situ. Importance of Steric and Field Effects," J. Org. Chem., vol. 64, pp. 1635–1639 (1999).

* cited by examiner

Primary Examiner—Barbara P. Badio
(74) Attorney, Agent, or Firm—Jones, Day

(57) ABSTRACT

A general, efficient, and environmentally friendly method is provided for producing mostly β-epoxides of Δ$^5$-unsaturated steroids using certain ketones as the catalyst along with an oxidizing agent, or by using certain dioxiranes. In another aspect of the invention, a method is provided for producing mostly 5β,6β-epoxides of steroids from Δ$^5$-unsaturated steroids having a substituent at the 3α-position by an epoxidation reaction using a ketone along with an oxidizing agent under conditions effective to generate epoxides, or using a dioxirane under conditions effective to generate epoxides. A whole range of Δ$^5$-unsaturated steroids, bearing different functional groups such as hydroxy, carbonyl, acetyl or ketal group as well as different side chains, were conveniently converted to the corresponding synthetically and biologically interesting 5β,6β-epoxides with excellent β-selectivities and high yields.

63 Claims, 35 Drawing Sheets

KETONES:

STEROIDS:

TABLE 1, ENTRY 4

AUTHENTIC SAMPLES OF 5a/5b

TABLE 1, ENTRY 1

TABLE 1, ENTRY 4

TABLE 1, ENTRY 5

AUTHENTIC SAMPLES OF 6a/6b

TABLE 1, ENTRY 5

TABLE 1, ENTRY 6

AUTHENTIC SAMPLES OF 7a/7b

TABLE 1, ENTRY 6

TABLE 1, ENTRY 7

TABLE 1, ENTRY 8

AUTHENTIC SAMPLES OF 9a/9b

TABLE 1, ENTRY 10

AUTHENTIC SAMPLES OF 10a/10b

TABLE 1, ENERY 10

11a    11b

TABLE 2, ENTRY 2

AUTHENTIC SAMPLES OF 11a/11b

TABLE 2, ENTRY 1

TABLE 2, ENTRY 4

12b

TABLE 2, ENTRY 5

TABLE 2, ENTRY 6

13b

TABLE 2, ENTRY 8

TABLE 2, ENTRY 8

TABLE 2, ENTRY 9

TABLE 2, ENTRY 10

14b
TABLE 2, ENTRY 11

AUTHENTIC SAMPLES OF 14a/14b

TABLE 2, ENTRY 11

TABLE 2, ENTRY 12

15b

TABLE 2, ENTRY 13

TABLE 2, ENTRY 14

TABLE 2, ENTRY 13

AUTHENTIC SAMPLES OF 16a/16b

TABLE 2, ENTRY 15

TABLE 2, ENTRY 16

TABLE 2, ENTRY 17

TABLE 2, ENTRY 19

TABLE 2, ENTRY 19

TABLE 2, ENTRY 19
(10 mmol Scale)

TABLE 2, ENTRY 20

TABLE 2, ENTRY 21

AUTHENTIC SAMPLES
OF 19a/19b

TABLE 2, ENTRY 21

20b
TABLE 2, ENTRY 23

AUTHENTIC SAMPLES OF 20a/20b

TABLE 2, ENTRY 23

TABLE 2, ENTRY 24

US 6,841,665 B2

METHOD FOR SYNTHESIZING 5β, 6β-EPOXIDES OF STEROIDS BY A HIGHLY β-SELECTIVE EPOXIDATION OF ΔΔ⁵-UNSATURATED STEROIDS CATALYZED BY KETONES

This application is a continuation-in-part of non-provisional application Ser. No. 09/788,201 filed Feb. 16, 2001 now abandoned, which claims the benefit under 35 U.S.C. 119(e) of U.S. Provisional Application Ser. No. 60/183,396 filed Feb. 18, 2000.

TECHNICAL FIELD

The present invention is directed to the field of synthesizing epoxides of steroids.

BACKGROUND OF THE INVENTION

Steroid epoxides are an important class of oxysterols (oxygenated derivatives of cholesterol) involved in the regulation of cell proliferation and cholesterol homeostasis. They are versatile intermediates for steroid synthesis and useful probes for biochemical studies of enzymes. Steroid epoxides are also useful intermediates for the preparation of other oxysterols. For example, α- and β-epoxides of cholesterol are auto-oxidation products of cholesterol in vivo, and both are cytotoxic and mutagenic. The isomeric α- and β-epoxides are hydrolysed by cholesterol 5,6-epoxide hydrolase to cholestane-3β,5α,6β-triol which has potent hypocholesterolemic activity. On the other hand, both epoxides inhibit the cholesterol 7α-hydroxylase which catalyzes the rate-determining step of bile acid synthesis. As 5α,6α-epoxides are readily available via epoxidation of Δ⁵-unsaturated steroids with peracids, there have been extensive studies on the biological actions of those epoxides and their derivatives. In contrast, much less is known about the 5β,6β-epoxides and their derivatives because they are difficult to obtain in high selectivity. More importantly, the 5β,6β-epoxy functionality is found in a number of naturally occurring steroids of antitumor activities, e.g., jaborosalactone A, withaferin A, and withanolide D.

Common organic oxidants such as 3-chloroperoxybenzoic acid (mCPBA) generally give α-epoxides as the major products for epoxidation of 3β-substituted Δ⁵-steroids and show poor selectivities for epoxidation of 3α-substituted Δ⁵-steroids except epi-cholesterol. This is because peracid epoxidation follows a concerted pathway via spiro transition states (α-TS and β-TS (TS=transition state); see FIG. 1). The β-TS suffers from steric interactions between the peracid and the C(10) angular methyl group for epoxidation of 3β-substituted Δ⁵-steroids, while both the β-TS and the α-TS encounter similar steric hindrance for epoxidation of 3α-substituted Δ⁵-steroids. Dioxiranes are new-generation reagents for oxidation under mild and neutral conditions. Unfortunately, poor selectivities were reported in epoxidation of 3β-substituted Δ⁵-steroids by either isolated or in situ generated dioxiranes. While dioxiranes also epoxidize olefins through a spiro TS, their steric environment is different from that of peracids. To minimize steric interactions, dioxiranes prefer to approach the C(5)=C(6) double bond of Δ⁵-steroids from the less-substituted side, i.e., away from the C(10)-angular methyl group and the C-ring of steroids (FIG. 1). Therefore, it is the potential steric interactions between the α-substituents of dioxiranes and the 3α and 4β substituents of steroids that determine the facial selectivity of epoxidation.

Yang et al., in U.S. Pat. No. 5,763,623 and in J. Org. Chem., 1998, vol. 63 pages 8952–8956, disclose the epoxidation of unfunctionalized olefins using various ketones. These references do not teach or suggest the epoxidation of Δ⁵-unsaturated steroids.

Cicala, G., et al., J. Org. Chem., 1982, vol. 47, pages 2670–2673, disclose the epoxidation of a Δ⁵-unsaturated steroid that is not a 3α-substituted Δ⁵-unsaturated steroid, and in which the ketone catalyst is acetone.

Marples, B. A., et al. Tetrahedron Lett., 1991, vol. 32, pages 533–536, disclose the epoxidation reactions of four Δ⁵-unsaturated steroids that are not 3ax-substituted Δ⁵-unsaturated steroids, and using a variety of ketones. In these reactions either no epoxide was observed, or the β/α-epoxide ratio was about 1:1.

Bovicelli, P., et al., J. Org. Chem., 1992, vol. 57, pages 2182–2184, disclose the epoxidation of a Δ⁵-unsaturated steroid that is not a 3α-substituted Δ⁵-unsaturated steroid, and using dimethyldioxirane. The β/α-epoxide ratio was about 3:1.

Boehlow, T. R., et al., Tetrahedron Lett., 1998, vol. 39, pages 1839–1842, disclose the epoxidation of a Δ⁵-unsaturated steroid that is not a 3α-substituted Δ⁵-unsaturated steroid, and using a variety of ketone catalysts.

Shi, Y., in PCT Publication No. WO 01/12616 A1, Feb. 22, 2001, discloses an epoxidation method combining an olefin substrate, a ketone catalyst, a nitrile compound, and hydrogen peroxide.

Shi, Y., in PCT Publication No. WO 98/15544, Apr. 16, 1998, discloses the use of a chiral ketal and an oxidizing agent with an olefin to generate an epoxide with high enantioselectricity.

SUMMARY OF THE INVENTION

In accordance with the invention, a method is provided for producing mostly 5β,6β-epoxides of Δ⁵-unsaturated steroids using certain ketones as the catalyst along with an oxidizing agent, or by using certain dioxiranes. In another aspect of the invention, a method is provided for producing mostly 5β,6β-epoxides of steroids from Δ⁵-unsaturated steroids having a substituent at the 3α-position by an epoxidation reaction using a ketone along with an oxidizing agent under conditions effective to generate epoxides, or using a dioxirane under conditions effective to generate epoxides.

A whole range of Δ⁵-unsaturated steroids, bearing different functional groups such as hydroxy, carbonyl, acetyl or ketal group, as well as different side chains, are converted to the corresponding synthetically and biologically interesting 5β,6β-epoxides with excellent β-selectivities and high yields.

DETAILED DESCRIPTION OF THE INVENTION

Figure 1:
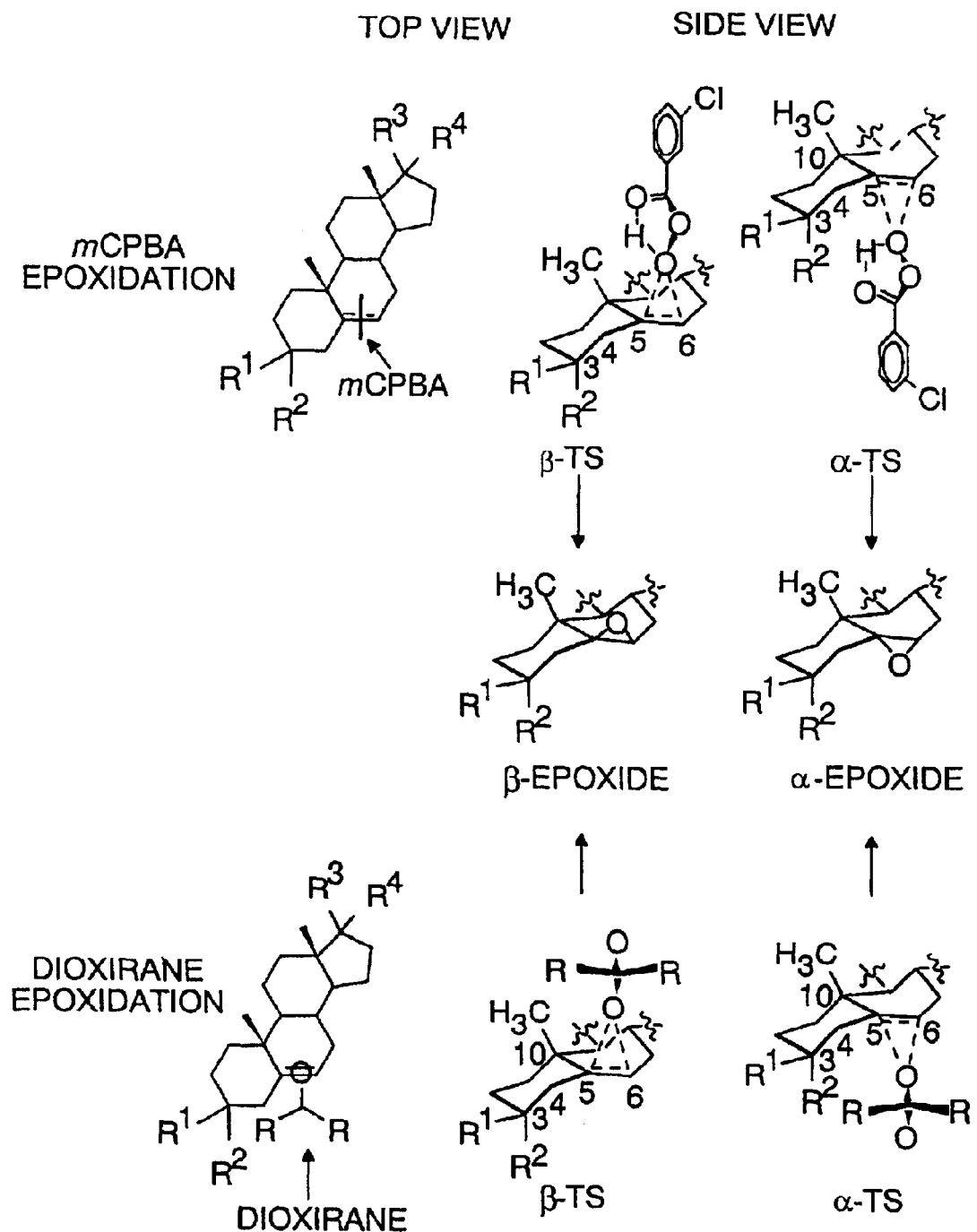
FIG. 1 is a diagrammatic representation of the general epoxidation reaction between Δ⁵-unsaturated steroids and mCPBA or dioxirane.

The present invention provides highly β-selective epoxidation of $\Delta^5$-unsaturated steroids catalyzed by ketones or mediated by dioxiranes. More specifically, the present invention demonstrates that high β-selectivity can be achieved by increasing the steric size of either the α-substituents of dioxiranes or the 3α substituents of $\Delta^5$-steroids. In some embodiments of the invention, the epoxidation reaction can provide said epoxides in at least about 5:1β/α-epoxide ratio.

In one aspect of the invention, a method of producing mostly 5β,6β-epoxides of steroids from $\Delta^5$-unsaturated steroids comprises an epoxidation reaction using a ketone and an oxidizing agent under conditions effective to generate epoxides, wherein the ketone is selected from compounds of generic formula I,

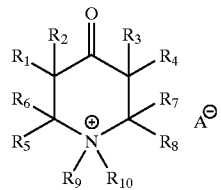

I in which $R_1$ or $R_4$ in formula (I) is selected from alkyl, halogenated alkyl, aryl, OR (where R=H, alkyl or aryl), OCOR (where R=H, alkyl or aryl), OCOOR (where R=alkyl or aryl), OCOOCH$_2$R (where R=aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_2$ or $R_3$ in formula (I) is selected from H, alkyl, halogenated alkyl, aryl, OR (where R=H, alkyl or aryl), OCOR (where R=H, alkyl or aryl), OCOOR (where R=alkyl or aryl), OCOOCH$_2$R (where R=aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_5$, $R_6$, $R_7$ or $R_8$ in formula (I) is selected from H, alkyl, halogenated alkyl, aryl, COOR (where R=H, alkyl or aryl), and CONR$_1$R$_2$ (where $R_1$ or $R_2$=H, alkyl or aryl);

$R_9$ or $R_{10}$ in formula (I) is selected from alkyl, halogenated alkyl, and aryl; and A in formula (I) is selected from halogen, OTf, BF$_4$, OAc, NO$_3$, BPh$_4$, PF$_6$, and SbF$_6$.

In another aspect of the invention, a method of producing mostly 5β,6β-epoxides of steroids from $\Delta^5$-unsaturated steroids having a substituent at the 3α-position comprises an epoxidation reaction using a ketone and an oxidizing agent under conditions effective to generate epoxides. The substituent at the 3α-position can be selected from OR (where R=H, alkyl or arly), O(CH$_2$)$_n$OR (where n=1, 2 or 3, R=H, alkyl or aryl), O(CH$_2$)$_m$SO$_n$R (where n=1, 2 or 3; n=0, 1 or 2; R=H, alkyl or aryl), OSiR$_1$R$_2$R$_3$ (where $R_1$, $R_2$ or $R_3$=alkyl or aryl), OSO$_n$R where n=0, 1 or 2; R=H, alkyl or aryl), OCO$_n$R (where n=1 or 2; R=H, alkyl or aryl), OCONR$_1$R$_2$ (where $R_1$ or $R_2$=H, alkyl or aryl), OPO$_n$R (where where n=2 or 3; R=alkyl or arly), NR$_1$R$_2$ (where $R_1$ or $R_2$=H, alkyl or aryl), NR$_1$CO$_n$R$_2$ (where n=1 or 2; $R_1$ or $R_2$=H, alkyl or aryl), NR$_1$CONR$_2$R$_3$ (where $R_1$, $R_2$ or $R_3$=H, alkyl or aryl), NR$_1$SO$_n$R$_2$ (where n=1 or 2; $R_1$=H, alkyl or aryl, $R_2$=alkyl or aryl), NPhth (Phth=phthaloyl group), $^+$NR$_1$R$_2$R$_3$ (where $R_1$, $R_2$, or $R_3$=H, alkyl or aryl), SiR$_1$R$_2$R$_3$ (where $R_1$, $R_2$, or $R_3$=H, alkyl or aryl), SO$_n$R (where n=0, 1 or 2; R=H, alkyl or aryl), SCO$_n$R (where n=1 or 2; R=H, alkyl or aryl), halogen, CN, NO$_2$, alkyl, aryl, COOR (where R=H, alkyl or aryl), and CONR$_1$R$_2$ (where $R_1$ or $R_2$=H, alkyl or arly).

Further in accordance with this aspect of the invention, the $\Delta^5$-unsaturated steroid having a substituent at the 3α-position can be selected from the group consisting of $\Delta^5$-unsaturated steroids having a ketal derivative of ketone group or a thioketal derivative of ketone group at the 3-position.

Further in accordance with this aspect of the invention, the ketone used in the epoxidation reaction can be selected from the group consisting of compounds of generic formula II, III, IV, and V wherein

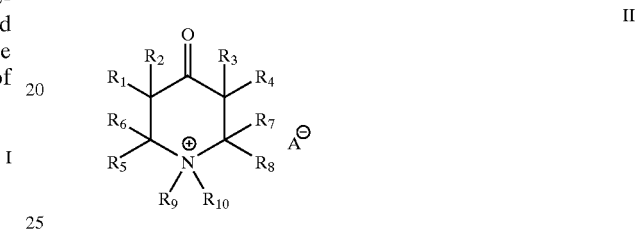

II $R_1$, $R_2$, $R_3$, or $R_4$ in formula (II) is selected from H, alkyl, halogenated alkyl, aryl, OR (where R=H, alkyl or aryl), OCOR (where R=H, alkyl or aryl), OCOOR (where R=alkyl or aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_5$, $R_6$, $R_7$, $R_8$, $R_9$ or $R_{10}$ in formula (II) is selected from H, alkyl, halogenated alkyl, aryl, COOR (where R=H, alkyl or aryl), and CONR$_1$R$_2$ (where $R_1$ or $R_2$=H, alkyl or aryl);

A in formula (iI) is selected from halogen, OTf, BF$_4$, OAc, NO$_3$, BPh$_4$, PF$_6$, and SbF$_6$;

III

X in formula (III) is selected from (CR$_1$R$_2$)$_n$ (where n=1, 2, 3, 4, or 5; $R_1$ or $R_2$=H, alkyl or aryl), O, S, SO, SO$_2$, and NR (where R=H, alkyl or aryl);

$R_{11}$, $R_{12}$, $R_{13}$, or $R_{14}$ in formula (III) is selected from H, alkyl, halogenated alkyl, aryl, OR (where R=H, alkyl or aryl), OCOR (where R=H, alkyl or aryl), OCOOR (where R=alkyl or aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_{15}$, $R_{16}$, $R_{17}$, or $R_{18}$ in formula (III) is selected from H, alkyl, halogenated alkyl, aryl, COOR (where R=H, alkyl or aryl), and CONR$_1$R$_2$ (where $R_1$ or $R_2$=H, alkyl or aryl);

IV $R_{19}$ or $R_{20}$ in formula (IV) is selected from alkyl, halogenated alkyl, aryl, CR$_1$R$_2$OCOR$_3$ (where $R_1$, $R_2$ or $R_3$=H, alkyl or aryl), CR$_1$R$_2$OCOOR$_3$ (where $R_1$ or $R_2$=H, alkyl or aryl; $R_3$=alkyl or aryl), $CR_1R_2NR_3COOR_4$ (where $R_1$, $R_2$ or $R_3$=H, alkyl or aryl, $R_4$=alkyl or aryl), $CR_1R_2NR_3COR_4$ (where $R_1$, $R_2$, $R_3$ or $R_4$=H, alkyl or aryl), and $CR_1R_2NR_3SO_2R_4$ (where $R_1$, $R_2$ or $R_3$=H, alkyl or aryl; $R_4$=alkyl or aryl); and

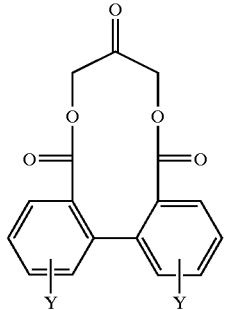

V

Y in formula (V) is selected from H, alkyl, halogenated alkyl, aryl, $NO_2$, CN, F, Cl, Br, I, COOR (where R=H or alkyl), OR (where R=H, alkyl or aryl), $OSO_2R$ (where R=H, alkyl or aryl), OSOR (where R=H, alkyl or aryl), OSR (where R=H, alkyl or aryl), $SO_2R$ (where R=H, alkyl or aryl), $SO_3R$ (where R=H, alkyl or aryl), SOON $R_1R_2$ (where $R_1$ or $R_2$=H, alkyl or aryl), $NR_1SOOR_2$ (where $R_1$=H, alkyl or aryl; $R_2$=alkyl or aryl), $NR_1SOR_2$ (where $R_1$=H, alkyl or aryl; $R_2$=alkyl or aryl), $CR_1R_2OR_3$ (where $R_1$, $R_2$ or $R_3$=H, alkyl or aryl), $CR_1(OR_2)_2$ (where $R_1$=H or alkyl; $R_2$=alkyl), $CF_3$, $CF_2CF_3$, OTf, OTs, OCOR (where R=H, alkyl or aryl), and $OSiR_1R_2R_3$ (where $R_1$, $R_2$ or $R_3$=alkyl or aryl).

In yet another aspect of the invention, a method of producing mostly 5,6β-epoxides of steroids from $\Delta^5$-unsaturated steroids comprises an epoxidation reaction using a dioxirane under conditions effective to generate epoxides, wherein said dioxirane is selected from compounds of generic formula VI,

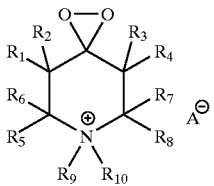

VI $R_1$ or $R_4$ in formula (VI) is selected from alkyl, halogenated alkyl, aryl, OR (where R=H, alkyl or aryl), OCOR (where R=H, alkyl or aryl), OCOOR (where R=alkyl or aryl), $OCOOCH_2R$ (where R=aryl), $OCONR_1R_2$ (where $R_1$ or $R_2$=H, alkyl or aryl), $OSiR_1R_2R_3$ (where $R_1$, $R_2$ or $R_3$=alkyl or aryl), and halogen;

$R_2$ or $R_3$ in formula (VI) is selected from H, alkyl, halogenated alkyl, aryl, OR (where R=H, alkyl or aryl), OCOR (where R=H, alkyl or aryl), OCOOR (where R=alkyl or aryl), $OCOOCH_2R$ (where R=aryl), $OCONR_1R_2$ (where $R_1$ or $R_2$=H, alkyl or aryl), $OSiR_1R_2R_3$ (where $R_1$, $R_2$ or $R_3$=alkyl or aryl), and halogen;

$R_5$, $R_6$, $R_7$ or $R_8$ in formula (VI) is selected from H, alkyl, halogenated alkyl, aryl, COOR (where R=H, alkyl or aryl), and $CONR_1R_2$ (where $R_1$ or $R_2$=H, alkyl or aryl);

$R_9$ or $R_{10}$ in formula (VI) is selected from alkyl, halogenated alkyl, and aryl; and A in formula (VI) is selected from halogen, OTf, $BF_4$, OAc, $NO_3$, BPh4, $PF_6$, and $SbF_6$.

The dioxirane can be generated in situ from a ketone and an oxidizing agent selected from potassium peroxomonosulfate, sodium hypochlorite, sodium perborate, hydrogen peroxide, and peracids, wherein said ketone is selected from compounds of generic formula I,

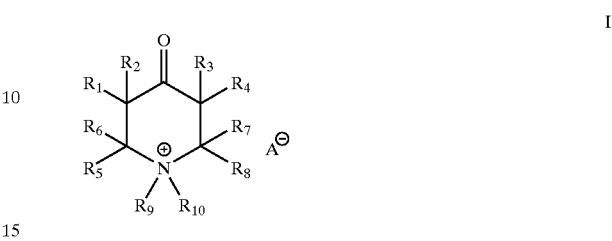

I $R_1$ or $R_4$ in formula (I) is selected from alkyl, halogenated alkyl, aryl, OR (where R=H, alkyl or aryl), OCOR (where R=H, alkyl or aryl), OCOOR (where R=alkyl or aryl), $OCOOCH_2R$ (where R=aryl), $OCONR_1R_2$ (where $R_1$ or $R_2$=H, alkyl or aryl), $OSiR_1R_2R_3$ (where $R_1$, $R_2$ or $R_3$=alkyl or aryl), and halogen;

$R_2$ or $R_3$ in formula (I) is selected from H, alkyl, halogenated alkyl, aryl, OR (where R=H, alkyl or aryl), OCOR (where R=H, alkyl or aryl), OCOOR (where R=alkyl or aryl), $OCOOCH_2R$ (where R=aryl), $OCONR_1R_2$ (where $R_1$ or $R_2$=H, alkyl or aryl), $OSiR_1R_2R_3$ (where $R_1$, $R_2$ or $R_3$=alkyl or aryl), and halogen;

$R_5$, $R_6$, $R_7$ or $R_8$ in formula (I) is selected from H, alkyl, halogenated alkyl, aryl, COOR (where R=H, alkyl or aryl), and $CONR_1R_2$ (where $R_1$ or $R_2$=H, alkyl or aryl);

$R_9$ or $R_{10}$ in formula (I) is selected from alkyl, halogenated alkyl, and aryl; and A in formula (I) is selected from halogen, OTf, $BF_4$, OAc, $NO_3$, $BPh_4$, $PF_6$, and $SbF_6$.

In yet another aspect of the invention, a method of producing mostly 5β,6β-epoxides of steroids from $\Delta^5$-unsaturated steroids having a substituent at the 3α-position comprises an epoxidation reaction using a dioxirane under conditions effective to generate epoxides. In accordance with this aspect of the invention, the substituent at the 3α-position can be selected from OR (where R=H, alkyl or aryl), $O(CH_2)_nOR$ (where n=1, 2 or 3; R=H, alkyl or aryl), $O(CH_2)_mSO_nR$ (where n=1, 2 or 3; n=0, 1 or 2; R=H, alkyl or aryl), $OSiR_1R_2R_3$ (where $R_1$, $R_2$ or $R_3$=alkyl or aryl), $OSO_nR$ (where n=0, 1 or 2; R=H, alkyl or aryl), $OCO_nR$ (where n=1 or 2; R=H, alkyl or aryl), $OCONR_1R_2$ (where $R_1$ or $R_2$=H, alkyl or aryl), $OPO_nR$ (where where n=2 or 3; R=alkyl or aryl), $NR_1R_2$ (where $R_1$ or $R_2$=H, alkyl or aryl), $NR_1CO_nR_2$ (where n=1 or 2; $R_1$ or $R_2$=H, alkyl or aryl), $NR_1CONR_2R_3$ (where $R_1$, $R_2$ or $R_3$=H, alkyl or aryl), $NR_1SO_nR_2$ (where n=1 or 2; $R_1$=H, alkyl or aryl, $R_2$=alkyl or aryl), NPhth (Phth=phthaloyl group), $^+NR_1R_2R_3$ (where $R_1$, $R_2$, or $R_3$=H, alkyl or aryl), $SiR_1R_2R_3$ (where $R_1$, $R_2$, or $R_3$=H, alkyl or aryl), $SO_nR$ (where n=0, 1 or 2; R=H, alkyl or aryl), $SCO_nR$ (where n=1 or 2; R=H, alkyl or aryl), halogen, CN, $NO_2$, alkyl, aryl, COOR (where R=H, alkyl or aryl), and $CONR_1R_2$ (where $R_1$ or $R_2$=H, alkyl or aryl).

Further in accordance with this aspect of the invention, the $\Delta^5$-unsaturated steroid having a substituent at the 3α-position can be selected from the group consisting of $\Delta^5$-unsaturated steroids having a ketal derivative of a ketone group or a thioketal derivative of a ketone group at the 3-position.

Further in accordance with this aspect of the invention, the dioxirane can be selected from the group consisting of compounds of generic formula VII, VIII, IX and X.

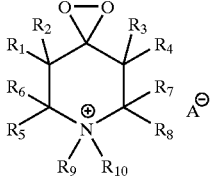

VII $R_1$, $R_2$, $R_3$, or $R_4$ in formula (VII) is selected from H, alkyl, halogenated alkyl, aryl, OR (where R=H, alkyl or aryl), OCOR (where R=H, alkyl or aryl), OCOOR (where R=alkyl or aryl), OCCOOCH$_2$R (where R=aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_5$, $R_6$, $R_7$, $R_8$, $R_9$ or $R_{10}$, in formula (VII) is selected from H, alkyl, halogenated alkyl, aryl, COOR (where R=H, alkyl or aryl), and CONR$_1$R$_2$ (where $R_1$ or $R_2$=H, alkyl or aryl);

A in formula (VII) is selected from halogen, OTf, BF$_4$, OAc, NO$_3$, BPh$_4$, PF$_6$, and SbF$_6$;

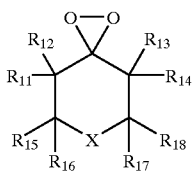

VIII

X in formula (VIII) is selected from (CR$_1$R$_2$)$_n$, (where n=1, 2, 3, 4, or 5; $R_1$ or $R_2$=H, alkyl or aryl), O, S, SO, SO$_2$, and NR (where R=H, alkyl or aryl);

$R_{11}$, $R_{12}$, $R_{13}$, or $R_{14}$ in formula (VIII) is selected from H, alkyl, halogenated alkyl, aryl, OR (where R=H, alkyl or aryl), OCOR (where R=H, alkyl or aryl), OCOOR (where R=alkyl or aryl), OCOOCH$_2$R (where R=aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_{15}$, $R_{16}$, $R_{17}$, or $R_{18}$ in formula (VIII) is selected from H, alkyl, halogenated alkyl, aryl, COOR (where R=H, alkyl or aryl), and CONR$_1$R$_2$ (where $R_1$ or $R_2$=H, alkyl or aryl);

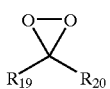

IX $R_{19}$ or $R_{20}$ in formula (IX) is selected from alkyl, halogenated alkyl, aryl, CR$_1$R$_2$OCOR$_3$ (where $R_1$, $R_2$ or $R_3$=H, alkyl or aryl), CR$_1$R$_2$OCOOR$_3$ (where $R_1$ or $R_2$=H, alkyl or aryl; $R_3$=alkyl or aryl), CR$_1$R$_2$NR$_3$COOR$_4$ (where $R_1$, $R_2$ or $R_3$=H, alkyl or aryl, $R_4$=alkyl or aryl), CR$_1$R$_2$NR$_3$COR$_4$ (where $R_1$, $R_2$, $R_3$ or $R_4$=H, alkyl or aryl), CR$_1$R$_2$NR$_3$SO$_2$R$_4$ (where $R_1$, $R_2$ or $R_3$=H, alkyl or aryl; $R_4$=alkyl or aryl); and

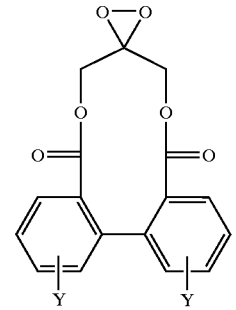

X

Y in formula (X) is selected from H, alkyl, halogenated alkyl, aryl, NO$_2$, CN, F, Cl, Br, I, COOR (where R=H or alkyl), OR (where R=H, alkyl or aryl), OSO$_2$R (where R=H, alkyl or aryl), OSOR (where R=H, alkyl or aryl), OSR (where R=H, alkyl or aryl), SO$_2$R (where R=H, alkyl or aryl), SO$_3$R (where R=H, alkyl or aryl), SOON R$_1$R$_2$ (where $R_1$ or $R_2$=H, alkyl or aryl), NR$_1$SOOR$_2$ (where $R_1$=H, alkyl or aryl; $R_2$=alkyl or aryl), NR$_1$SOR$_2$ (where $R_1$=H, alkyl or aryl; $R_2$=alkyl or aryl), CR$_1$R$_2$OR$_3$ (where $R_1$, $R_2$ or $R_3$=H, alkyl or aryl), CR$_1$(OR$_2$)$_2$ (where $R_1$=H or alkyl; $R_2$=alkyl), CF$_3$, CF$_2$CF$_3$, OTf, OTs, OCOR (where R=H, alkyl or aryl), and OSiR$_1$R$_2$R$_3$ (where $R_1$, $R_2$ or $R_3$=alkyl or aryl).

The dioxirane can be generated in situ from a ketone and an oxidizing agent selected from potassium peroxomonosulfate, sodium hypochlorite, sodium perborate, hydrogen peroxide, and peracids. In such embodiments of the invention, the ketone can be selected from the group consisting of compounds of generic formula II, III, IV, and V,

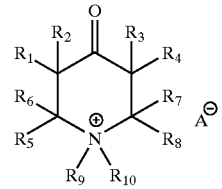

II $R_1$, $R_2$, $R_3$, or $R_4$ in formula (II) is selected from H, alkyl, halogenated alkyl, aryl, OR (where R=H, alkyl or aryl), OCOR (where R=H, alkyl or aryl), OCOOR (where R=alkyl or aryl), OCOOCH$_2$R (where R=aryl), OCONR$_1$R$_2$ (where $R_1$ or $R_2$=H, alkyl or aryl), OSiR$_1$R$_2$R$_3$ (where $R_1$, $R_2$ or $R_3$=alkyl or aryl), and halogen;

$R_5$, $R_6$, $R_7$, $R_8$, $R_9$ or $R_{10}$ in formula (II) is selected from H, alkyl, halogenated alkyl, aryl, COOR (where R=H, alkyl or aryl), and CONR$_1$R$_2$ (where $R_1$ or $R_2$=H, alkyl or aryl);

A in formula (II) is selected from halogen, OTf, BF$_4$, OAc, NO$_3$, BPh$_4$, PF$_6$, and SbF$_6$;

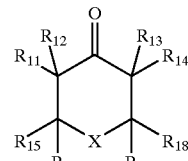

III

X in formula (III) is selected from $(CR_1R_2)_n$ (where n=1, 2, 3, 4, or 5; $R_1$ or $R_2$=H, alkyl or aryl), O, S, SO, $SO_2$, and NR (where R=H, alkyl or aryl);

$R_{11}$, $R_{12}$, $R_{13}$, or $R_{14}$ in formula (III) is selected from H, alkyl, halogenated alkyl, aryl, OR (where R=H, alkyl or aryl), OCOR (where R=H, alkyl or aryl), OCOOR (where R=alkyl or aryl), $OCOOCH_2R$ (where R=aryl), $OCONR_1R_2$ (where $R_1$ or $R_2$=H, alkyl or aryl), $OSiR_1R_2R_3$ (where $R_1$, $R_2$ or $R_3$=alkyl or aryl), and halogen;

$R_{15}$, $R_{16}$, $R_{17}$, or $R_{18}$ in formula (III) is selected from H, alkyl, halogenated alkyl, aryl, COOR (where R=H, alkyl or aryl), and $CONR_1R_2$ (where $R_1$ or $R_2$=H, alkyl or aryl);

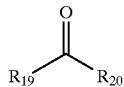

IV $R_{19}$ or $R_{20}$ in formula (IV) is selected from alkyl, halogenated alkyl, aryl, $CR_1R_2OCOR_3$ (where $R_1$, $R_2$ or $R_3$=H, alkyl or aryl), $CR_1R_2OCOOR_3$ (where $R_1$ or $R_2$=H, alkyl or aryl; $R_3$=alkyl or aryl), $CR_1R_2NR_3COOR_4$ (where $R_1$, $R_2$ or $R_3$=H, alkyl or aryl, $R_4$=alkyl or aryl), $CR_1R_2NR_3COR_4$ (where $R_1$, $R_2$, $R_3$ or $R_4$=H, alkyl or atyl), $CR_1R_2NR_3SO_2R_4$ (where $R_1$, $R_2$ or $R_3$=H, alkyl or aryl; $R_4$=alkyl or aryl); and

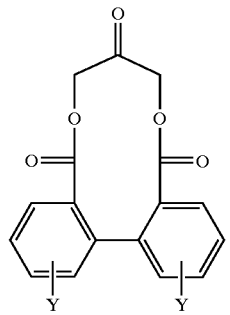

V

Y in formula (V) is selected from H, alkyl, halogenated alkyl, aryl, $NO_2$, CN, F, Cl, Br, I, COOR (where R=H or alkyl), OR (where R=H, alkyl or aryl), $OSO_2R$ (where R=H, alkyl or aryl), OSOR (where R=H, alkyl or aryl), OSR (where R=H, alkyl or aryl), $SO_2R$ (where R=H, alkyl or aryl), $SO_3R$ (where R=H, alkyl or aryl), $SOON R_1R_2$ (where $R_1$ or $R_2$=H, alkyl or aryl), $NR_1SOOR_2$ (where $R_1$=H, alkyl or aryl; $R_2$=alkyl or aryl), $NR_1SOR_2$ (where $R_1$=H, alkyl or aryl; $R_2$=alkyl or aryl), $CR_1R_2OR_3$ (where $R_1$, $R_2$ or $R_3$=H, alkyl or aryl), $CR_1(OR_2)_2$ (where $R_1$=H or alkyl; $R_2$=alkyl), $CF_3$, $CF_2CF_3$, OTf, OTs, OCOR (where R=H, alkyl or aryl), and $OSiR_1R_2R_3$ (where $R_1$, $R_2$ or $R_3$=alkyl or aryl).

Epoxidation reactions in accordance with the invention and using dioxiranes can be carried out in a solvent selected from acetonitrile, dimethoxymethane, acetone, dioxane, dimethoxyethane, tetrahydrofuran, dichloromethane, chloroform, benzene, toluene, diethylether, water and mixtures thereof.

In accordance with one embodiment of the invention herein, a method of producing mostly 5β,6β-epoxides of steroids comprises epoxidation reactions of $\Delta^5$-unsaturated steroids of generic formula XI catalyzed by ketones of generic formula XII, wherein

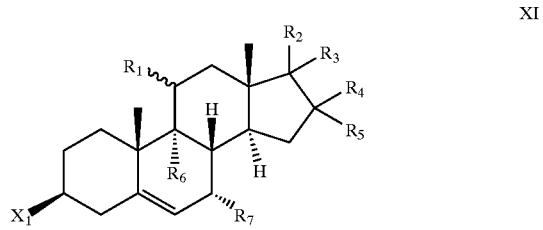

XI $X_1$ in formula (XI) is selected from H, OR (where R=H or alkyl), $OCH_2OCH_3$, OCOR (where R=alkyl or aryl), $OSiR_1'R_2'R_3'$ (where $R_1'$, $R_2'$ or $R_3'$=alkyl or aryl), halogen, CN, alkyl, aryl, and COOR (where R=H, alkyl or aryl);

$R_1$ in formula (XI) is selected from H, OR (where R=H or alkyl), OCOR (where R=alkyl or aryl), $OCH_2OCH_3$, halogen, $CF_3$, and $CF_2CF_3$;

$R_2$ and $R_3$ in formula (XI) are each selected from the group consisting of H, alkyl, aryl, halogen, OR (where R=H or alkyl), OCOR (where R=alkyl or aryl), $OSiR_1'R_2'R_3'$ (where $R_1'$, $R_2'$ or $R_3'$=alkyl or aryl), COR (where R=alkyl), $COCH_2OR$ (where R=H or alkyl), $COCH_2OCOR$ (where R=alkyl or aryl), $COCH_2F$, COOR (where R=H or alkyl), $C(OCH_2CH_2O)R$ (where R=alkyl), $C(OCH_2CH_2)CH_2OR$ (where R=H or alkyl), $C(OCH_2CH_2O)CH_2OCOR$ (where R=alkyl or aryl), and $C(OCH_2CH_2O)CH_2F$; or, are selected from the group consisting of O, $OCH_2CH_2O$, and $OCH_2CH_2CH_2O$;

$R_4$ in formula (XI) is selected from H, $C_1$–$C_4$ alkyl, halogen, OR (where R=H or alkyl), OCOR (where R=alkyl or aryl), and $OSiR_1'R_2'R_3'$ (where $R_1'$, $R_2'$ or $R_3'$=alkyl or aryl);

$R_5$ in formula (XI) is selected from H, $C_1$–$C_4$ alkyl, halogen, OR (where R=H or alkyl), OCOR (where R=alkyl or aryl), and $OSiR_1'R_2'R_3'$ (where $R_1'$, $R_2'$ or $R_3'$=alkyl or aryl);

$R_6$ in formula (XI) is selected from H, halogen, OR (where R=H or alkyl), and OCOR (where R=alkyl or aryl);

$R_7$ in formula (XI) is selected from H, halogen, OR (where R=H or alkyl), and OCOR (where R=alkyl or aryl);

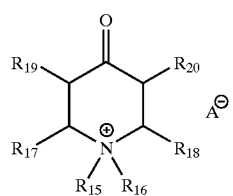

XII $R_{15}$ and $R_{16}$ in formula (XII) are each selected from alkyl and aryl;

$R_{17}$ and $R_{18}$ in formula (XII) are each selected from H, alkyl, aryl, COOR (where R=H, alkyl or aryl), and $CONR_1R_2$ (where $R_1$ or $R_2$=H, alkyl or aryl);

$R_{19}$ and $R_{20}$ in formula (XII) are each selected from $C_1$–$C_4$ alkyl, halogenated alkyl, and halogen; and A in formula (XII) is selected from OTf, $BF_4$, OAc, $NO_3$, $BPh_4$, $PF_6$, and $SbF_6$.

In another embodiment of the instant invention, a method of producing mostly 5β,6β-epoxides of steroids comprises epoxidation reactions of Δ⁵-unsaturated steroids of generic formula XIII catalyzed by ketones of generic formula XIV, XV, XVI, and XVII, wherein

XIII

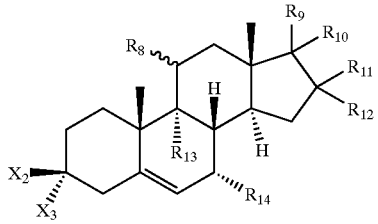

$X_2$ in formula (XIII) is selected from the group consisting of H, OR (where R=H or alkyl), $OCH_2OCH_3$, OCOR (where R=alkyl or aryl), $OSiR_1'R_2'R_3'$ (where $R_1'$, $R_2'$ or $R_3'$=alkyl or aryl), halogen, CN, alkyl, aryl, and COOR (where R=H, alkyl or aryl), and, $X_3$ in formula (XIII) is selected from the group consisting of OR (where R=H or alkyl), $OCH_2OCH_3$, OCOR (where R=alkyl or aryl), $OSiR_1'R_2'R_3'$ (where $R_1'$, $R_2'$ or $R_3'$=alkyl or aryl), halogen, CN, $NO_2$, alkyl, and aryl; or, $X_2$ and $X_3$ in formula (XIII) are selected from the group consisting of O, $OCH_2CH_2O$, and $OCH_2CH_2CH_2O$;

$R_8$ in formula (XIII) is selected from H, OR (where R=H or alkyl), OCOR (where R=alkyl or aryl), $OCH_2OCH_3$, halogen, $CF_3$, and $CF_2CF_3$;

$R_9$ and $R_{10}$ in formula (XIII) are each selected from the group consisting of H, alkyl, aryl, halogen, OR (where R=H or alkyl), OCOR (where R=alkyl or aryl), $OSiR_1'R_2'R_3'$ (where $R_1'$, $R_2'$ or $R_3'$=alkyl or aryl), COR (where R=alkyl), $COCH_2OR$ (where R=H or alkyl), $COCH_2OCOR$ (where R=alkyl or aryl), $COCH_2F$, COOR (where R=H or alkyl), $C(OCH_2CH_2O)R$ (where R=alkyl), $C(OCH_2CH_2O)CH_2OR$ (where R=H or alkyl), $C(OCH_2CH_2O)CH_2OCOR$ (where R=alkyl or aryl), and $C(OCH_2CH_2O)CH_2F$; or $R_9$ and $R_{10}$ in formula (XIII) are selected from the group consisting of O, $OCH_2CH_2O$, and $OCH_2CH_2CH_2O$;

$R_{11}$ and $R_{12}$ in formula (XIII) are each selected from the group consisting of H, $C_1$-$C_4$ alkyl halogen, OR (where R=H or alkyl), OCOR (where R=alkyl or aryl), and $OSiR_1'R_2'R_3'$ (where $R_1'$, $R_2'$ or $R_3'$=alkyl or aryl);

$R_{13}$ and $R_{14}$ in formula (XIII) are each selected from the group consisting of H, halogen, OR (where R=H or alkyl), and OCOR (where R=alkyl or aryl);

XIV

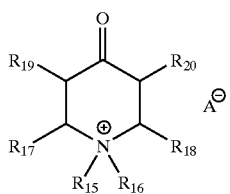

$R_{15}$ or $R_{16}$ in formula (XIV) is selected from alkyl and aryl;

$R_{17}$ or $R_{18}$ in formula (XIV) is selected from H, alkyl, aryl, COOR (where R=H, alkyl or aryl), and $CONR_1R_2$ (where $R_1$ or $R_2$=H, alkyl or aryl);

$R_{19}$ or $R_{20}$ in formula (XIV) is selected from H, $C_1$-$C_4$ alkyl, halogenated alkyl, and halogen; and A in formula (XIV) is selected from OTf, $BF_4$, OAc, $NO_3$, $BPh_4$, $PF_6$, and $SbF_6$;

XV

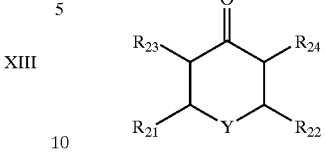

Y in formula (XV) is selected from $CH_2$, O, S, SO, $SO_2$, and NR (where R=H or alkyl);

$R_{21}$ or $R_{22}$ in formula (XV) is selected from H, alkyl, aryl, COOR (where R=H, alkyl or aryl), and $CONR_1R_2$ (where $R_1$ or $R_2$=H, alkyl or aryl);

$R_{23}$ or $R_{24}$ in formula (XV) is selected from H, halogen, $C_1$-$C_4$ alkyl, halogenated alkyl, and OCOR (where R=alkyl or aryl);

XVI

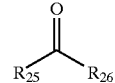

$R_{25}$ or $R_{26}$ in formula (XVI) is selected from $C_1$-$C_4$ alkyl, halogenated alkyl, $CH_2OCOR$ (where R=alkyl or aryl); and

XVII

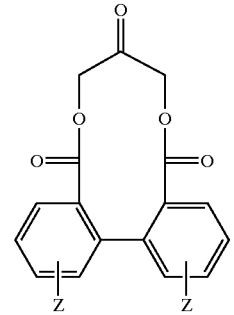

Z in formula (XVII) is selected from H, $C_1$-$C_4$ alkyl, aryl, $NO_2$, CN, F, Cl, Br, I, COOR (where R=alkyl), $CH_2OR$ (where R=H or alkyl), $CH(OR)_2$ (where R=alkyl), $CF_3$, $CF_2CF_3$, OTf, OTs, OCOR (where R=alkyl or aryl), and $OSiR_1'R_2'R_3'$ (where $R_1'$, $R_2'$ or $R_3'$=alkyl or In each of the disclosed embodiments, $C_1$-$C_4$ alkyl can be selected from the group consisting of methyl, ethyl, normal-propyl, iso-propyl, normal-butyl, iso-butyl, sec-butyl, and tert-butyl; and said aryl can be selected from the group consisting of phenyl, substituted phenyl, naphthyl, and substituted naphthyl groups. The epoxidation reactions can be carried out in a homoogeneous solvent system selected from the group consisting of dimethoxymethane-acetonitrile-water, acetonitrile-water, acetone-water, dioxane-water, dimethoxyethane-water, and tetrahydrofuran-water, and mixtures thereof. Alternatively, the epoxidation reactions can be carried out in a biphasic solvent system selected from the group consisting of dichloromethane-water, chloroform-water, benzene-water, toluene-water, dimethoxymethane-water, or diethylether-water and mixtures thereof.

Suitable oxidation agents for the epoxidation reactions of the instant invention include potassium peroxomonosulfate, sodium hypochlorite, sodium perborate, hydrogen peroxide, and peracids.

The epoxidation reactions of the instant invention catalyzed by a ketone can be carried out at a temperature within the range from about −10° C. to about 40° C. Direct dioxirane epoxidation reactions of the instant invention can be carried out at a temperature within the range of from about −40° C. to about 40° C. Some epoxidation reactions of the instant invention can be carried out at about room temperature.

The epoxidation reactions of the instant invention can be carried out at a pH within the range from about 7.0 to about 12.0. Some such epoxidation reactions can be carried out at a pH within the range from about 7.0 to about 7.5. The pH can be controlled by using a pH-stat machine such as is known in the art, or a buffer. Suitable buffers include solutions of sodium bicarbonate, sodium carbonate, sodium borate, sodium hydrogenphosphate, sodium dihydrogenphosphate, sodium hydroxide, potassium hydrogenphosphate, potassium dihydrogenphosphate, potassium bicarbonate, potassium carbonate and potassium hydroxide.

Figure 2:
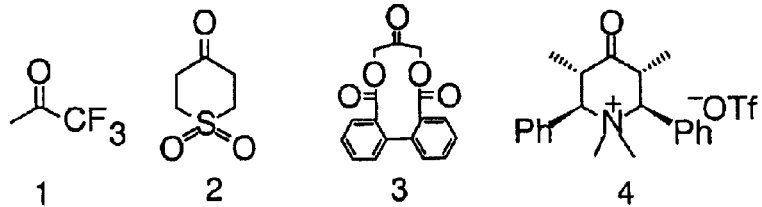
FIG. 2 is a listing of chemical structures corresponding to ketones 1–4 and steroids 5–20.
Figure 2:
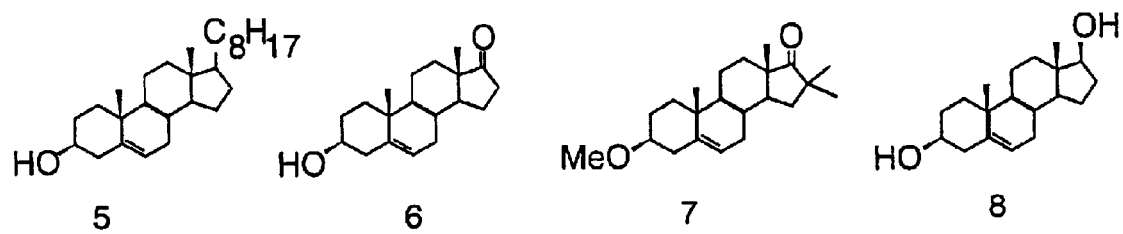
Figure 2:
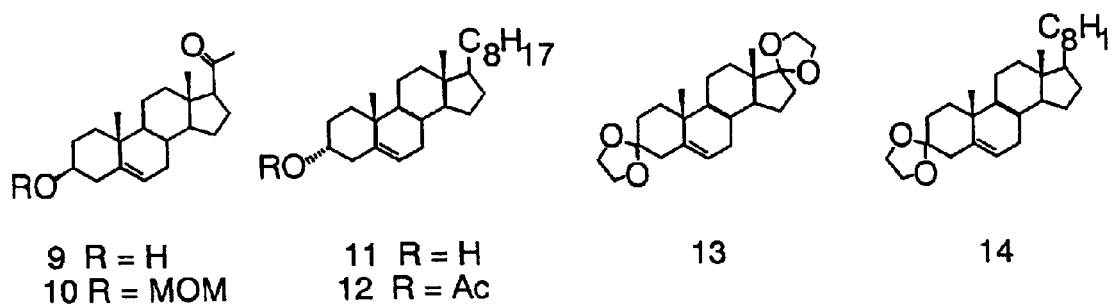
Figure 2:
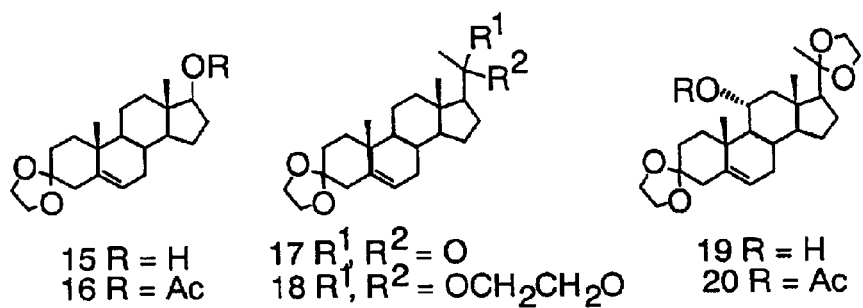
Figure 3:
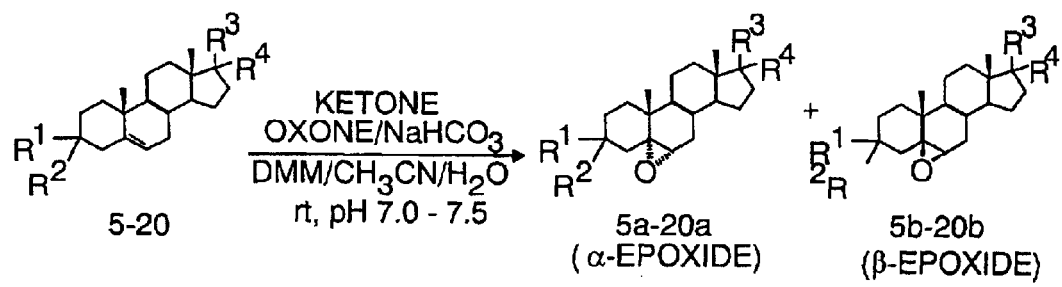
FIG. 3 is a diagrammatic representation of the epoxidation reaction of the present invention.

We first examined four efficient ketone catalysts 1–4 for the in situ epoxidation of cholesterol 5 (FIG. 2). A modified homogeneous solvent system (a mixture of DMM/CH$_3$CN/H$_2$O in a 3:1:2 ratio) was used to increase the solubility of steroid substrates (FIG. 3). The results are summarized in Table 1. The ratio of β/α-epoxides was determined by integration of C(6) proton signals in the $^1$H NMR spectra of the crude residues (δ3.00–3.15 ppm for β-epoxides and 67 2.75–2.95 ppm for α-epoxides). While ketones 1–3 exhibited poor β-selectivities (β/α epoxide ratio ca. 1:1; entries 1–3), ketone 4 with the most bulky α-substituent gave the best β-selectivity (β/α epoxide ratio 15.1:1; entry 4). A variety of 3β-substituted Δ$^5$-steroids 6–10 (FIG. 2) were then subjected to the in situ epoxidation conditions with 20–30 mol % of ketone 4. The results revealed that ketone 4 generally gave high β-selectivities (β/α epoxide ratio >8.5:1) and high yields (entries 4–10). It is interesting to note that Δ$^5$-steroids with a free C3-OH group were directly converted to their 5β,6β-epoxides with high selectivity and yields (entries 4, 5, and 7–9). (Note: The free 3-OH group of Δ$^5$-unsaturated steroids is not compatible with some metal-based oxidants in the epoxidation reactions.) Meanwhile, a wide range of functional groups such as hydroxyl, methoxyl, methoxymethyl ether, and carbonyl group were well tolerated under the mild and neutral reaction conditions (room temperature, pH 7–7.5).

Epoxidation reactions of 3α-substituted Δ$^5$-steroids 11–20 were also carried out with ketone catalysts 1–4 (FIG. 2) and the ketone catalyst acetone. For epicholesterol 11 with a 3α-OH group, the epoxidation reactions catalyzed by ketones 1 and 4 gave much higher selectivities than those by ketones 2 and 3 (Table 2; entries 1–4) and acetone (see Table 3). This is because ketones 1 and 4 have larger α-substituents. For substrates with 3α-substituents larger than the OH group (12–20), the in situ epoxidation catalyzed by ketones 1–4 and acetone produced almost single 5β,6β-isomers (Table 2, β/α ratio>49:1, entries 5–24; Table 3). Substrates with 3-ketal group are of particular interest since highly α-selective epoxidation with trifluoroperacetic acid has been reported for this class of Δ$^5$-steroids. Epoxidation of substrates 13–20 with mCPBA gave ca. 1:1 ratio of β/α-epoxides. The epoxidation reactions catalyzed by ketone 2 were highly efficient as only 5 mol % of the catalyst was needed even on a preparative scale. For example, a multi-gram scale (10 mmol) epoxidation of substrate 18 catalyzed by ketone 2 (5 mol %) provided almost a single β-epoxide (β/α-epoxide ratio>99:1) in 88% yield. These results clearly demonstrate the power of ketone-catalyzed epoxidation method.

In summary, we have developed a general, efficient and environmentally friendly method for highly β-selective epoxidation of Δ$^5$-unsaturated steroids. With this method in hand, a library of 5β,6β-epoxides and their derivatives can be readily constructed and then screened for potential ligands that bind to orphan nuclear receptors. This is crucial for elucidating the biological functions of those receptors as well as for drug discovery.

General Experimental

Figure 4:
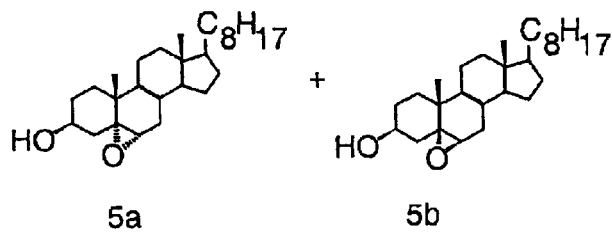
FIGS. 4–70 are ¹H NMR spectra of 5,β,6β-epoxides of steroids and 5α,6α-epoxides of steroids including those epoxides of steroids synthesized as products by the method of the present invention and purified epoxides of steroids used as comparative control standards (referred to as "authentic samples").
Figure 4:
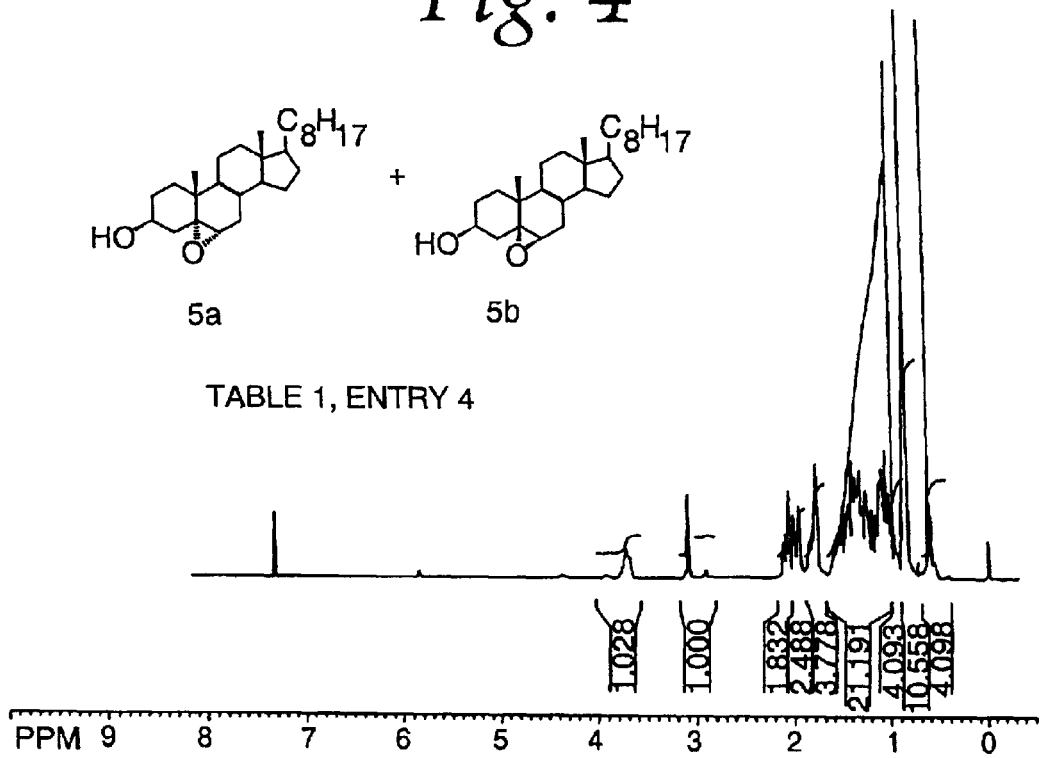
Figure 5:
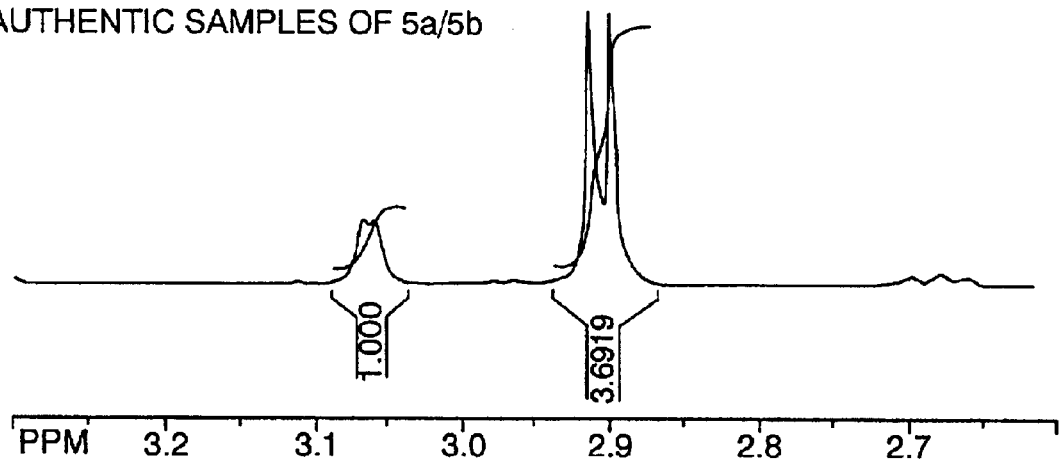
Figure 6:
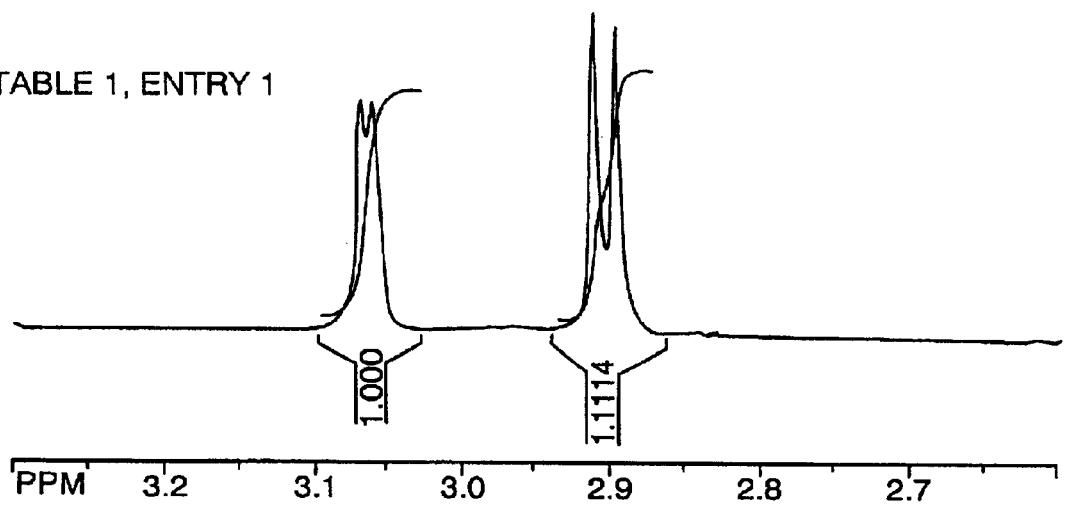
Figure 7:
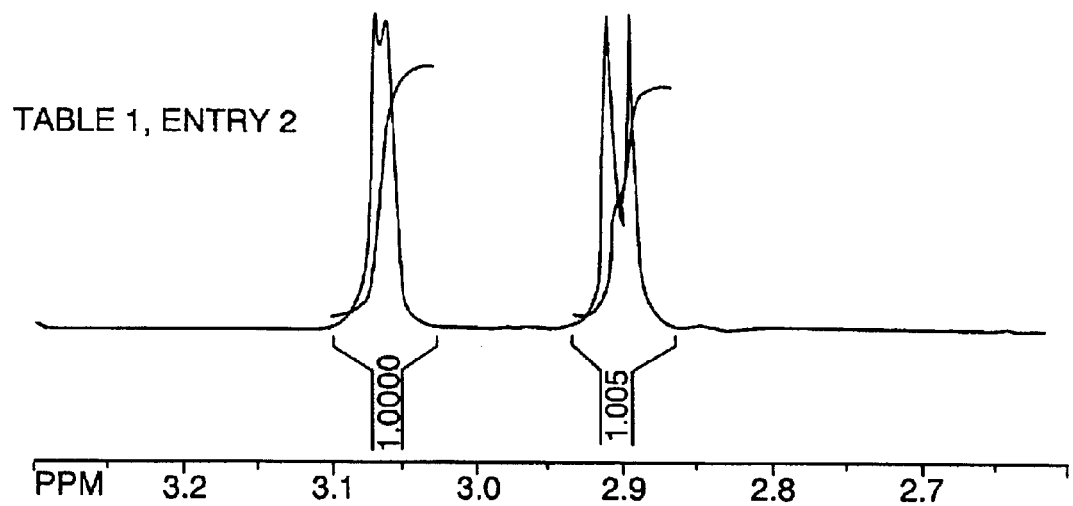
Figure 8:
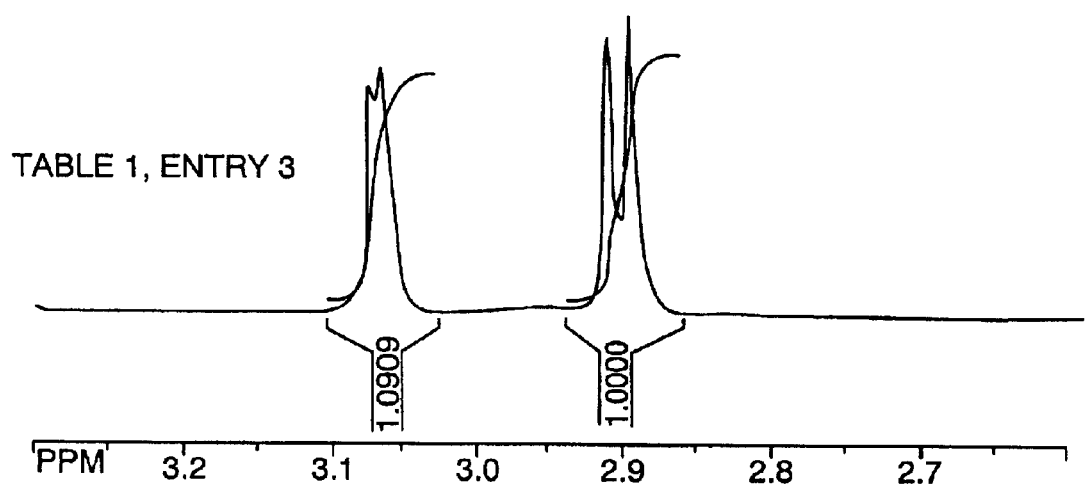
Figure 9:
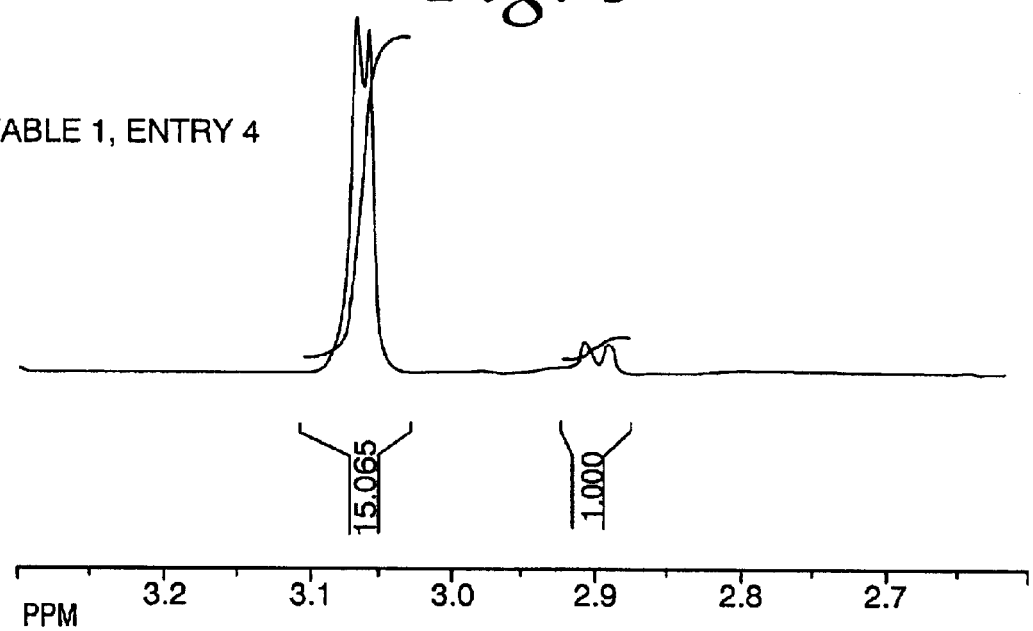
Figure 10:
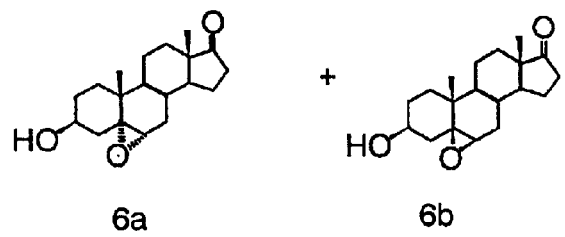
Figure 10:
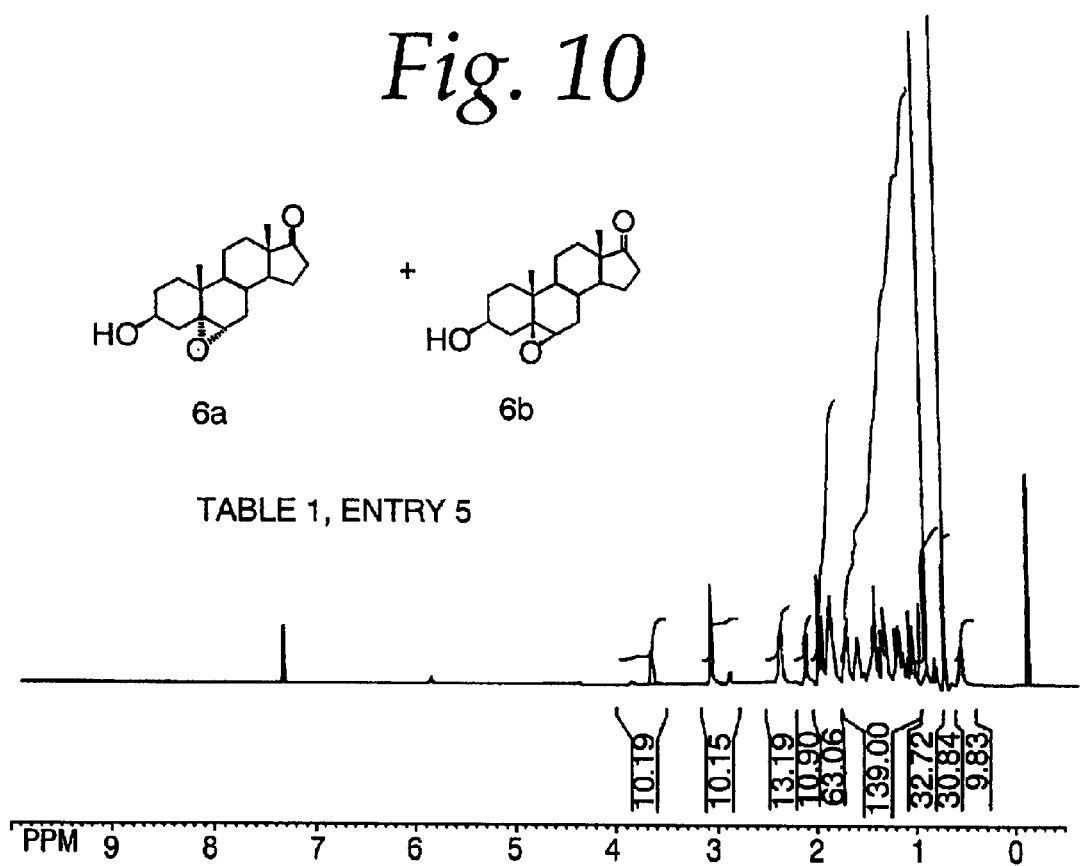
Figure 11:
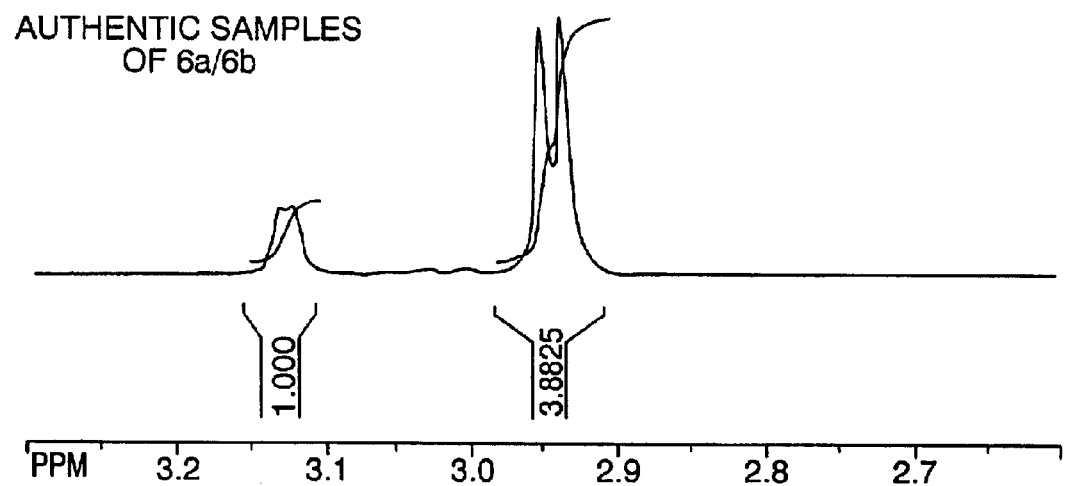
Figure 12:
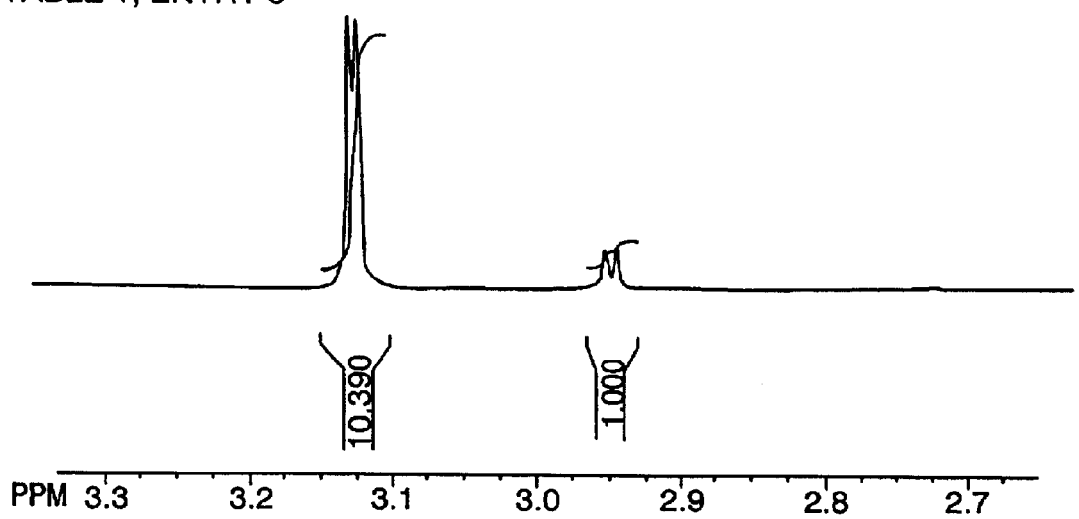
Figure 13:
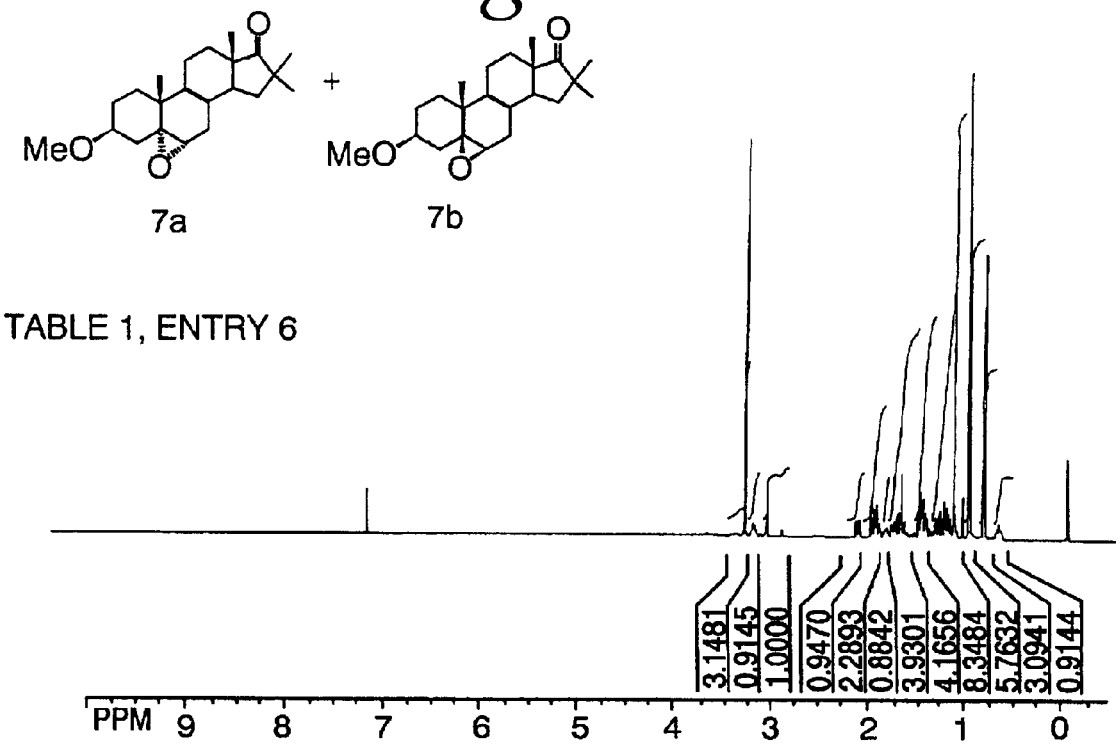
Figure 14:
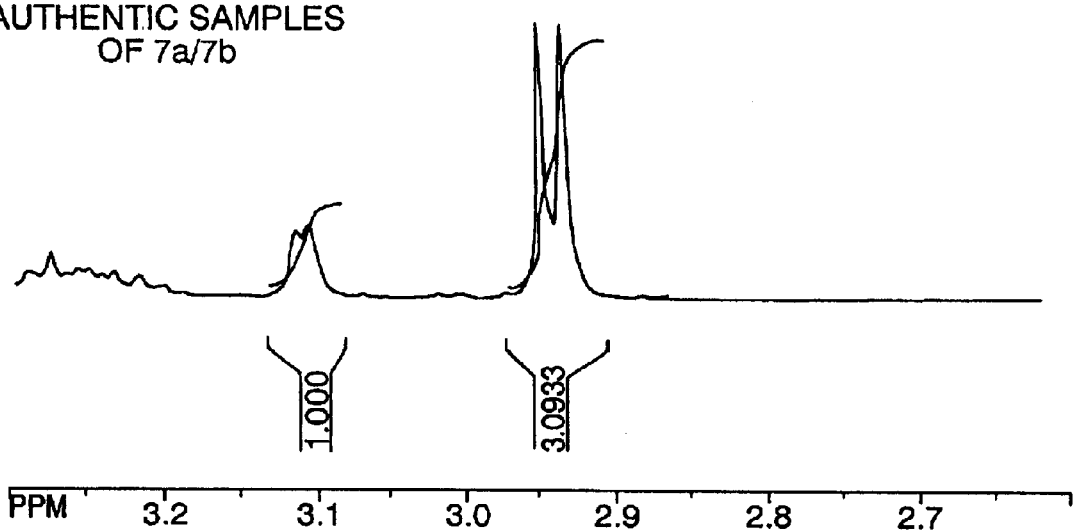
Figure 15:
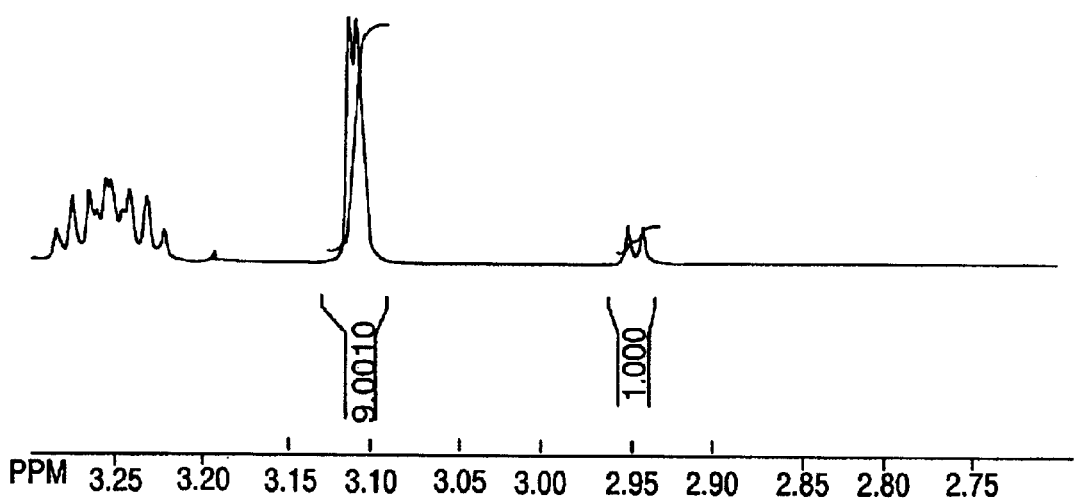
Figure 16:
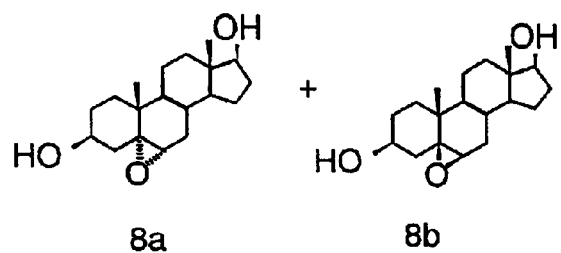
Figure 16:
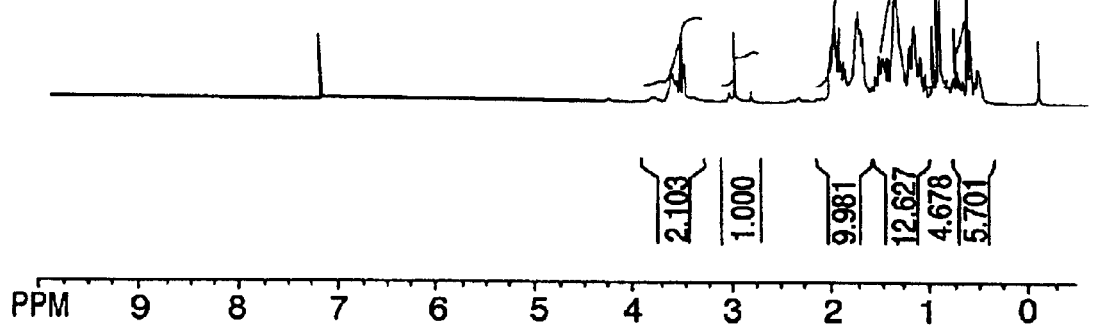
Figure 17:
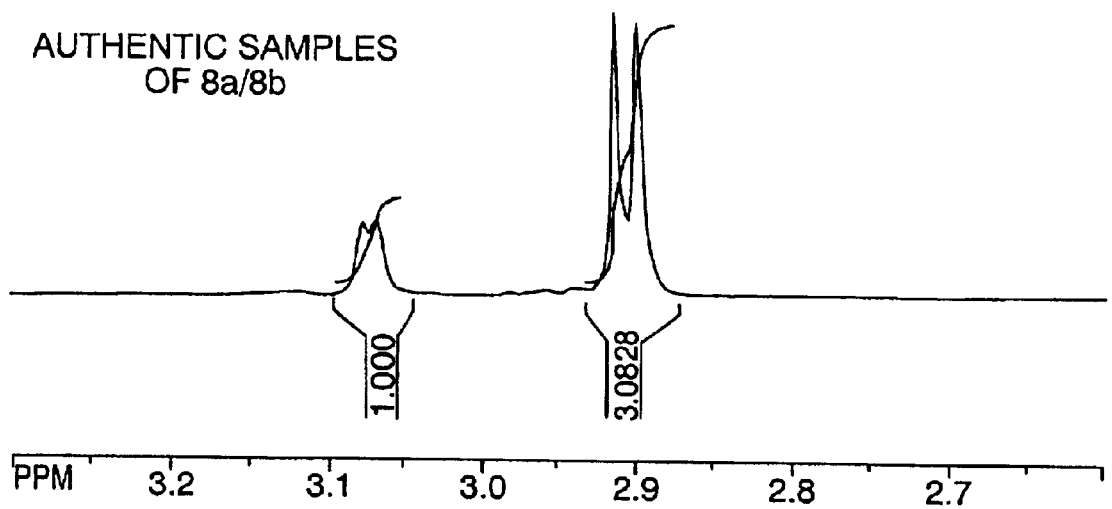
Figure 18:
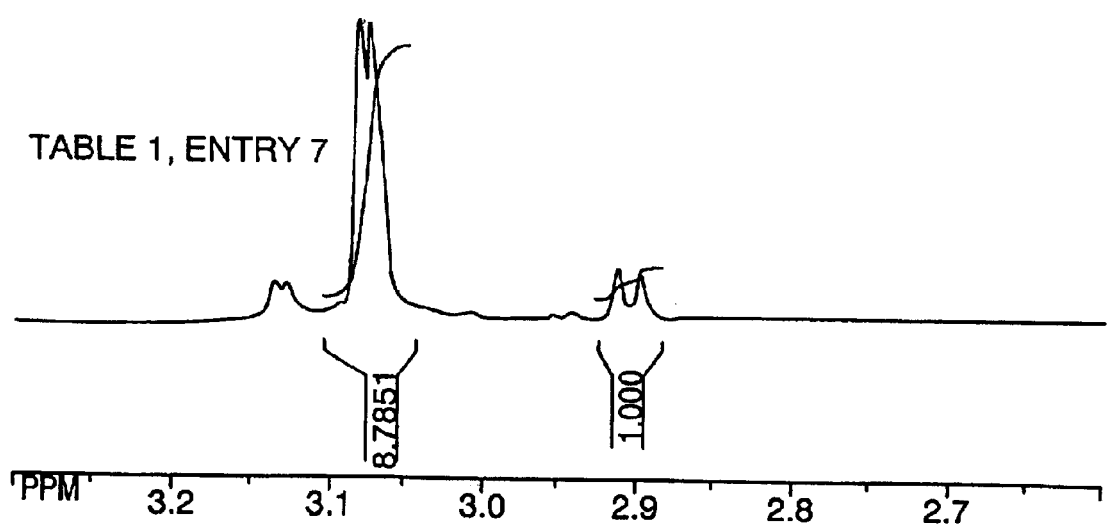
Figure 19:
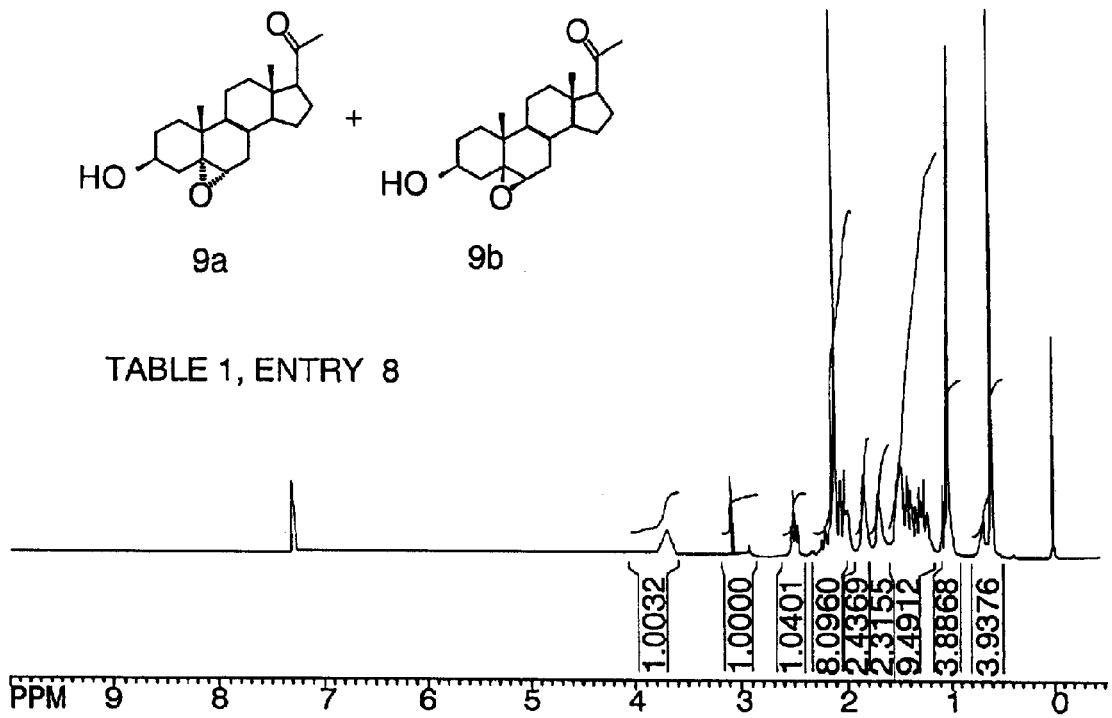
Figure 20:
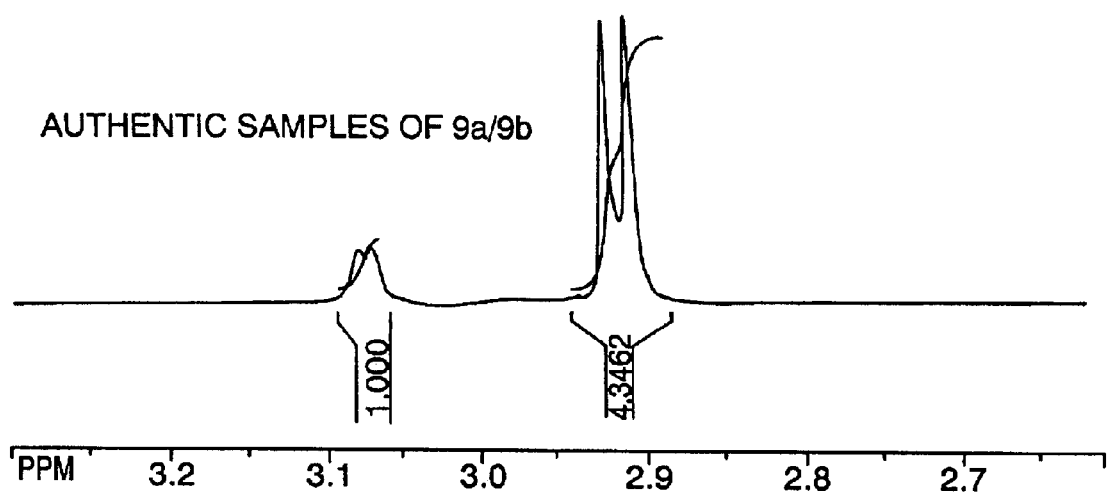
Figure 21:
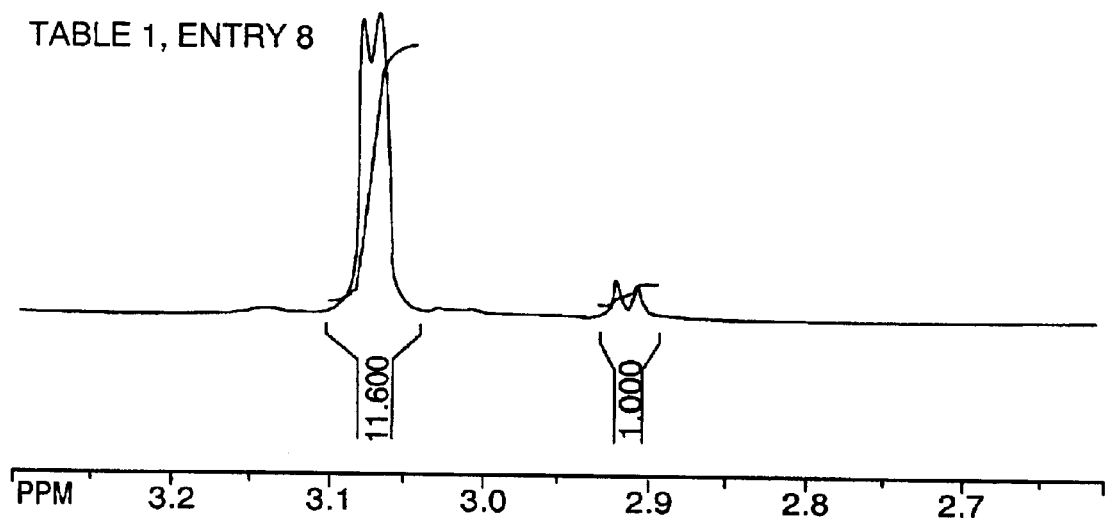
Figure 22:
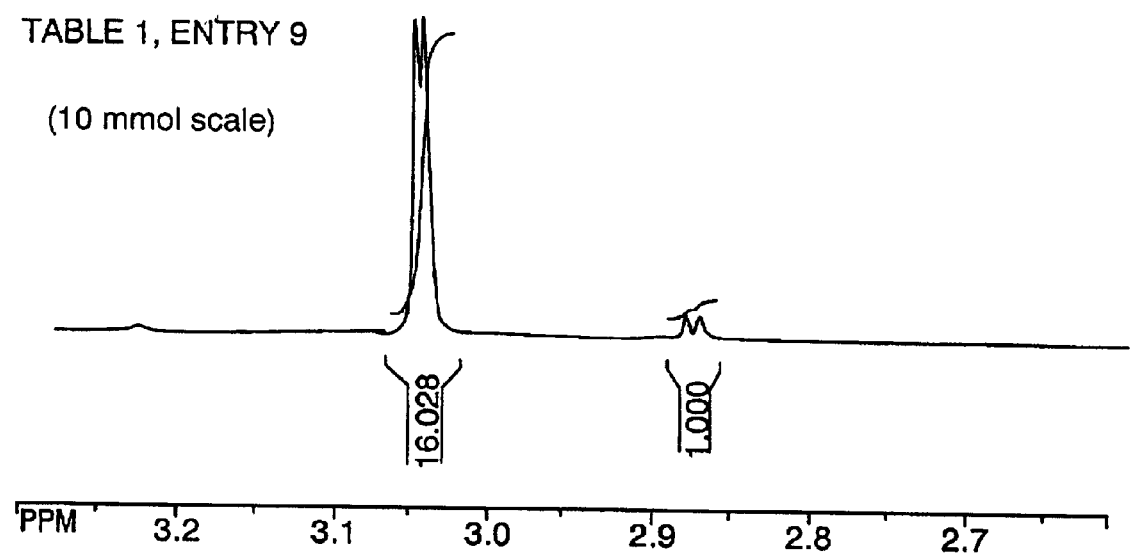
Figure 23:
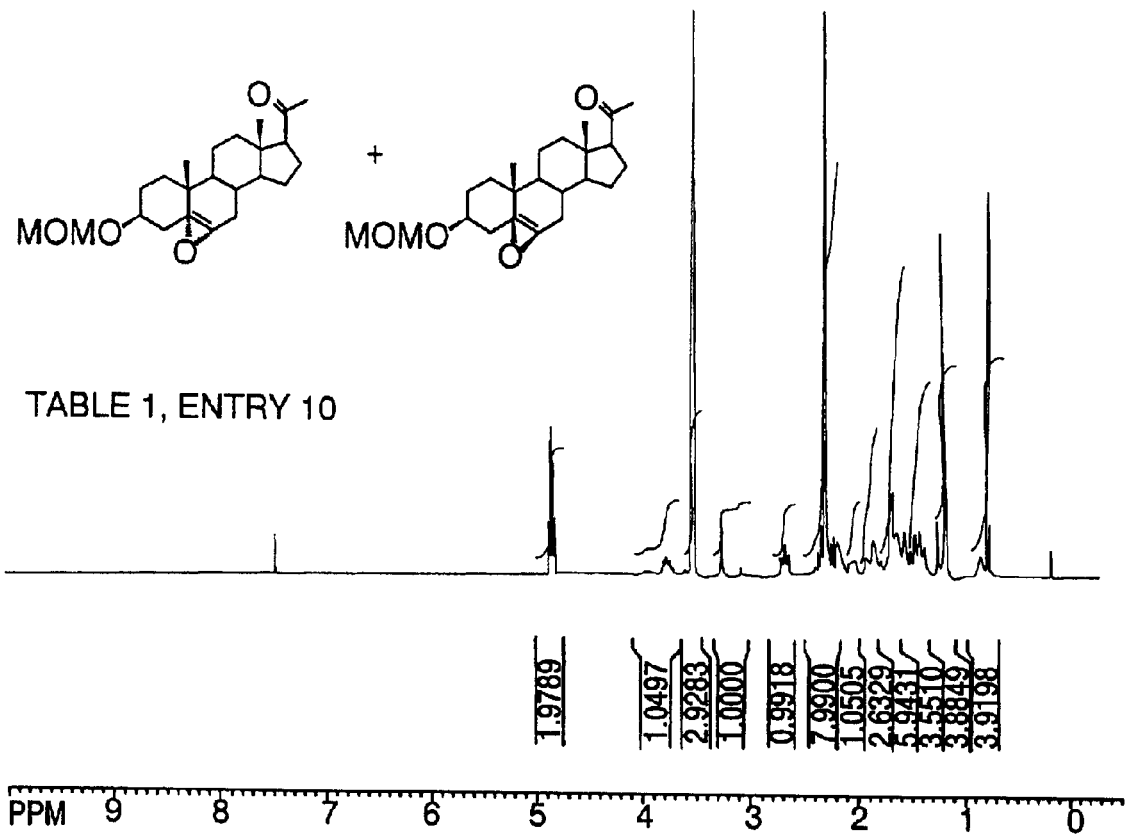
Figure 24:
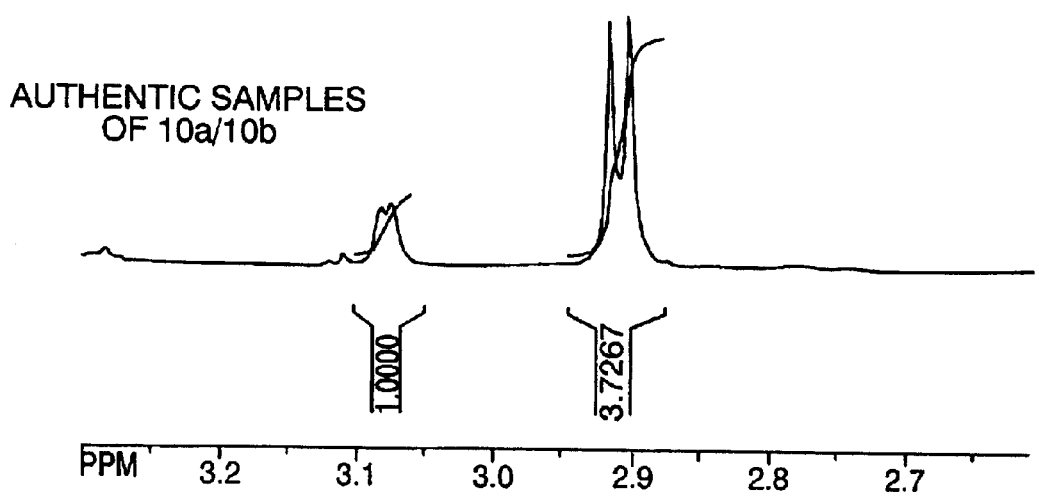
Figure 25:
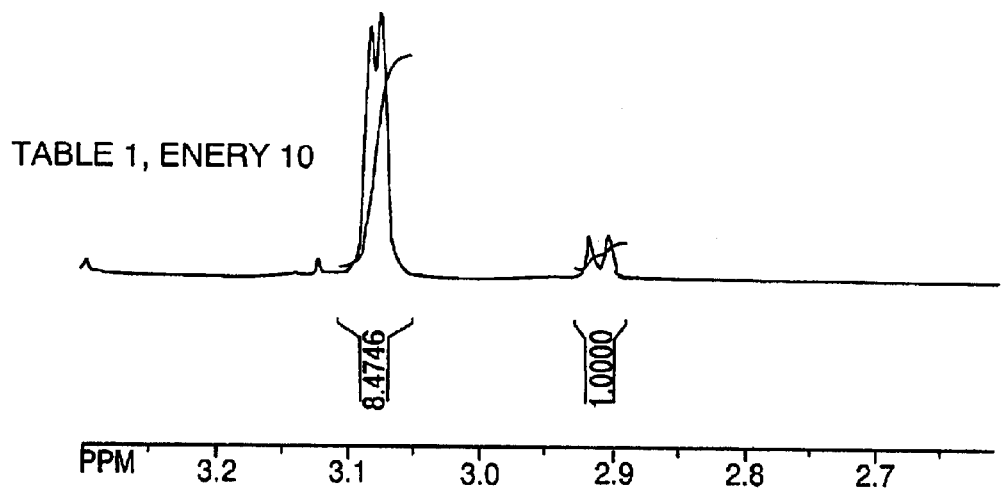
Figure 26:
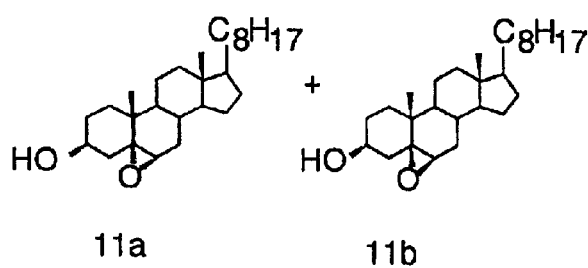
Figure 26:
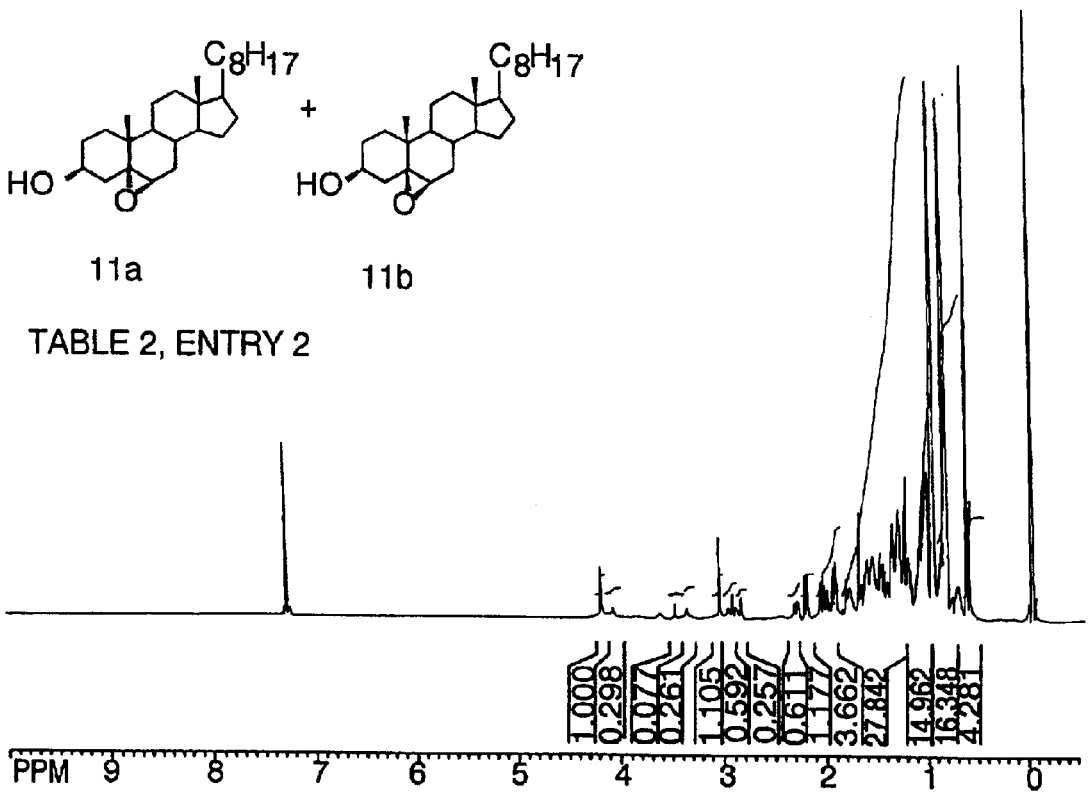
Figure 27:
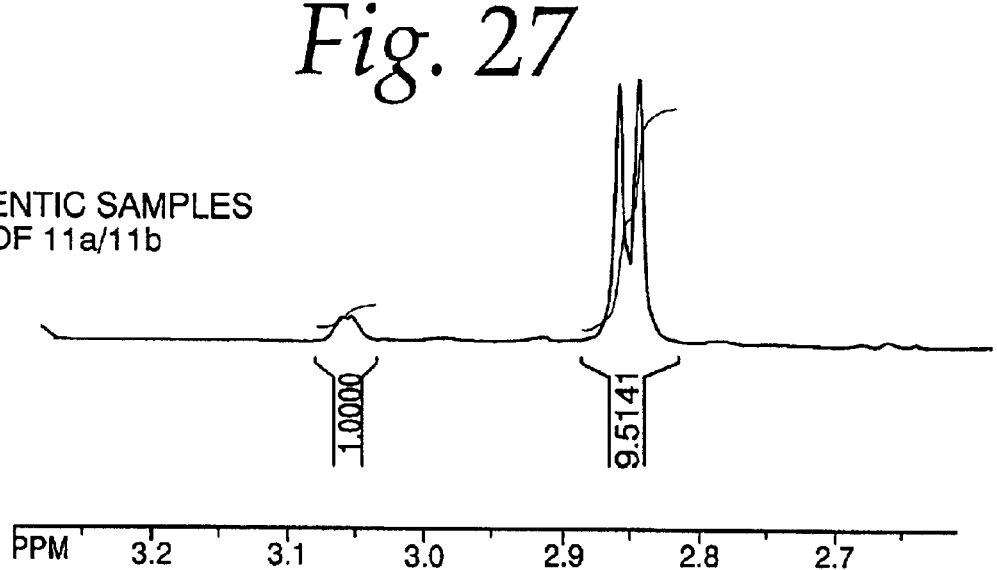
Figure 28:
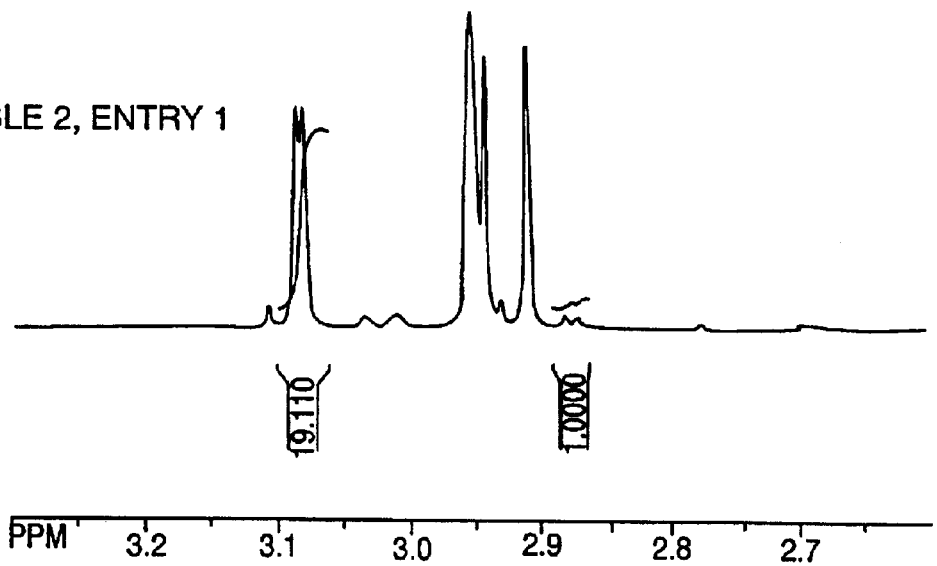
Figure 29:
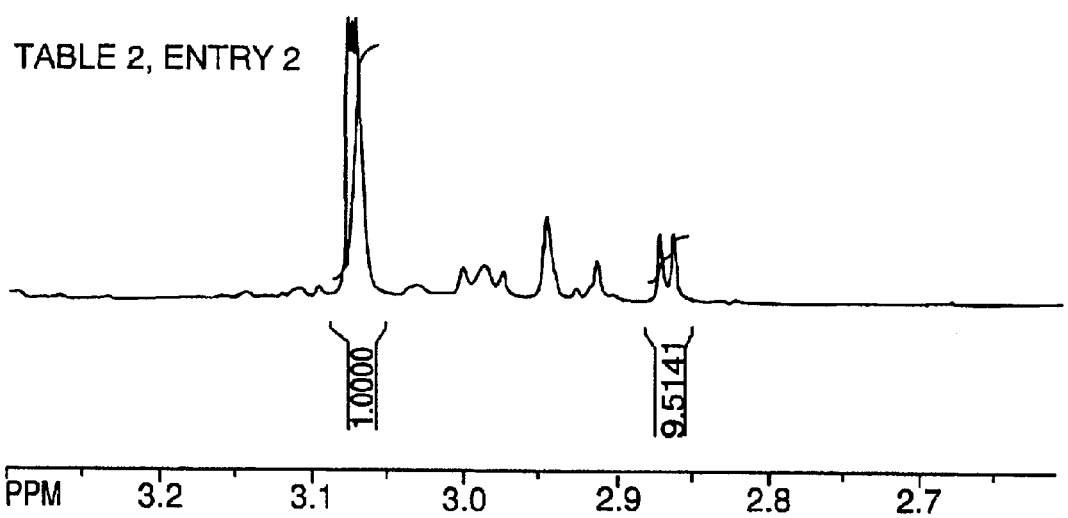
Figure 30:
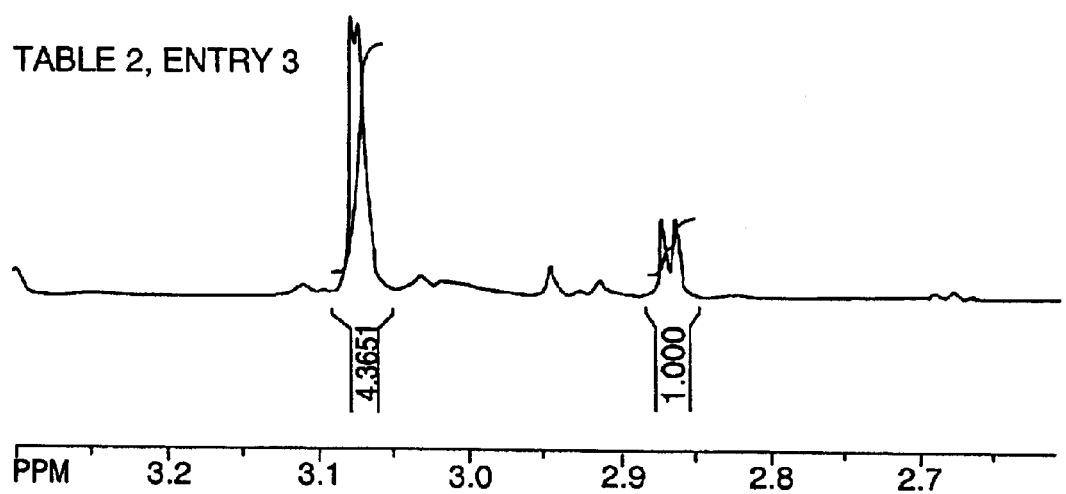
Figure 31:
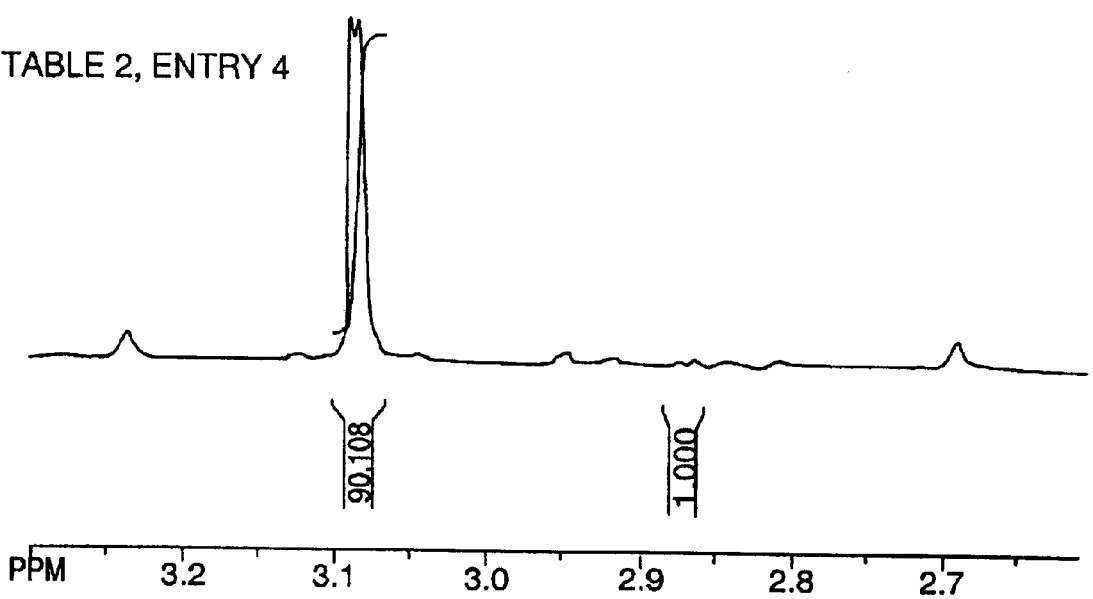
Figure 32:
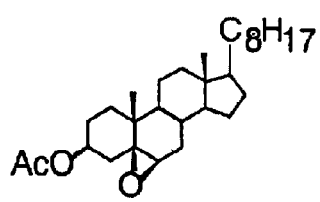
Figure 32:
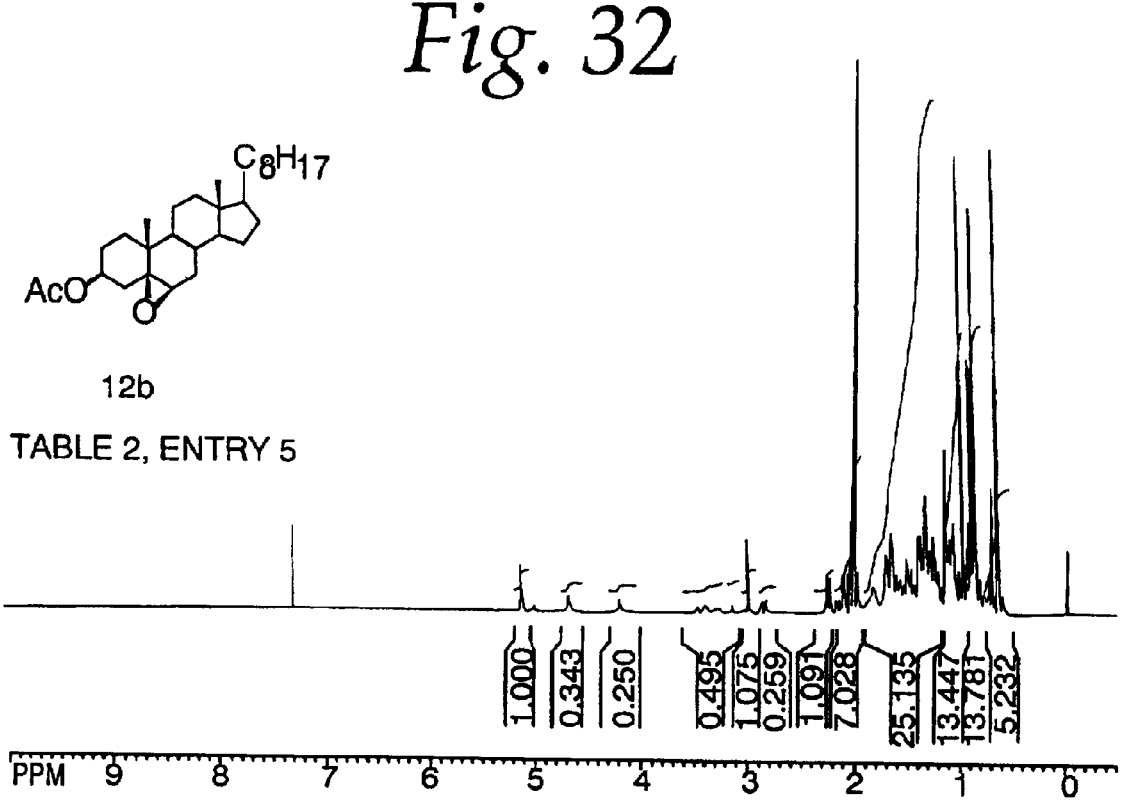
Figure 33:
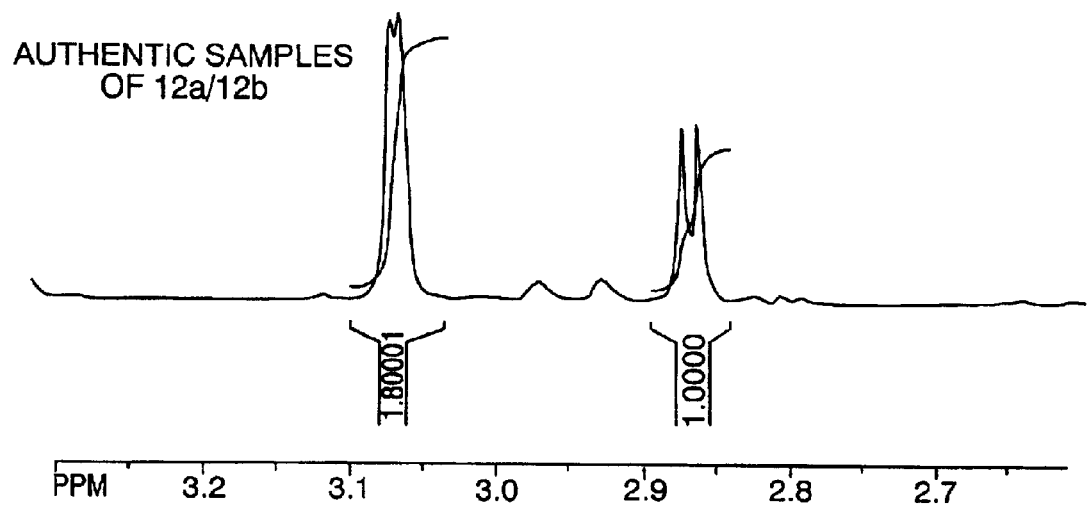
Figure 34:
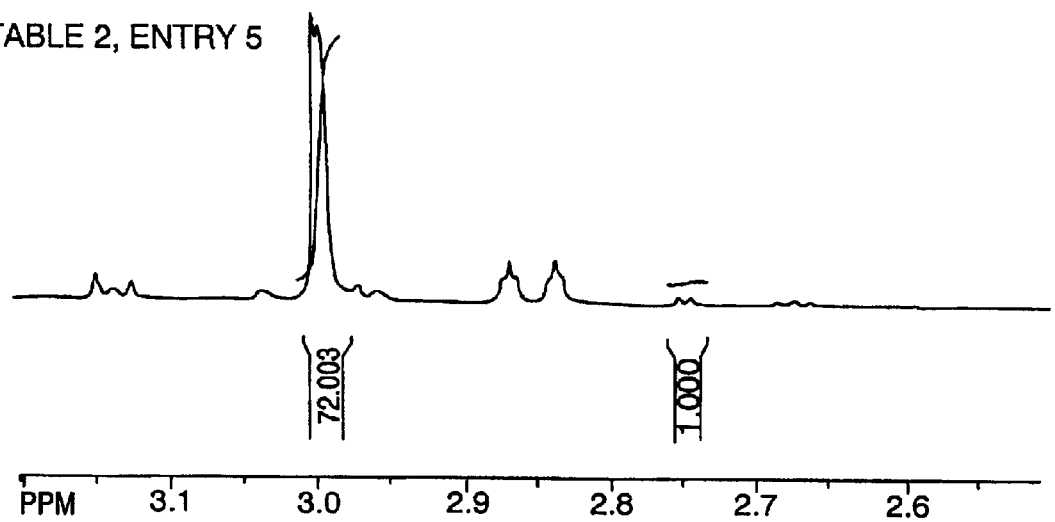
Figure 35:
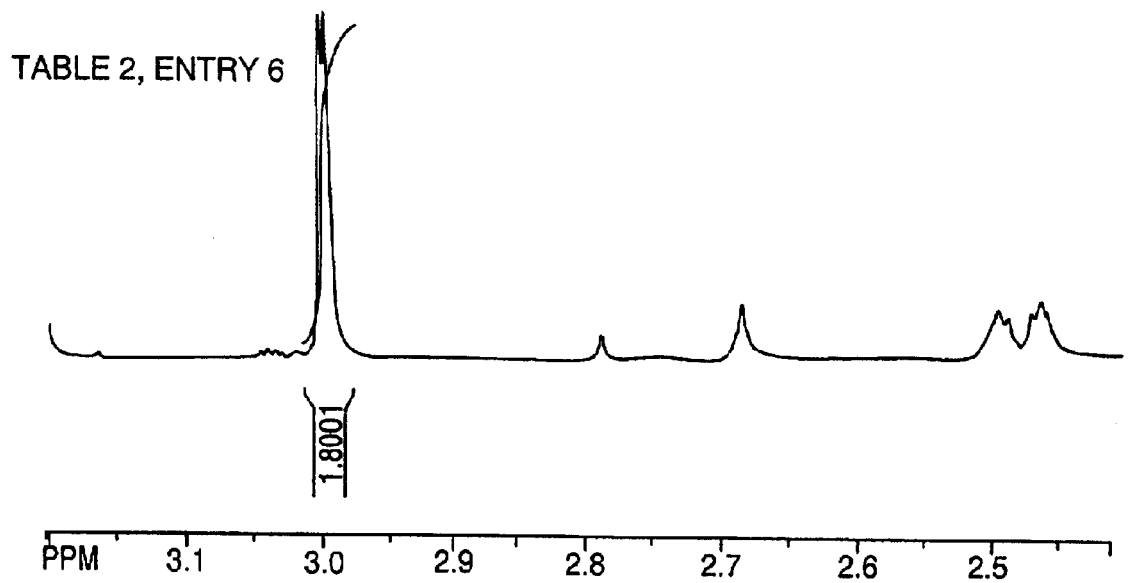
Figure 36:
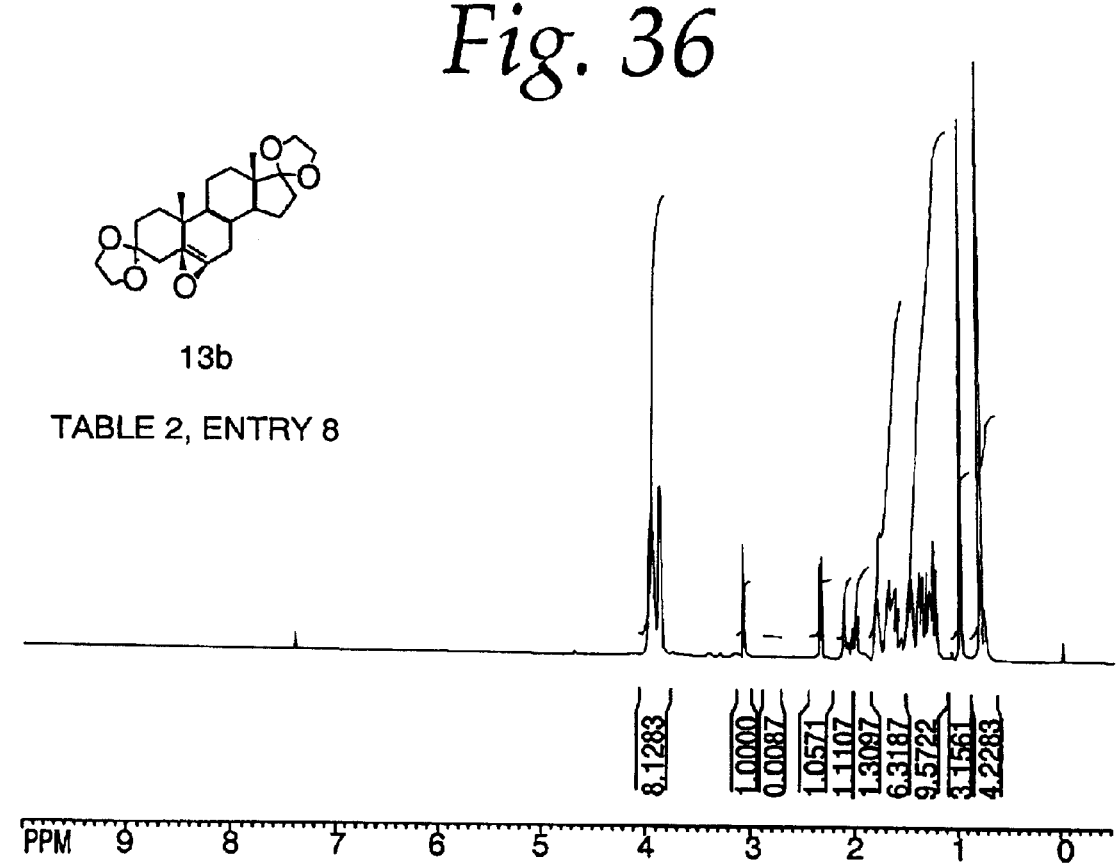
Figure 37:
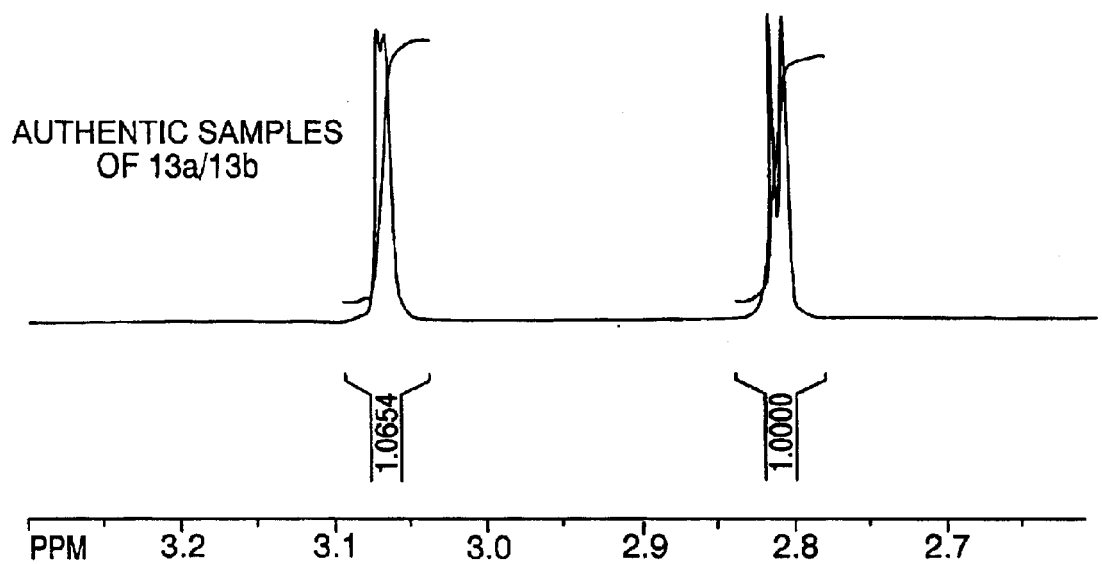
Figure 38:
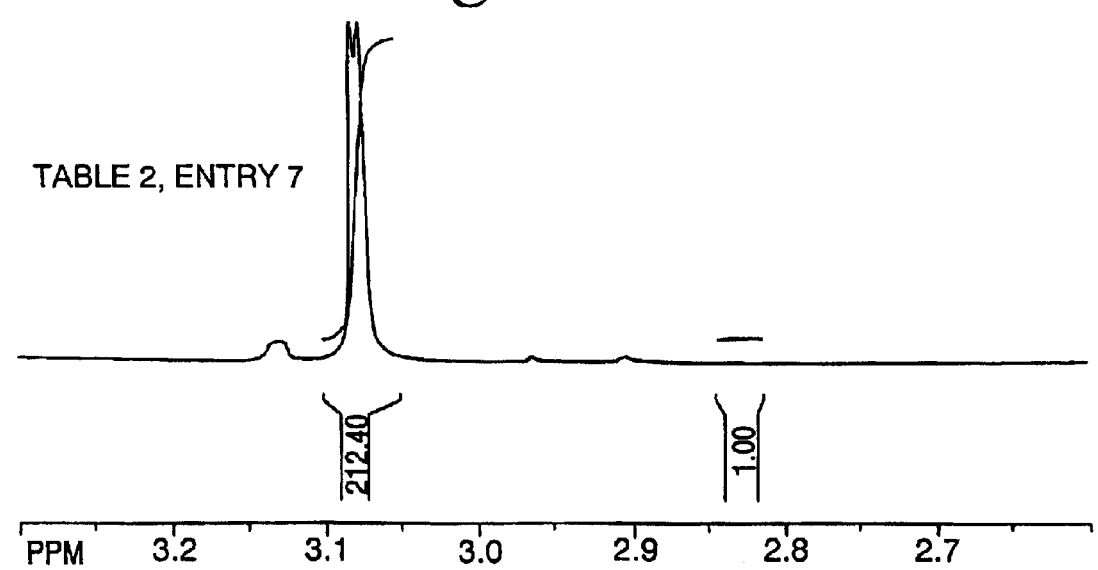
Figure 39:
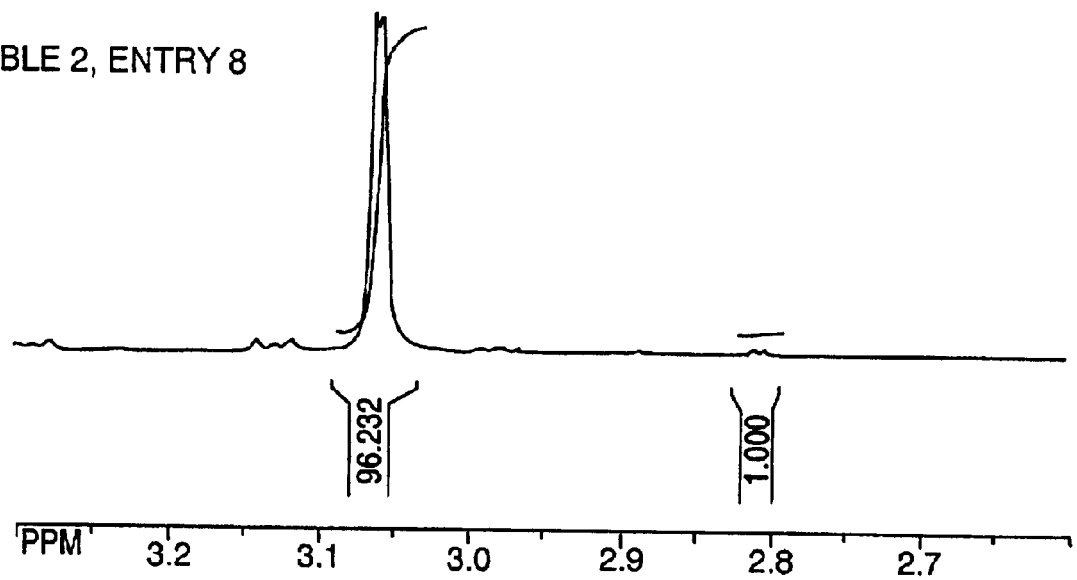
Figure 40:
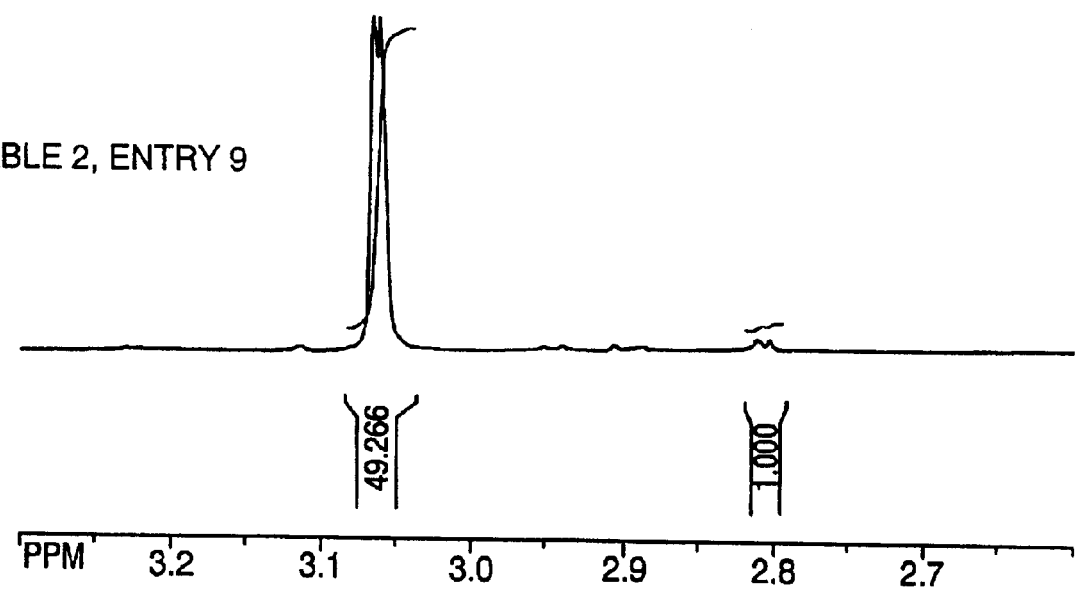
Figure 41:
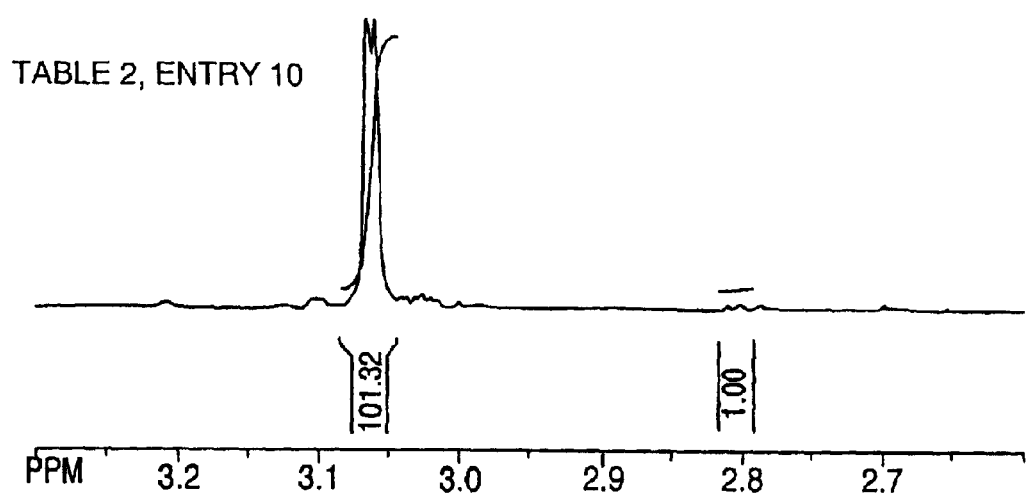
Figure 42:
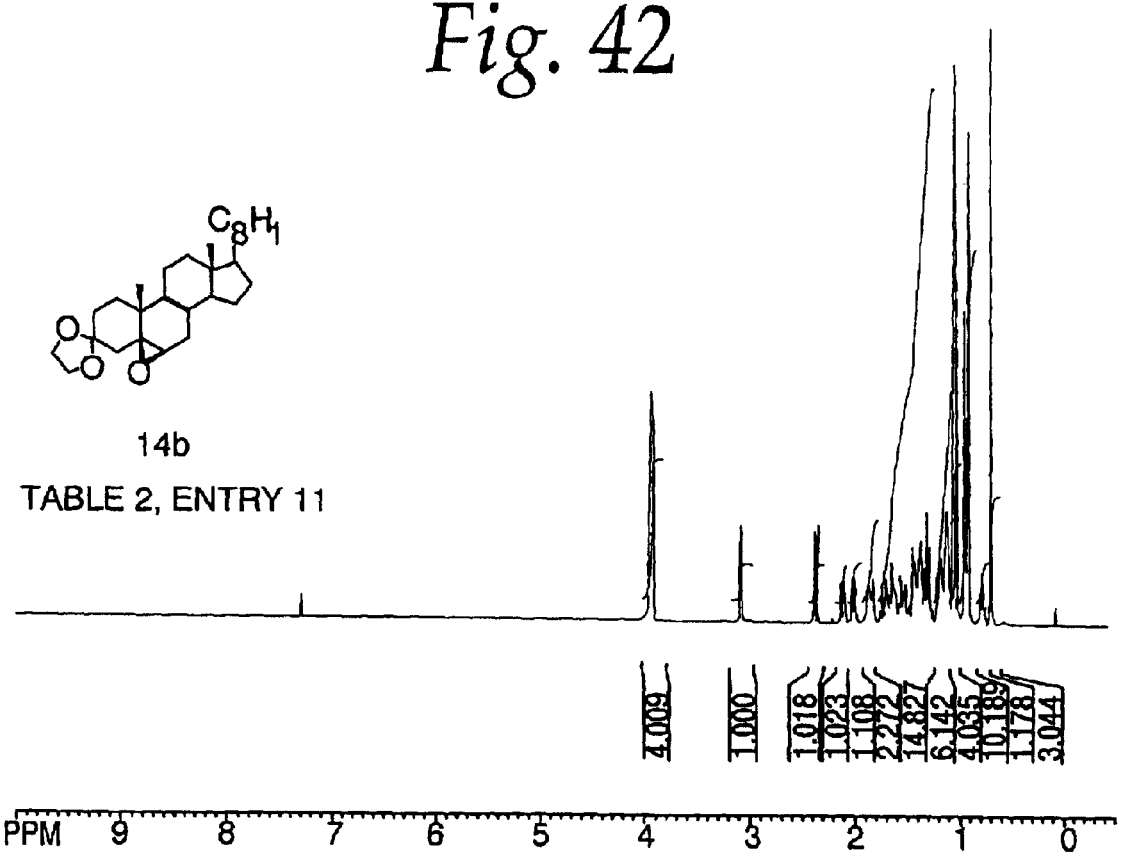
Figure 43:
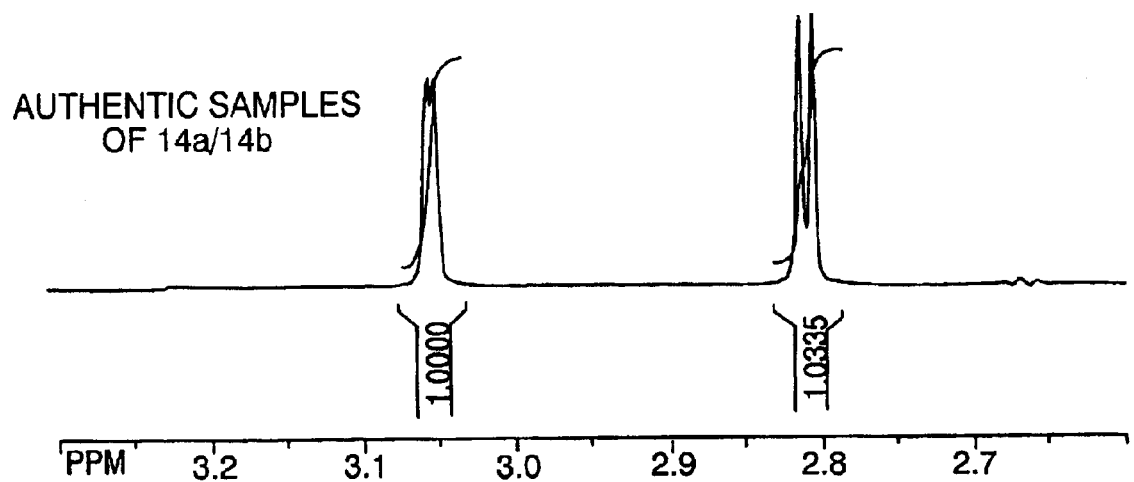
Figure 44:
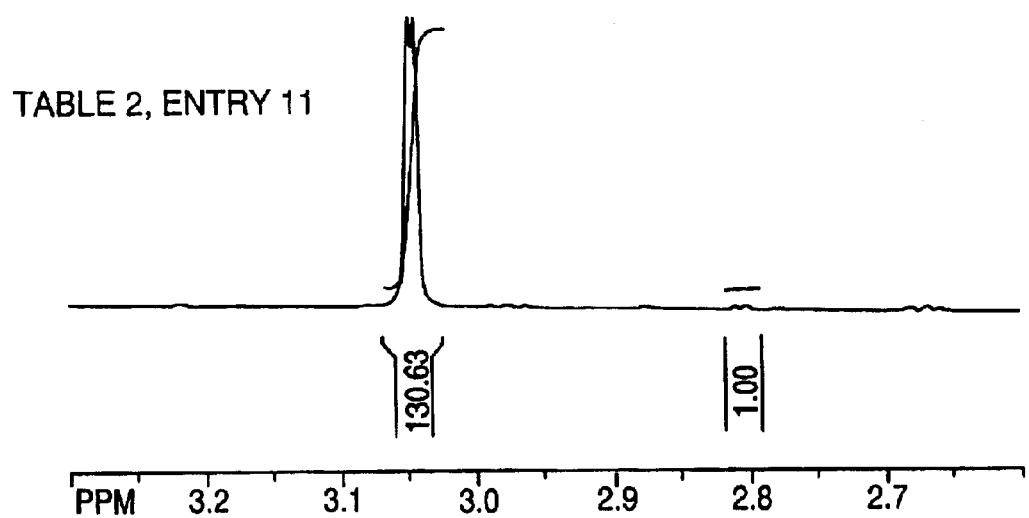
Figure 45:
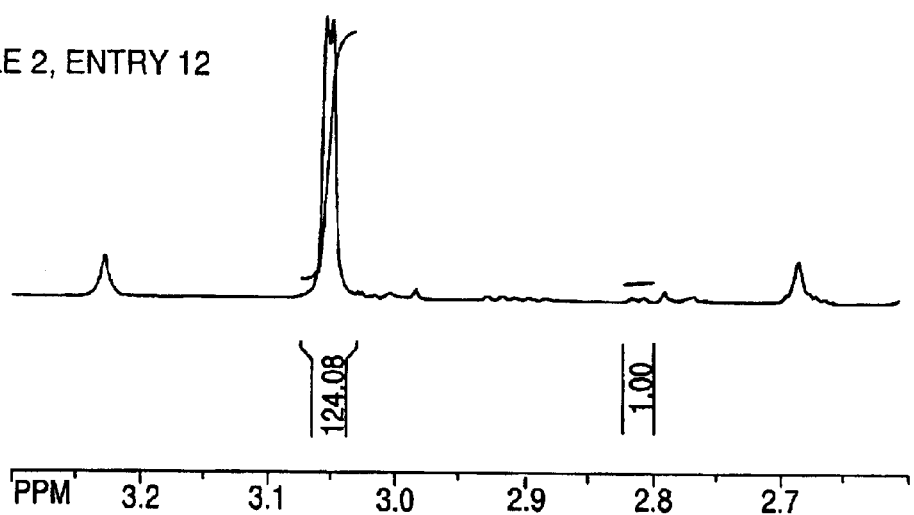
Figure 46:
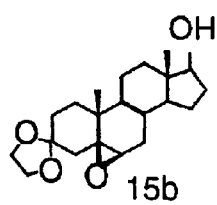
Figure 46:
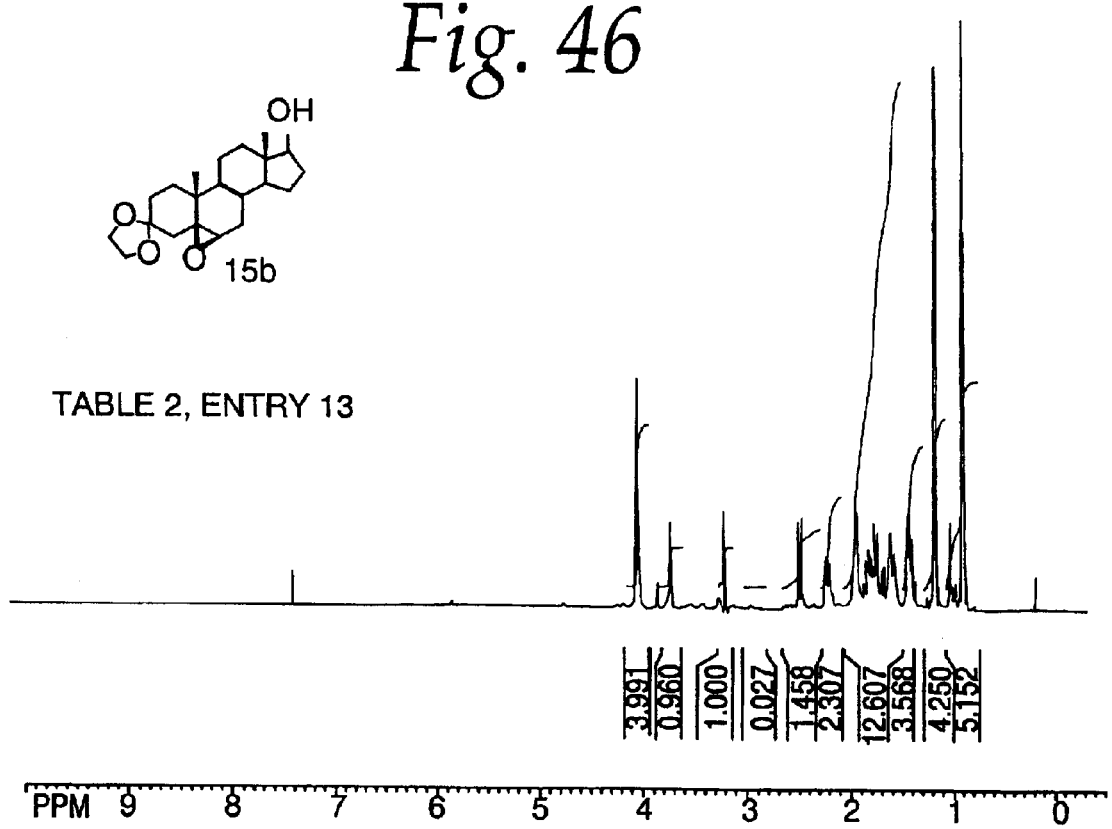
Figure 47:
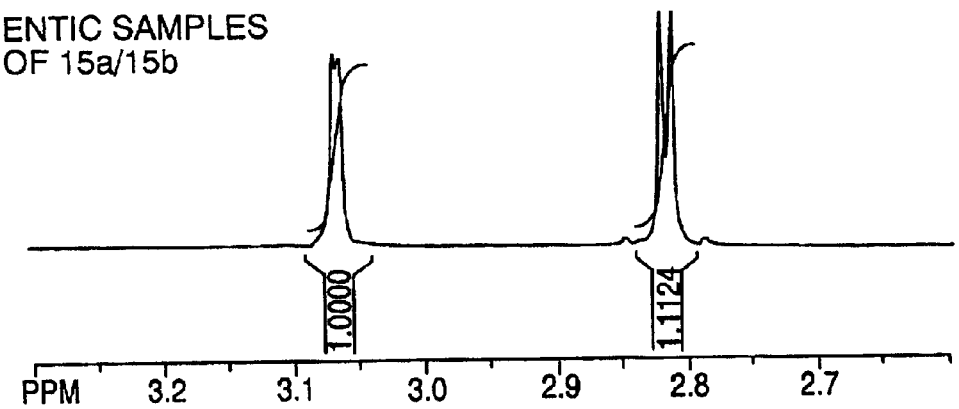
Figure 48:
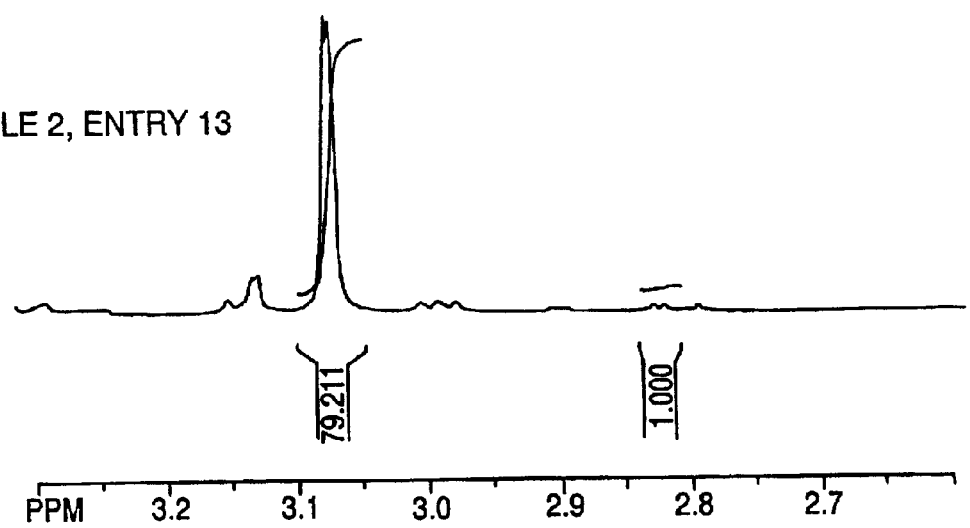
Figure 49:
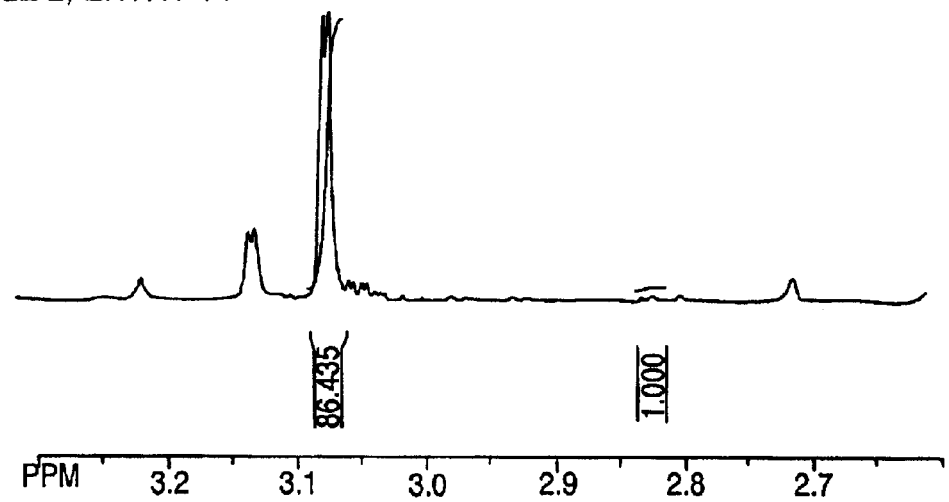
Figure 50:
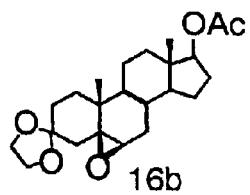
Figure 50:
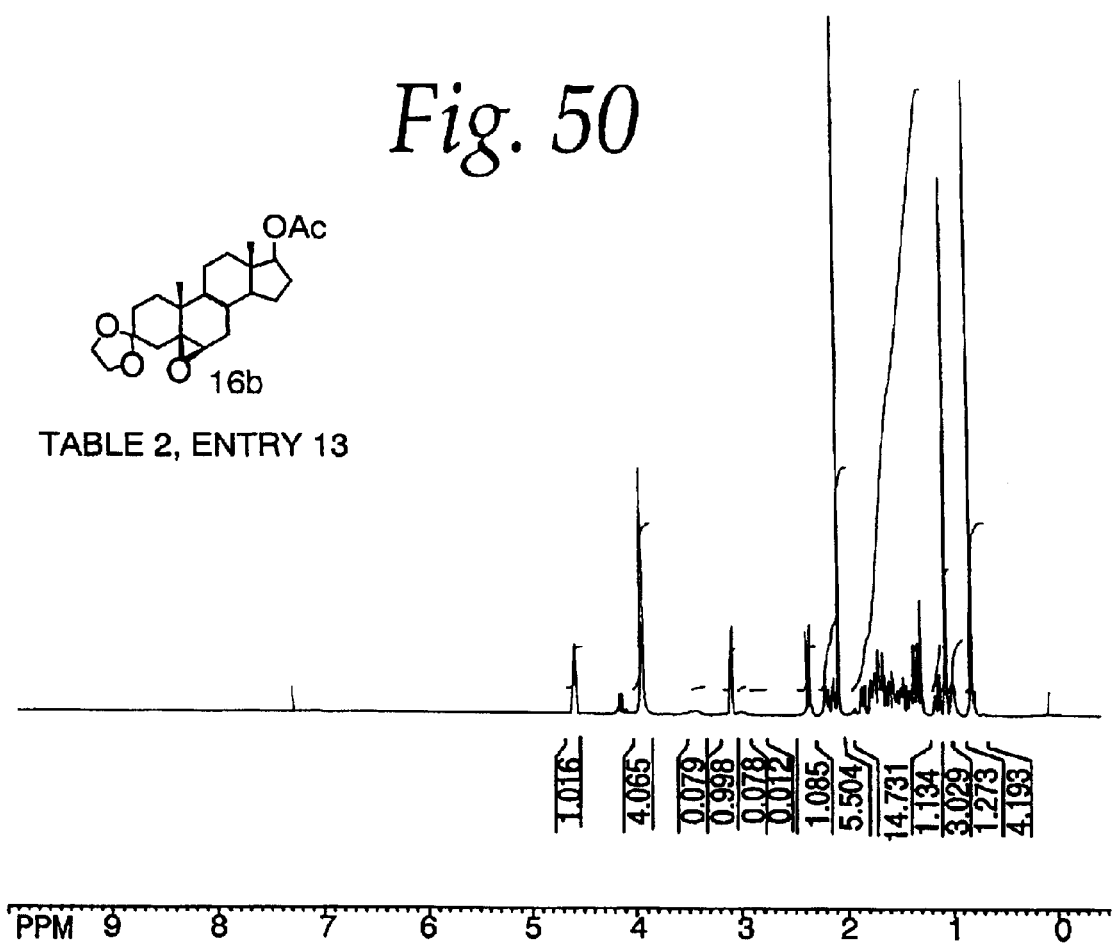
Figure 51:
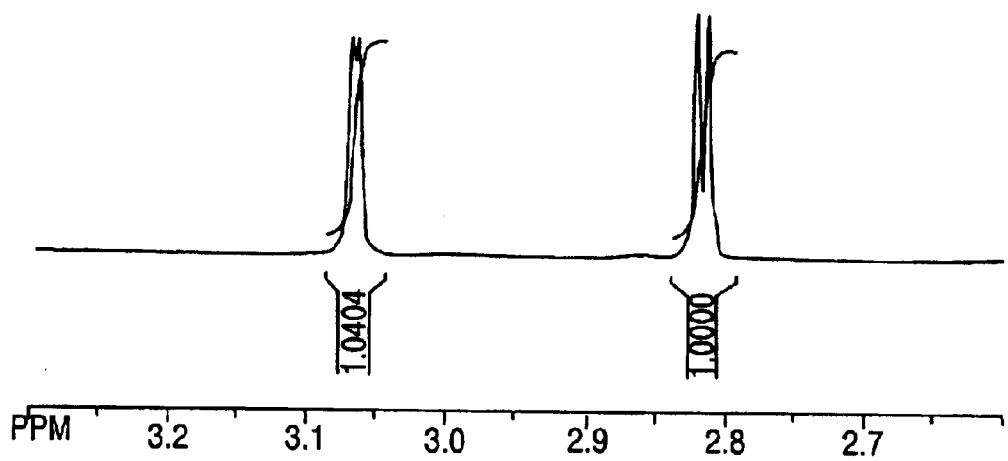
Figure 52:
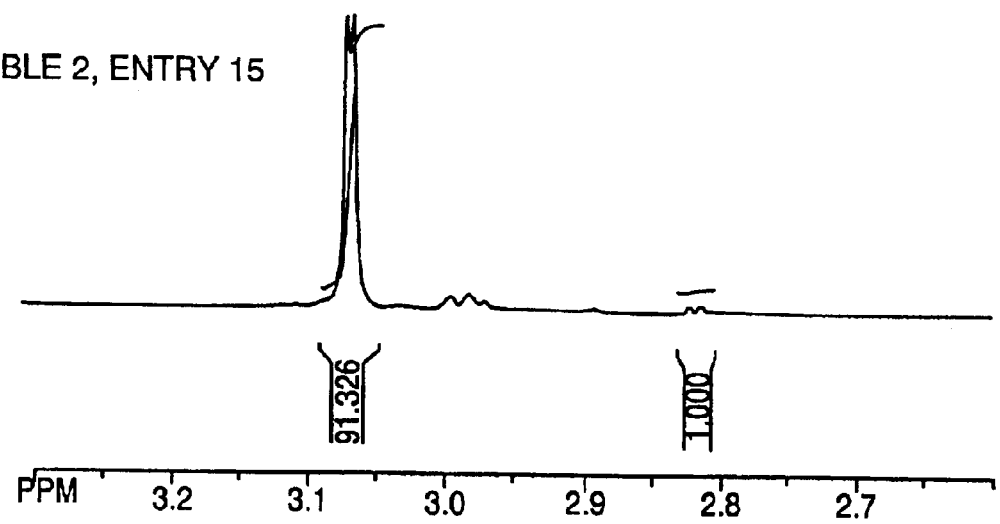
Figure 53:
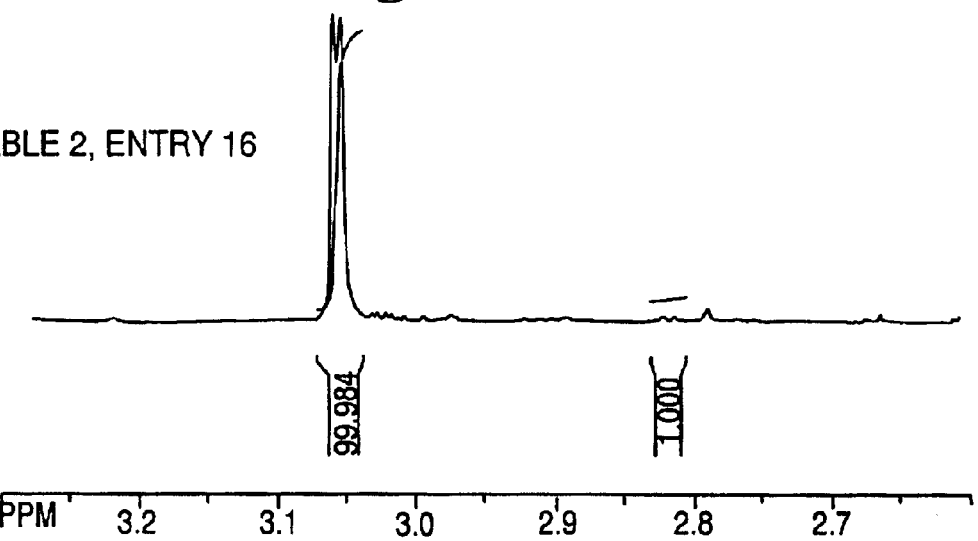
Figure 54:
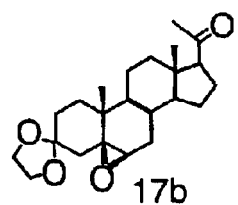
Figure 54:
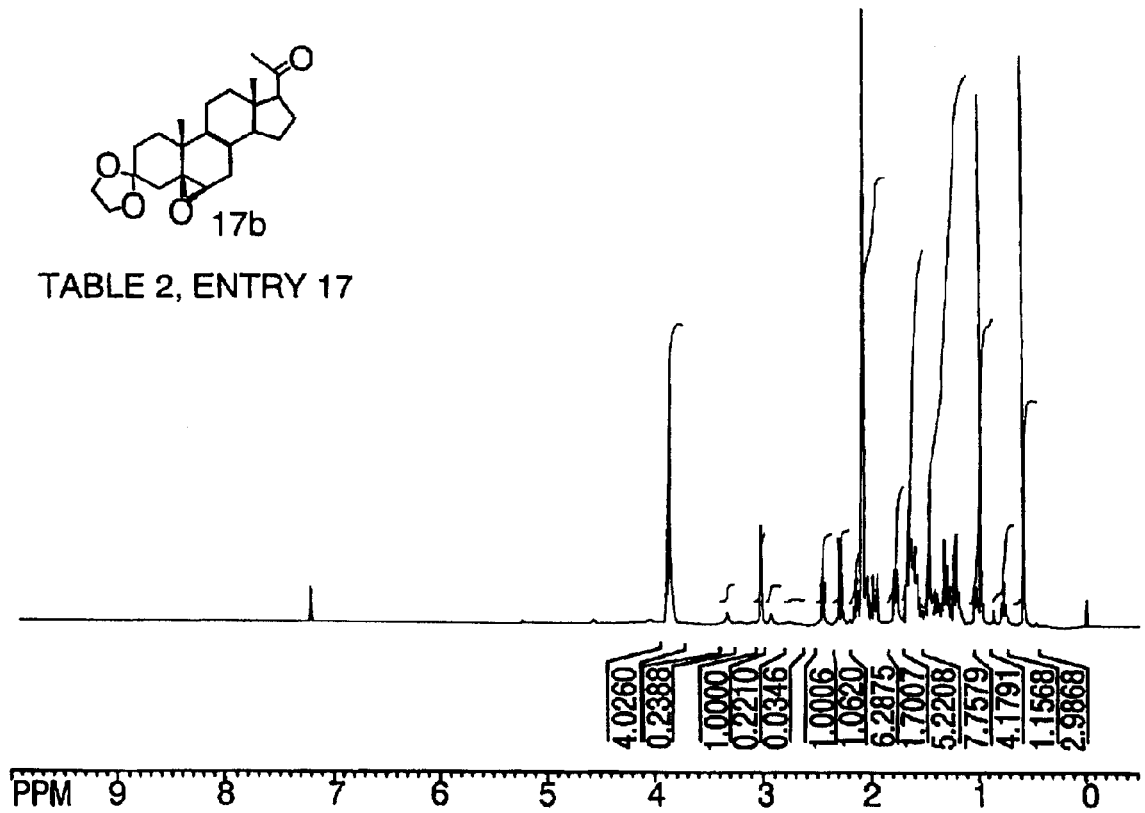
Figure 55:
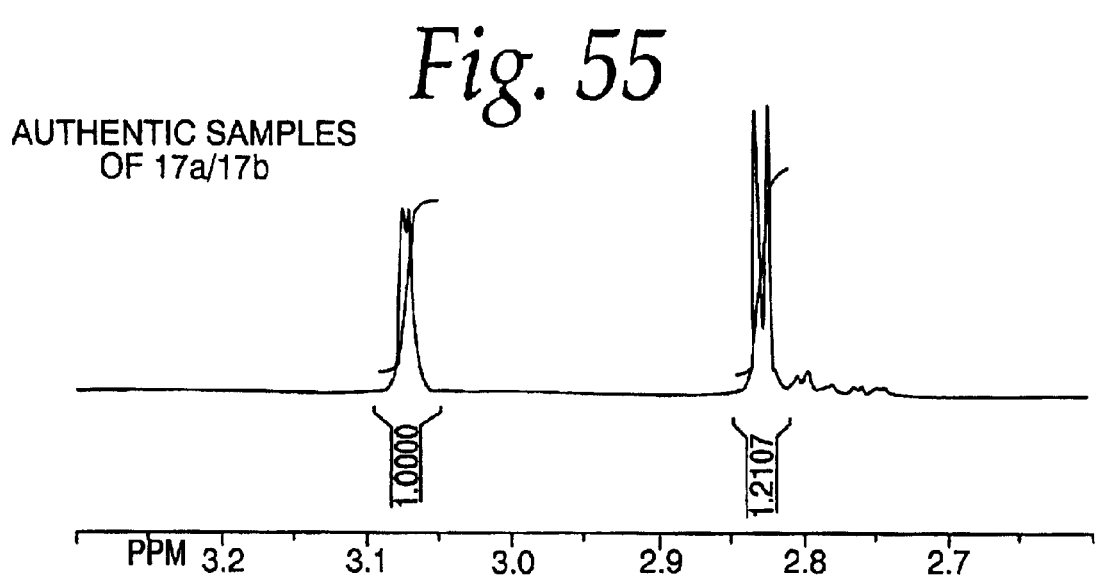
Figure 56:
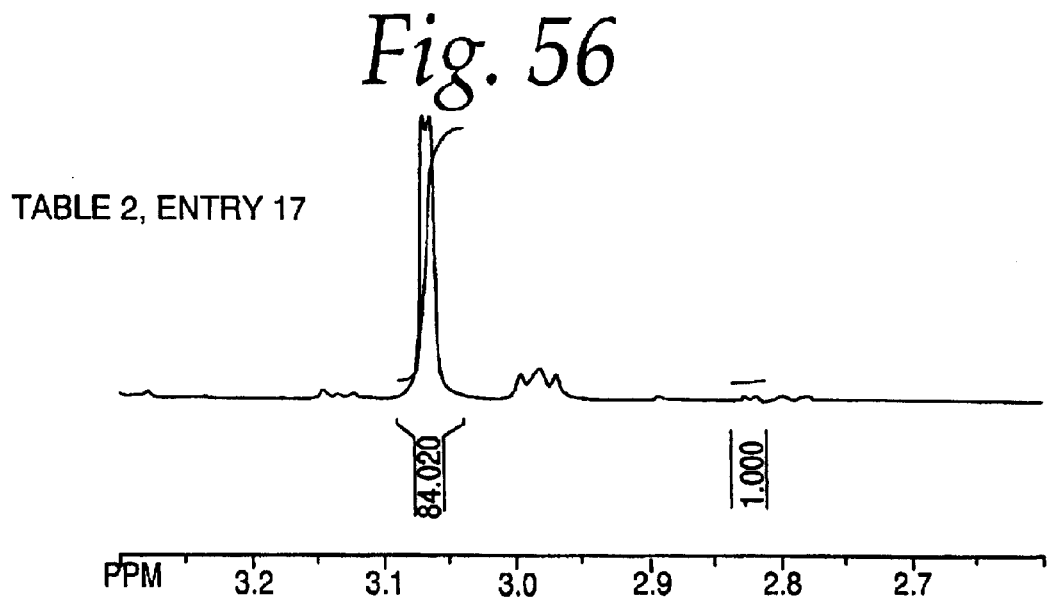
Figure 57:
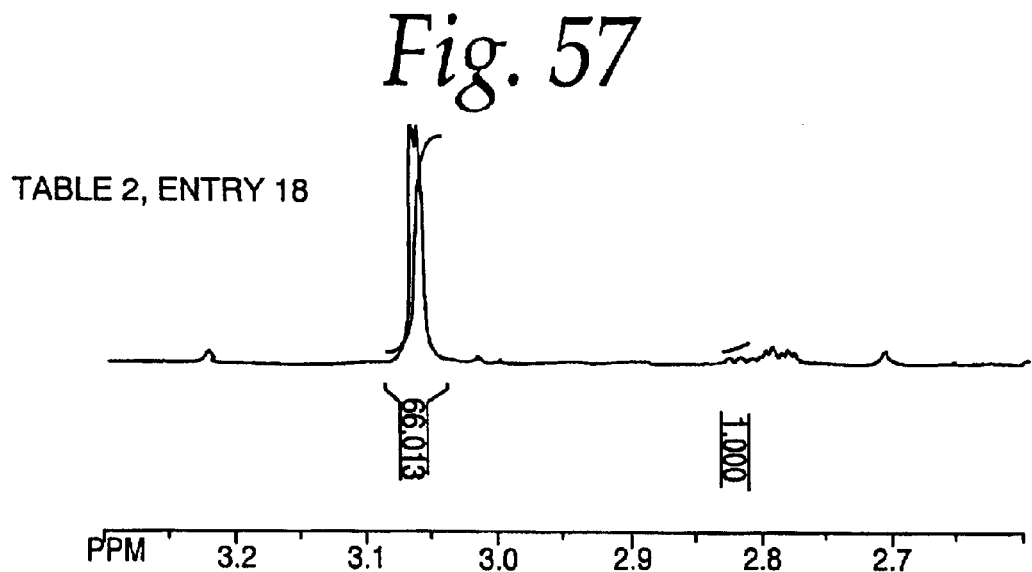
Figure 58:
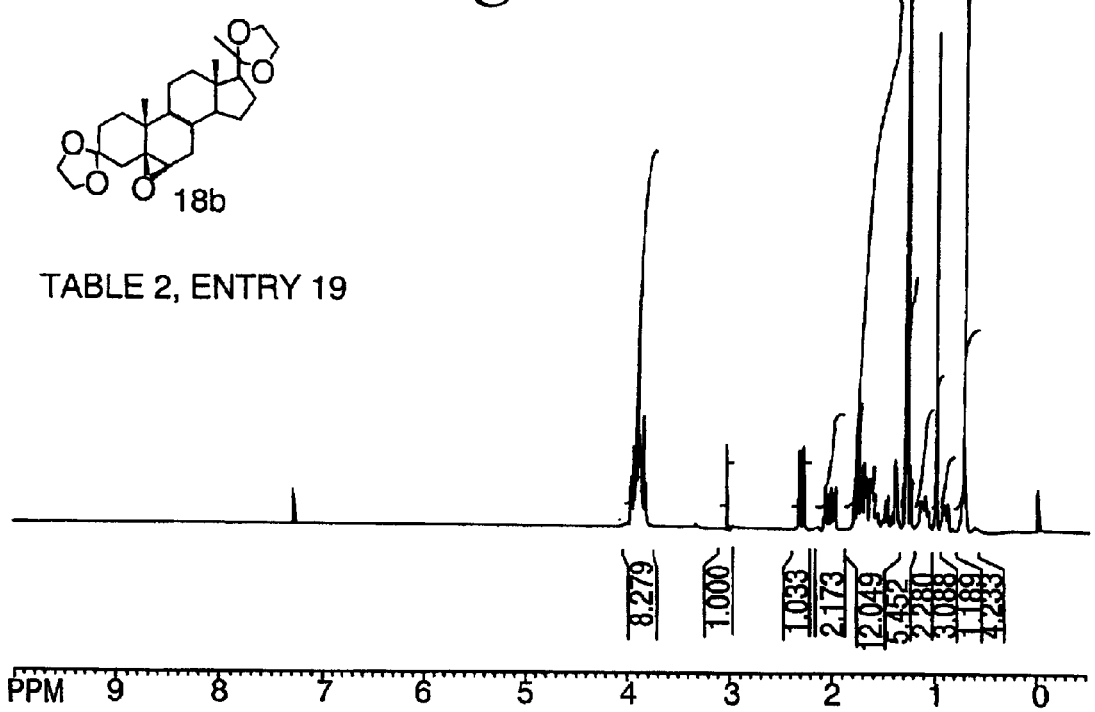
Figure 59:
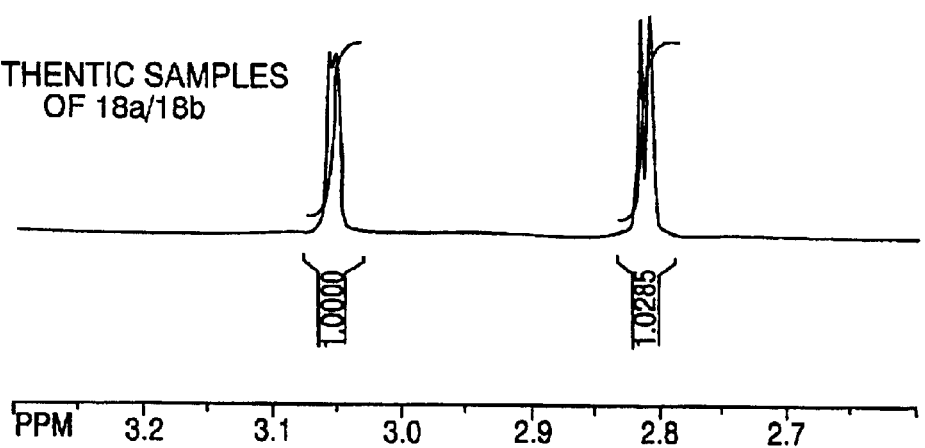
Figure 60:
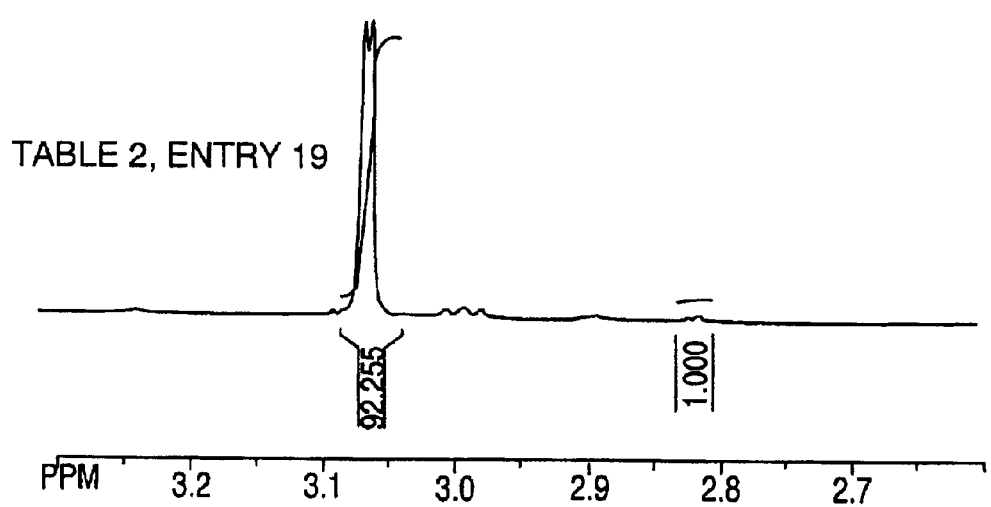
Figure 61:
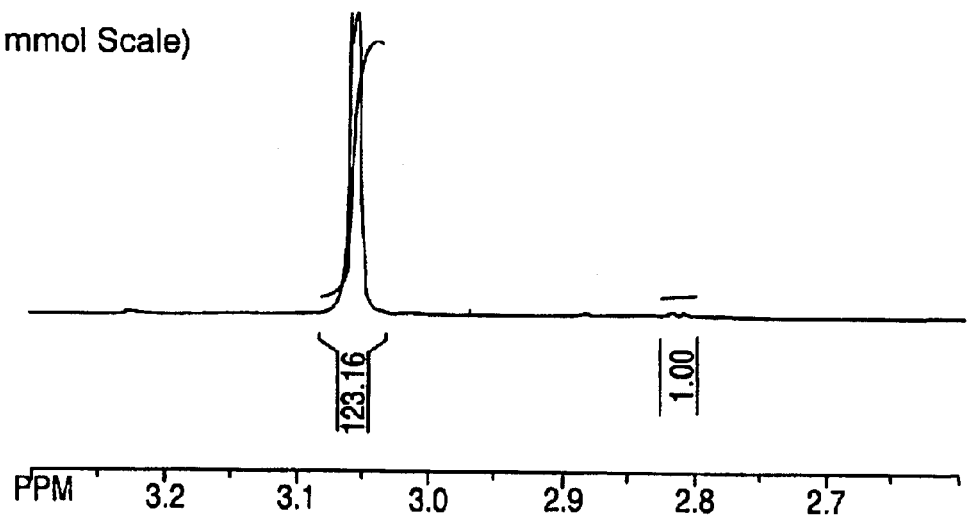
Figure 62:
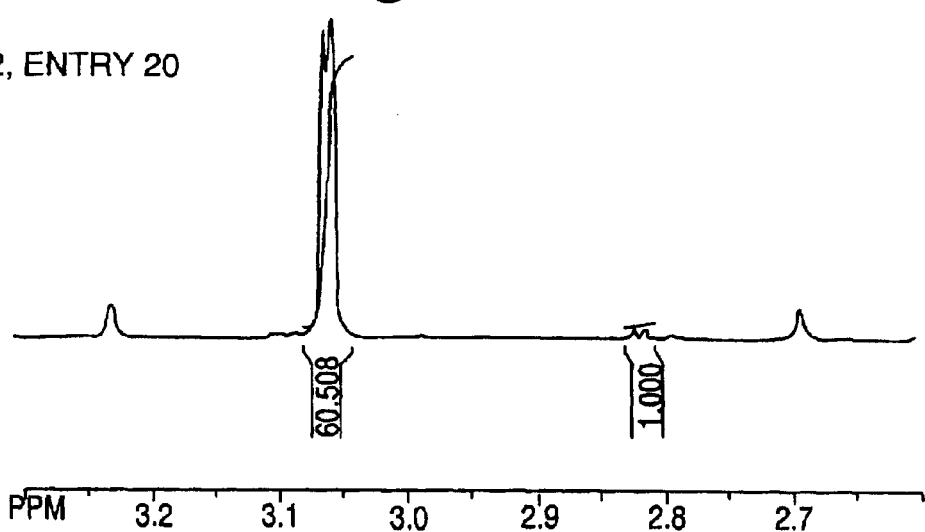
Figure 63:
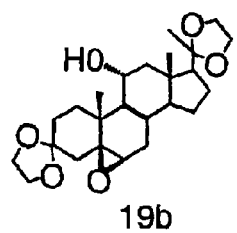
Figure 63:
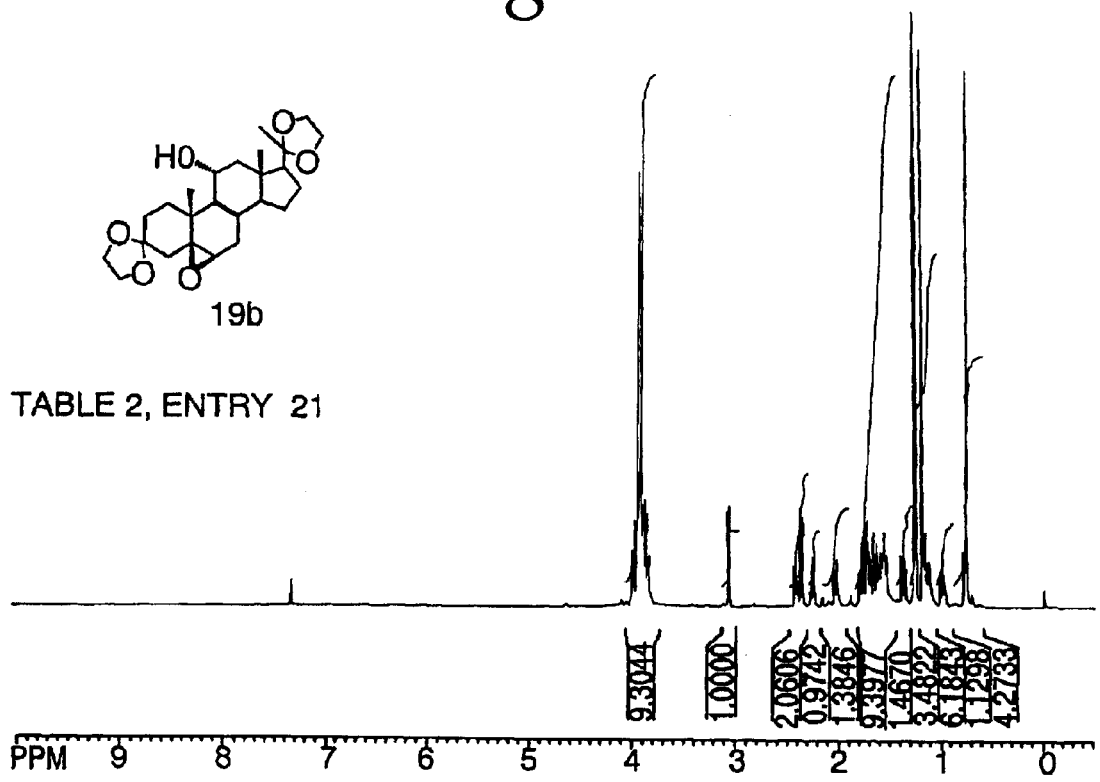
Figure 64:
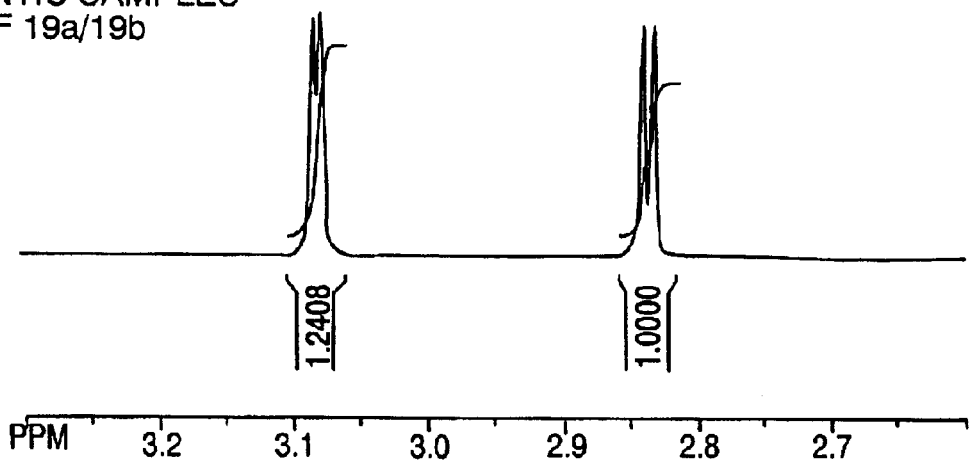
Figure 65:
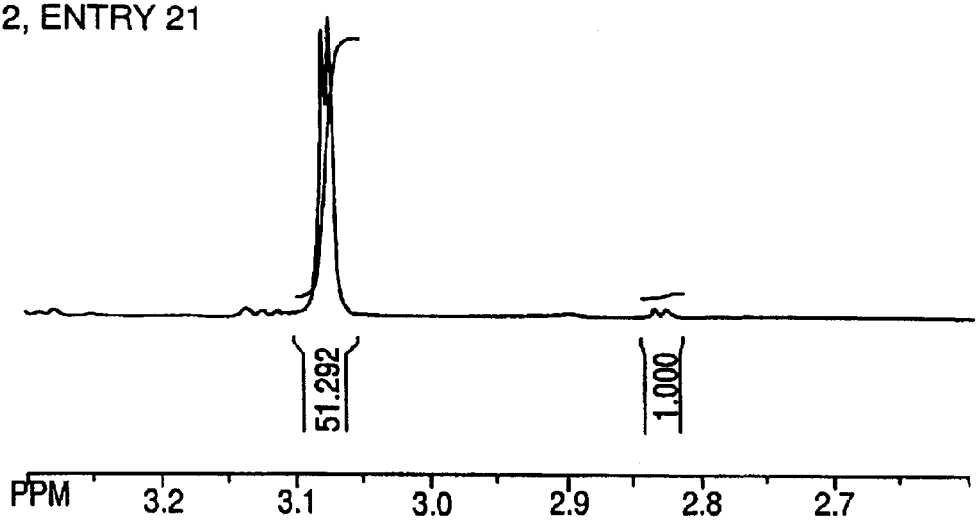
Figure 66:
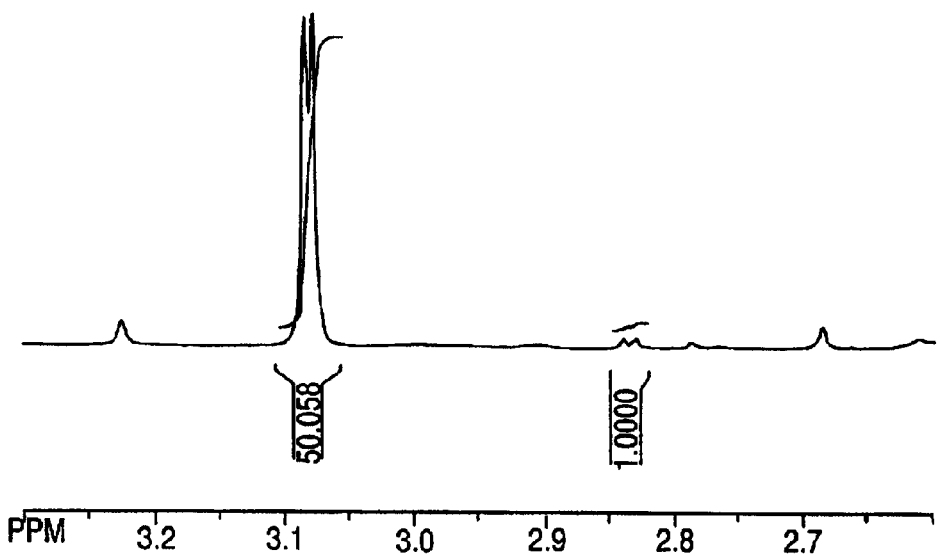
Figure 67:
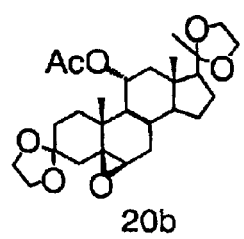
Figure 67:
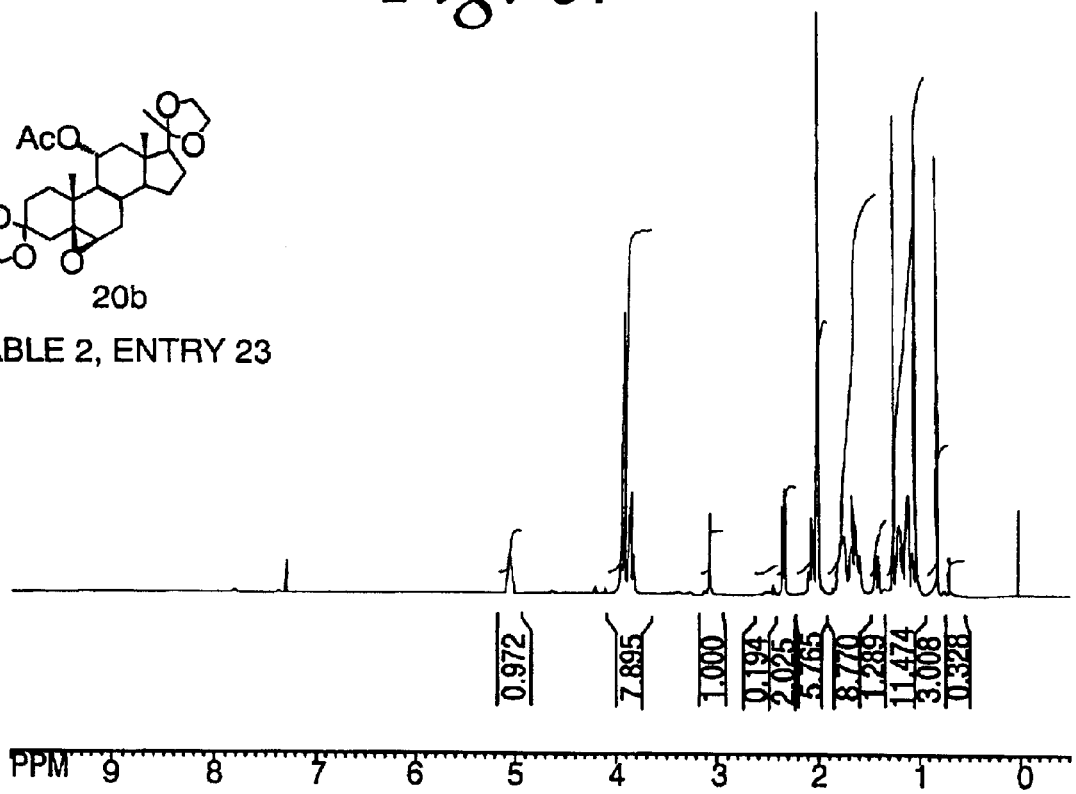
Figure 68:
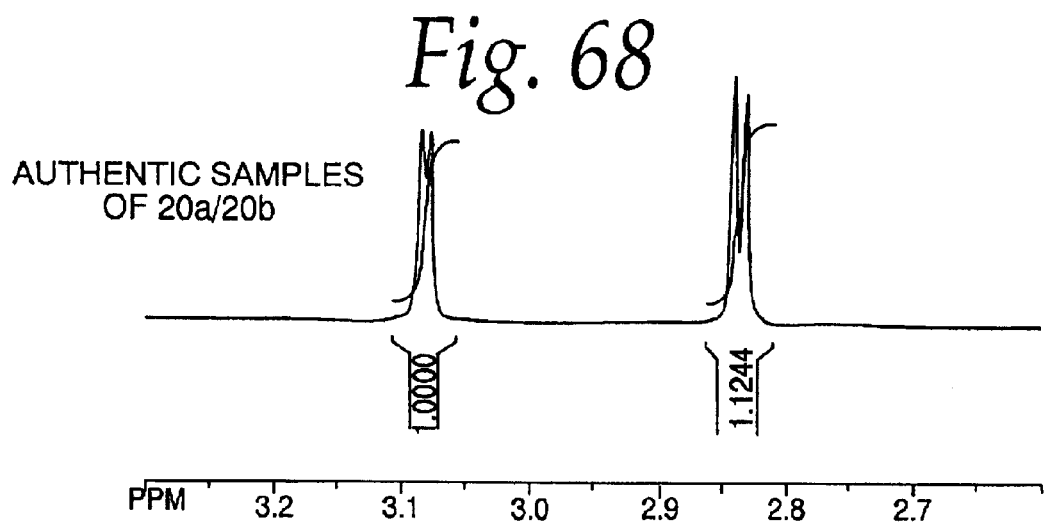
Figure 69:
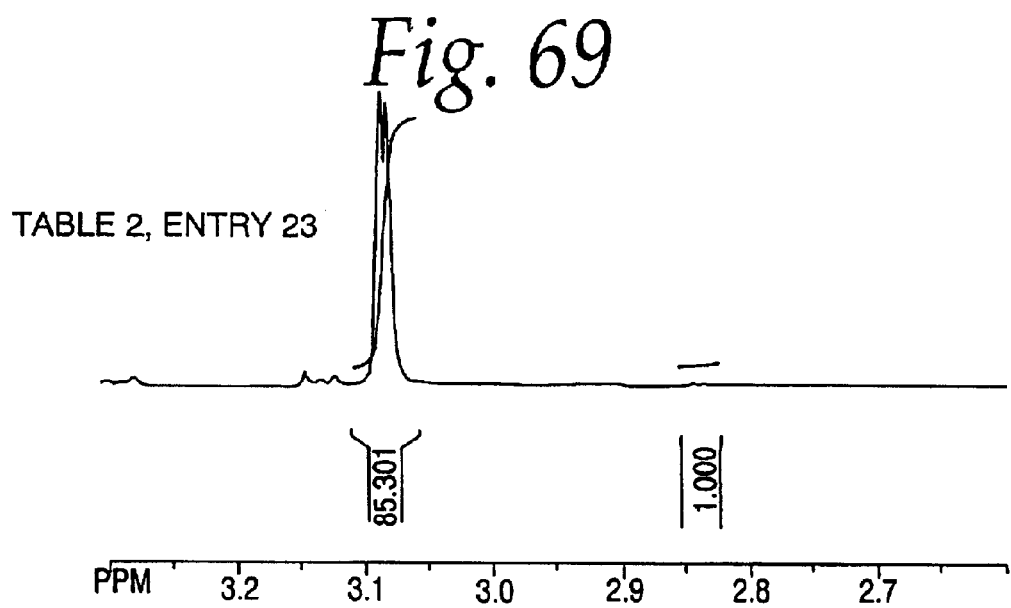
Figure 70:
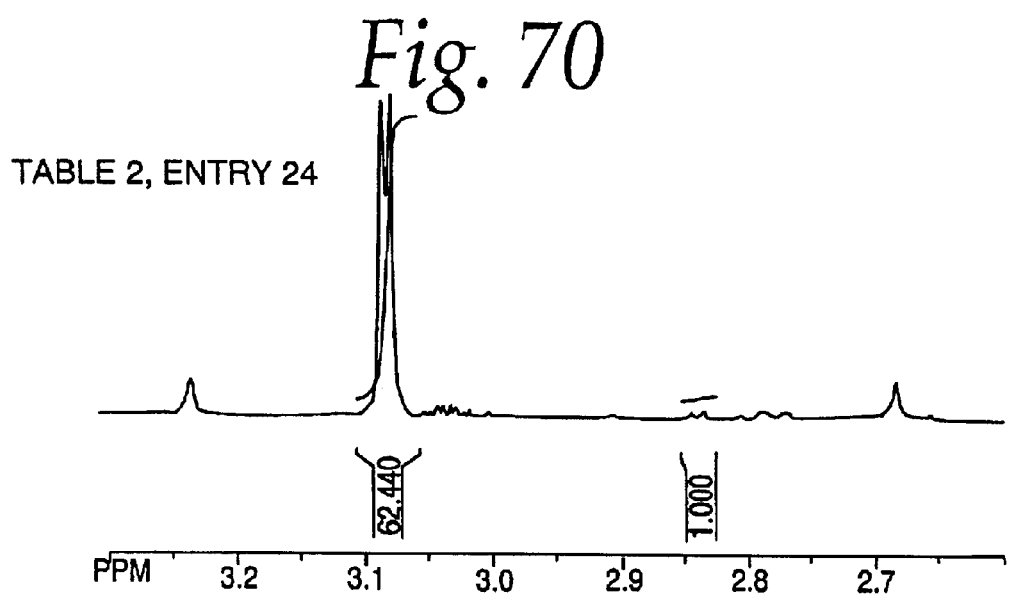

The $^1$H and $^{13}$C NMR spectra (FIGS. 4–70) were recorded in deuteriochloroform (CDCl$_3$) with tetramethylsilane (TMS) as internal standard at ambient temperature on a Bruker Avance DPX 300 or 500 Fourier Transform Spectrometer. Infrared absorption spectra were recorded as a solution in CH$_2$Cl$_2$ on a Bio-Rad FTS 165 Fourier Transform Spectrophotometer. Mass spectra were recorded with a Finningan MAT 95 mass spectrometer for both low resolution and high resolution mass spectra.

Substrates 5, 6, 8, 9, ketone 1, tetrahydrothiopyran-4-one (precursor of ketone 2), and Oxone® were purchased from Aldrich or Acros Chemical Co. and used without further purification. Substrates 7, 10, 11, 12, 13–20, and ketones 3, 4 were prepared according to the literature procedures.

Typical Procedure for in situ Epoxidation Reactions

Epoxidation of Cholesterol 5 Catalyzed by Ketone 4 (Table 1, Entry 4). To a solution of cholesterol 5 (116 mg 0.3 mmol) and ketone 4 (41 mg, 0.09 mmol) in dimethoxymethane (DMM, 9 mL) and acetonitrile (CH$_3$CN, 3 mL) at room temperature was added an aqueous Na$_2$·EDTA solution (6 mL, 4×10$^{-4}$ M). To this mixture was added in portions a mixture of Oxone® (922 mg, 1.5 mmol) and sodium bicarbonate (391 mg, 4.65 mmol) over the reaction period. The reaction mixture was poured into water, and extracted with ethyl acetate three times. The combined organic layers were dried over anhydrous MgSO$_4$ and filtered through a pad of silica gel. The ratio of α/β-epoxides was determined by $^1$H NMR analysis of the crude residue which was obtained after removal of the solvent under reduced pressure. Pure products were obtained after flash column chromatography on silica gel (99 mg, 82% yield).

Epoxidation of Substrate 13 Catalyzed by Ketone 2 (Table 2, Entry 8). To a solution of substrate 13 (112 mg 0.3 mmol) and tetrahydrothiopyran-4-one (1.7 mg, 0.015 mmol) in dimethoxymethane (DMM, 9 mL) and acetonitrile (CH$_3$CN, 3 mL) at room temperature was added an aqueous Na$_2$·EDTA solution (6 mL, 4×10$^{-4}$ M). To this mixture was added in portions a mixture of Oxone® (922 mg, 1.5 mmol) and sodium bicarbonate (391 mg, 4.65 mmol) over a period of 1.5 h. The reaction was complete in 2 h as shown by TLC. The reaction mixture was poured into water, and extracted with ethyl acetate three times. The combined organic layers were dried over anhydrous MgSO$_4$ and filtered through a pad of silica gel. The ratio of α/β-epoxides was determined by $^1$H NMR analysis of the crude residue which was obtained after removal of the solvent under reduced pressure. Pure epoxide was obtained after flash column chromatography on silica gel (110 mg, 94% yield).

Procedure for Preparative Scale Epoxidation Reactions

Epoxidation of Substrate 9 Catalyzed by Ketone 4 (Table 1, Entry 9). To a solution of substrate 9 (3.17 g 10 mmol) and ketone 4 (1.37 g, 3 mmol) in dimethoxymethane (DMM, 300 mL) and acetonitrile (CH$_3$CN, 100 mL) at room temperature was added an aqueous Na$_2$.EDTA solution (200 mL, 4×10$^{-4}$ M). To this mixture was added in portions a mixture of Oxone® (30.74 g, 50 mmol) and sodium bicarbonate (13.02 g, 155 mmol) over a period of 8 h. The reaction was complete in 10 h as shown by TLC. The reaction mixture was poured into water, and extracted with ethyl acetate three times. The combined organic layers were dried over anhydrous MgSO$_4$ and filtered through a pad of silica gel. The ratio of α/β-epoxides was determined by $^1$H NMR analysis of the crude residue which was obtained after removal of the solvent under reduced pressure. Pure products were obtained after flash column chromatography on silica gel (2.86 g, 86% yield).

Epoxidation of Substrate 18 Catalyzed by Ketone 2 (Table 2, Entry 19). To a solution of substrate 18 (4.03 g 10 mmol) and tetrahydrothiopyran-4-one (58 mg, 0.5 mmol) in dimethoxymethane (DMM, 300 mL) and acetonitrile (CH$_3$CN, 100 mL) at room temperature was added an aqueous Na$_2$.EDTA solution (200 mL, 4×10$^{-4}$ M). To this mixture was added in portions a mixture of Oxone® (30.74 mg, 50 mmol) and sodium bicarbonate (13.02 g, 155 mmol) over a period of 4 h. The reaction was complete in 5 h as shown by TLC. The reaction mixture was poured into water, and extracted with ethyl acetate three times. The combined organic layers were dried over anhydrous MgSO$_4$ and filtered through a pad of silica gel. The ratio of α/β-epoxides was determined by $^1$H NMR analysis of the crude residue which was obtained after removal of the solvent under reduced pressure. Pure epoxide was obtained after flash column chromatography on silica gel (3.68 g, 88% yield).

General Procedure for Epoxidation of Δ$^5$-Unsaturated Steroids with mCPBA

Sodium bicarbonate (0.4 mmol) and mCPBA (0.2 mmol) were added to a solution of substrate (0.1 mmol) in CH$_2$Cl$_2$ (3 ml). The resulting mixture was stirred at room temperature for 2 h and quenched with a solution of saturated aqueous Na$_2$S$_2$O$_3$. The reaction mixture was diluted with ethyl acetate and washed with a solution of saturated aqueous NaHCO$_3$ and brine. The organic layer was dried over anhydrous MgSO$_4$ and filtered through a pad of silica gel. The product analysis was performed as above.

Characterization Data for Epoxides

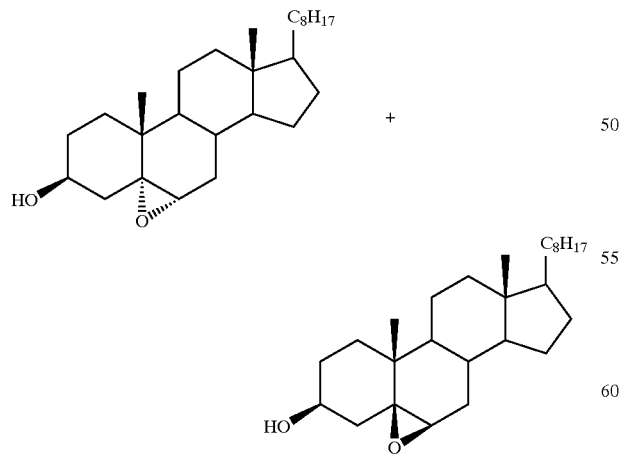

5a and 5b (as a mixture of 1:15.1 ratio; Table 1, Entry 4):
$^1$H NMR (300 MHz, CDCl$_3$) δ3.94–3.86 (m, 1/16.1×1H, 3α-H), 3.74–3.64 (m, 15.1/16.1×1H, 3α-H), 3.06 (d, J=2.2 Hz, 15.1/16.1×1H, 6α-H), 2.90 (d, J=4.3 Hz, 1/16.1×1H, 6β-H), 1.06 (s, 1/16.1×3H, 19-CH$_3$), 0.99 (s, 15.1/16.1×3H, 19-CH$_3$), 0.89 (d, J=6.6 Hz, 15.1/16.1×3H, 21-CH$_3$), 0.86 (d, J=6.6 Hz, 15.1/16.1×6H, 26-CH$_3$ and 27CH$_3$), 0.64 (s, 15.1/16.1×3H, 18-CH$_3$), 0.61 (s, 1/16.1×3H, 18-CH$_3$); $^{13}$C NMR of 5b (75.5 MHz, CDCl$_3$) δ69.32, 63.76, 63.04, 56.21, 56.20, 51.32, 42.27, 42.18, 39.82, 39.48, 37.22, 36.12, 35.71, 34.84, 32.59, 30.97, 29.76, 28.14, 27.99, 24.18, 23.80, 22.81, 22.55, 21.98, 18.66, 17.05, 11.75.

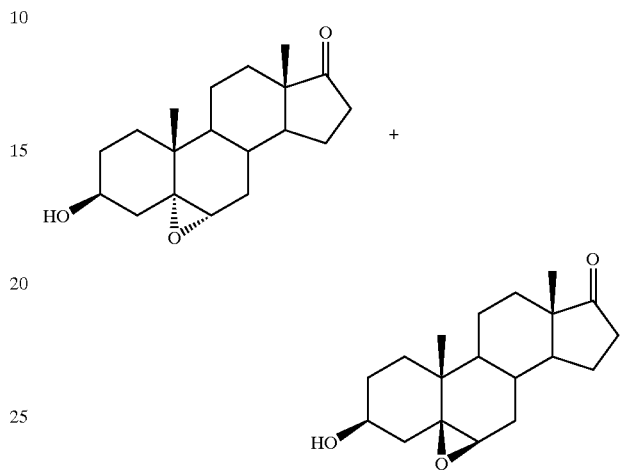

6a and 6b (as a mixture of 1:10.4 ratio; Table 1, Entry 5):
$^1$H NMR (300 MHz, CDCl$_3$) δ3.95–3.85 (m, 1/11.4×1H, 3α-H), 3.76–3.65 (m, 10.4/11.4×1H, 3α-H), 3.13 (d, J=2.5 Hz, 10.4/11.4×1H, 6α-H), 2.95 (d, J=4.3 Hz, 1/11.4×1H, 6β-H), 1.09 (s, 1/11.4×3H, 19-CH$_3$), 1.03 (s, 10.4/11.4×3H, 19-CH$_3$), 0.85 (s, 10.4/11.4×3H, 18-CH$_3$) 0.82 (s, 1/11.4×3H, 18-CH$_3$); $^{13}$C NMR of 6b (75.5 MHz, CDCl$_3$) δ220.97, 69.21 63.32, 63.05, 51.47, 51.18, 47.49, 42.05, 37.24, 35.74, 35.10, 31.51, 31.46, 30.93, 29.47, 21.73, 21.28, 17.08, 13.47.

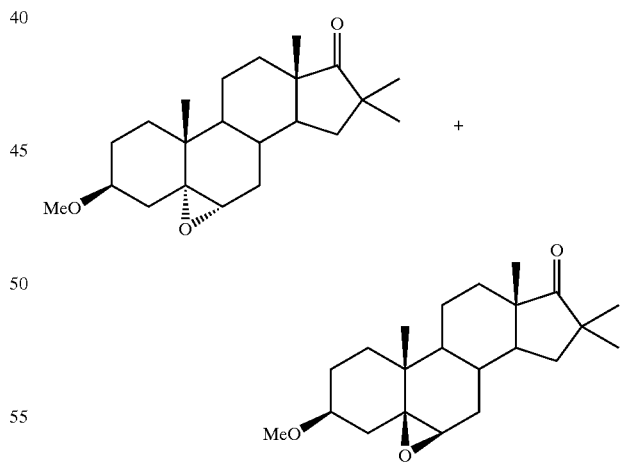

7a and 7b (as a mixture of 1:9; Table 1, Entry 6):
$^1$H NMR (500 MHz, CDCl$_3$) δ=3.45–3.38 (m, 1/10×1H, 3α-H), 3.34 (s, 3H, OCH$_3$) 3.28–3.22 (m, 9/10×1H, 3α-H), 3.11 (d, J=2.4 Hz, 9/10×1H, 6α-H), 2.95 (d, J=4.4 Hz, 1/10×1H, 6β-H), 1.18 (s, 9/10×3H, 19-CH$_3$), 1.17 (s, 1/10×3H, 19-CH$_3$), 1.02 (s, 9/10×6H, 20-CH$_3$ and 21-CH$_3$), 0.87 (s, 9/10×3H, 18-CH$_3$), 0.85 (s, 1/10×3H, 18-CH$_3$); $^{13}$C NMR of 9b (75.5 MHz, CDCl$_3$) δ=225.00, 77.70, 63.15, 63.04, 55.71, 51.37, 48.52, 48.01, 45.15, 38.63, 37.82, 36.75, 35.54, 32.30, 31.66, 28.93, 27.27, 27.02, 25.95, 21.08, 17.13, 14.08; IR (CH$_2$Cl$_2$) 1730 cm$^{-1}$; LRMS (EI, 20 eV) m/z 346 (100), 314 (15), 123 (31), 108 (22); HRMS (EI, 20 eV) calcd for C$_{22}$H$_{34}$O$_3$ (M$^+$): 346.2508, found: 346.2508; Anal. Calcd for C$_{22}$H$_{34}$O$_3$: C, 76.26; H, 9.89; Found: C, 76.14; H, 9.90.

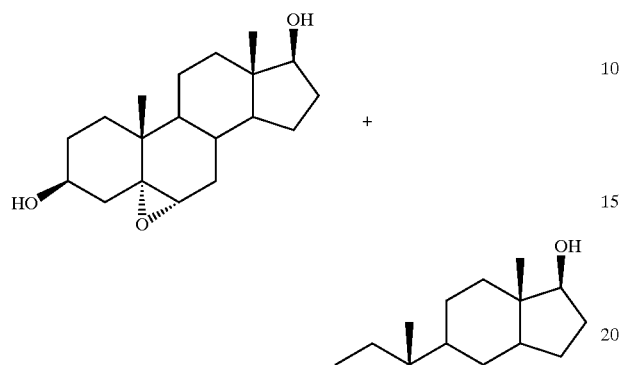

8a and 8b (as a mixture of 1:8.8 ratio; Table 1, Entry 7):

$^1$H NMR (300 MHz, CDCl$_3$) δ3.95–3.84 (m, 1/9.8×1H, 3α-H), 3.74–3.64 (m, 8.8/9.8×1H, 3α-H), 3.60 (t, J=8.5 Hz, 1H, 17α-H), 3.07 (d, J=2.4 Hz, 8.8/9.8×1H, 6α-H), 2.91 (d, J=4.4 Hz, 1/9.8×1H, 6β-H), 1.07 (s, 1/9.8×3H, 19-CH$_3$), 1.01 (s, 8.8/9.8×3H, 19-CH$_3$), 0.72 (s, 8.8/9.8×3H, 18-CH$_3$), 0.69 (s, 1/9.8×3H, 18-CH$_3$); $^{13}$C NMR of 8b (75.5 MHz, CDCl$_3$) δ81.81, 69.31, 63.51, 63.01, 51.48, 50.74, 42.67, 42.15, 37.25, 36.62, 34.99, 32.19, 30.97, 30.42, 29.81, 23.31, 21.60, 17.12, 10.86.

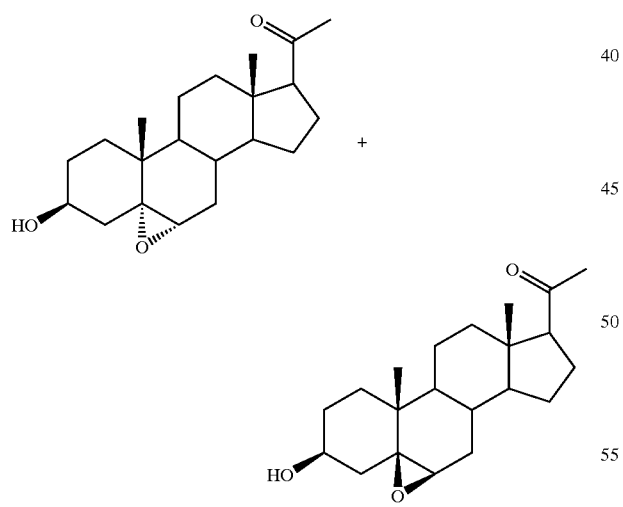

9a and 9b (as a mixture of 1:11.6; Table 1, Entry 8):

$^1$H NMR (300 MHz, CDCl$_3$) δ3.94–3.87 (m, 1/12.6×1H, 3α-H), 3.75–3.65 (m, 11.6/12.6×1H, 3α-H), 3.08 (d, J=2.3 Hz, 11.6/12.6×1H, 6α-H), 2.92 (d, J=4.4 Hz, 1/12.6×1H, 6β-H), 2.11 (s, 11.6/12.6×3H, 21-CH$_3$) 1.06 (s, 1/12.6×3H, 19-CH$_3$), 1.00 (s, 11.6/12.6×3H, 19-CH$_3$), 0.59 (s, 11.6/12.6×3H, 18-CH$_3$) 0.56 (s, 1/12.6×3H, 18-CH$_3$); $^{13}$C NMR of 9b (75.5 MHz, CDCl$_3$) δ209.48, 69.29, 63.67, 63.50, 62.89, 56.33, 51.19, 43.89, 42.12, 38.84, 4.92, 32.51, 31.46, 30.97, 29.76, 24.36, 22.77, 21.96, 17.07, 13.11.

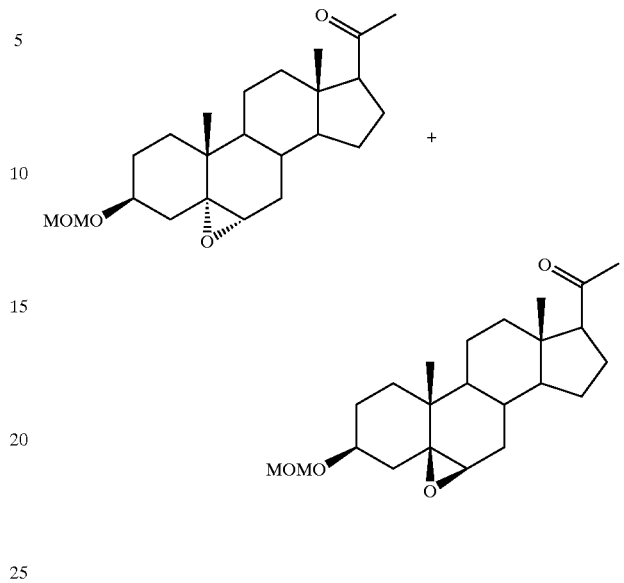

10a and 10b (as a mixture of: 18.5; Table 1, Entry 10):

$^1$H NMR (300 MHz, CDCl$_3$) δ4.73–4.64 (m, 2H, OCH$_2$O), 3.83–3.74 (m, 1/9.5×1H, 3α-H), 3.65–3.55 (m, 8.5/9.5×1H, 3α-H), 3.36 (s, 8.5/9.5×3H, OCH$_3$), 3.35 (s, 1/9.5×3H, OCH$_3$), 3.08 (d, J=2.3 Hz, 8.5/9.5×1H, 6α-H), 2.91 (d, J=4.3 Hz, 1/9.5×1H, 6α-H), 2.11 (s, 8.5/9.5×3H, 21-CH$_3$), 1.06 (s, 1/9.5×3H, 19-CH$_3$), 1.00 (s, 8.5/9.5×3H, 19-CH$_3$), 0.60 (s, 8.5/9.5×3H, 18-CH$_3$), 0.56 (s, 1/9.5×3H, 18-CH$_3$); $^{13}$C NMR of 11b (75.5 MHz, CDCl$_3$) δ209.35, 94.67, 74.18, 63.67, 63.44, 62.82, 56.33, 55.26, 51.08, 43.88, 39.43, 38.84, 37.07, 35.16, 32.48, 31.45, 29.74, 28.13, 24.35, 22.77, 21.94, 17.07, 13.11; IR (CH$_2$Cl$_2$) 1700 cm$^{-1}$; EIMS (20 eV) m/z 376 (100), 314 (90), 133 (36), 95 (33); HRMS (EI, 20 eV) calcd for C$_{23}$H$_{36}$O$_4$ (M$^+$): 376.2614, found: 376.2617; Anal. Calcd for C$_{23}$H$_{36}$O$_4$: C, 73.37; H, 9.64; Found: C, 73.11; H, 9.68.

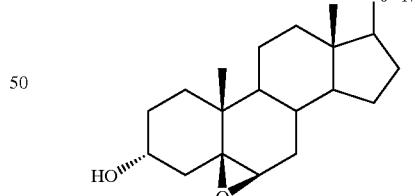

11b:

$^1$H NMR (300 MHz, CDCl$_3$) δ4.19 (br s, 1H, 3α-H), 3.07 (d, J=2.0 Hz, 1H, 6α-H), 0.97 (s, 3H, 19-CH$_3$), 0.89 (d, J=6.6 Hz, 3H, 21-CH$_3$), 0.86 (d, J=6.6 Hz, 6H, 26-CH$_3$ and 27-CH$_3$), 0.64 (s, 3H, 18-CH$_3$); $^{13}$C NMR (75.5 MHz, CDCl$_3$) δ67.03, 63.70, 61.97, 56.31, 56.20, 50.38, 42.31, 39.87, 39.86, 39.49, 36.14, 35.74, 35.53, 33.19, 32.37, 29.82, 28.40, 28.17, 27.99, 24.18, 23.83, 22.81, 22.55, 21.69, 18.67, 17.00, 11.78.

62.76, 49.81, 49.53, 45.50, 41.29, 35.43, 34.97, 33.91, 31.44, 30.64, 30.38, 29.78, 22.44, 21.20, 16.94, 13.96.

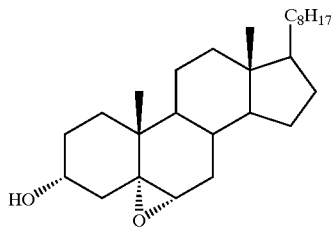

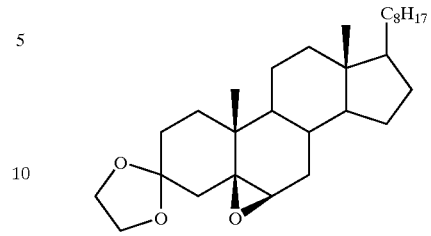

11a:

¹H NMR (300 MHz, CDCl₃) δ4.10–4.07 (m, 1H, 3β-H), 2.87 (d, J=4.5 Hz, 1H, 6β-H), 1.04 (s, 3H, 19-CH₃), 0.89 (d, J=6.6 Hz, 3H, 21-CH₃), 0.86 (d, J=6.6 Hz, 6H, 26-CH₃ and 27-CH₃), 0.61 (s, 3H, 18-CH₃); ¹³C NMR (75.5 MHz, CDCl₃) δ67.98, 65.43, 57.79, 56.86, 55.84, 42.66, 42.32, 39.49, 39.36, 36.41, 36.13, 35.76, 35.52, 29.62, 28.92, 28.63, 28.59, 28.07, 28.00, 24.02, 23.84, 22.82, 22.56, 20.28, 18.64, 15.34, 11.86.

14b:

¹H NMR (300 MHz, CDCl₃) δ3.97–3.85 (m, 4H, OCH₂CH₂O), 3.05 (d, J=1.9 Hz, 1H, 6α-H), 0.99 (s, 3H, 19-CH₃), 0.89 (d, J=6.7 Hz, 3H, 21-CH₃), 0.86 (d, J=6.6 Hz, 6H, 26-CH₃ and 27-CH₃), 0.64 (s, 3H, 18-CH₃); ¹³C NMR (75.5 MHz, CDCl₃) δ109.45, 64.27, 64.09, 63.29, 56.24, 56.15, 49.85, 42.28, 41.46, 39.81, 39.47, 36.11, 35.71, 35.61, 35.01, 32.27, 30.82, 29.67, 28.15, 27.98, 24.16, 23.79, 22.81, 22.54, 21.89, 18.66, 17.06, 11.75.

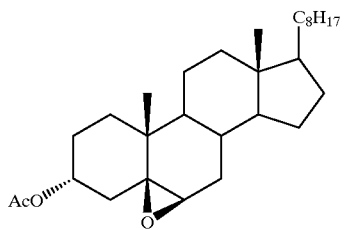

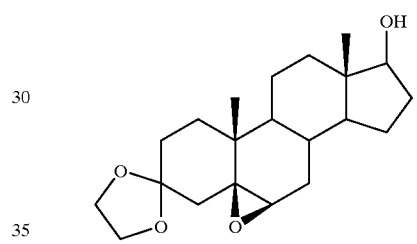

12b:

¹H NMR (300 MHz, CDCl₃) δ5.12–5.10 (m, 1H, 3β-H), 3.00 (d, J=2.0 Hz, 1H, 6α-H), 2.04 (s, 3H, CH₃COO), 0.99 (s, 3H, 19-CH₃), 0.89 (d, J=6.6 Hz, 3H, 21-CH₃), 0.86 (d, J=6.6 Hz, 6H, 26-CH₃ and 27-CH₃), 0.65 (s, 3H, 18-CH₃); ¹³C NMR (75.5 MHz, CDCl₃) δ170.52, 70.50, 63.28, 61.69, 56.33, 56.27, 50.20, 42.34, 39.86, 39.49, 36.63, 36.15, 35.76, 35.43, 33.78, 32.43, 29.81, 28.19, 28.01, 25.47, 24.19, 23.85, 22.82, 22.56, 21.71, 21.34, 18.68, 17.13, 11.78.

15b:

¹H NMR (300 MHz, CDCl₃) δ3.97–3.87 (m, 4H, OCH₂CH₂O), 3.60 (t, J=8.5 Hz, 1H, 17α-H), 3.07 (d, J=2.2 Hz, 1H, 6α-H), 1.01 (s, 3H, 19-CH₃), 0.72 (s, 3H, 18-CH₃); ¹³C NMR (75.5 MHz, CDCl₃) δ109.41, 81.78, 64.31, 64.14, 63.14, 63.05, 50.79, 50.07, 42.70, 41.45, 36.63, 35.66, 35.17, 31.87, 30.81, 30.45, 29.73, 23.31, 21.53, 17.14, 10.88.

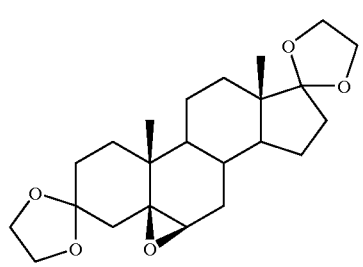

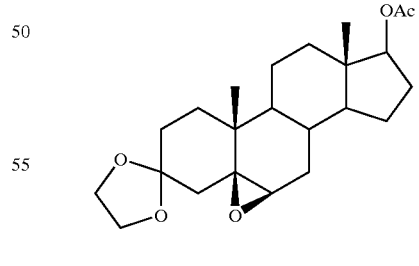

13b:

¹H NMR (300 MHz, CDCl₃) δ3.97–3.79 (m, 8H, OCH₂CH₂O), 3.06 (d, J=2.1 Hz, 1H, 6α-H), 1.00 (s, 3H, 19-CH₃), 0.82 (s, 3H, 18-CH₃); ¹³C NMR (75.5 MHz, CDCl₃) δ119.12, 109.19, 64.97, 64.33, 64.12, 63.94, 62.90,

16b:

¹H NMR (300 MHz, CDCl₃) δ4.56 (dd, J=9.0, 7.9 Hz, 1H, 17α-H), 3.95–3.89 (m, 4H, OCH₂CH₂O), 3.07 (d, J=2.2 Hz, 1H, 6α-H), 2.03 (s, 3H, CH₃COO), 1.00 (s, 3H, 19-CH₃), 0.77 (s, 3H, 18-CH₃); ¹³C NMR (75.5 MHz, CDCl₃) δ171.20, 109.34, 82.64, 64.30, 64.14, 63.09, 63.00 50.53, 49.94, 42.33, 41.45, 36.79, 35.68, 35.14, 31.85, 30.78, 29.52, 27.43, 23.44, 21.39, 21.15, 17.11, 11.84.

50.60, 42.45, 41.81, 37.41, 35.87, 31.40, 30.57, 27.91, 24.40, 23.42, 22.97, 15.55, 13.86.

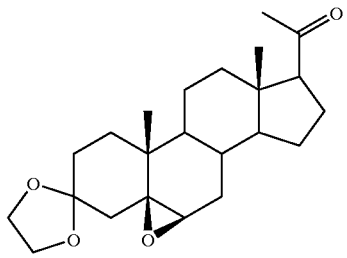

17b:

$^1$H NMR (300 MHz, CDCl$_3$) δ3.95–3.90 (m, 4H, OCH$_2$CH$_2$O), 3.07 (d, J=2.1 Hz, 1H, 6α-H), 2.11 (s, 3H, 21-CH$_3$), 1.00 (s, 3H, 19-CH$_3$), 0.60 (s, 3H, 18-CH$_3$); $^{13}$C NMR (75.5 MHz, CDCl$_3$) δ209.41, 109.37, 64.33, 64.16, 63.66, 63.15, 62.95, 56.40, 49.84, 43.92, 41.42, 38.85, 35.71, 35.10, 32.21, 31.47, 30.82, 29.70, 24.36, 22.78, 21.90, 17.09, 13.12.

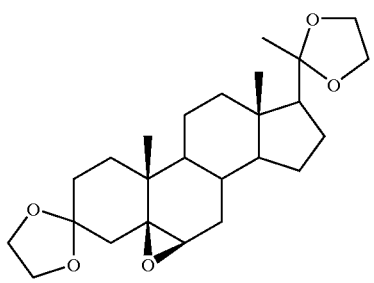

18b:

$^1$H NMR (300 MHz, CDCl$_3$) δ4.04–3.81 (m, 8H, OCH$_2$CH$_2$O), 3.06 (d, J=1.8 Hz, 1H, 6α-H),1.28 (s, 3H, 21-CH$_3$), 1.00 (s, 3H, 19-CH$_3$), 0.74 (s, 3H, 18-CH$_3$); $^{13}$-C NMR (75.5 MHz, CDCl$_3$) δ111.85, 109.44, 65.16, 64.29, 64.12, 63.26, 63.19, 63.00, 58.21, 56.12, 49.87, 41.75, 9.44, 35.62, 35.06, 32.18, 30.82, 29.22, 24.54, 23.70, 22.90, 21.67, 17.10, 12.76.

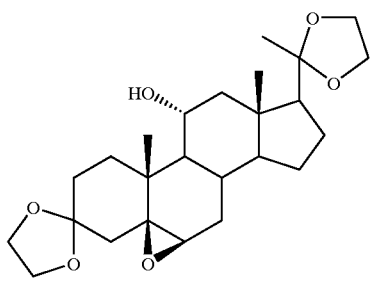

19b:

$^1$H NMR (300 MHz, CDCl$_3$) δ4.03–3.81 (m, 9H, 11β-H and OCH$_2$CH$_2$O), 3.08 (d, J=2.6 Hz1H, 6α-H), 1.28 (s, 3H, 21-CH$_3$), 1.20 (s, 3H, 19-CH$_3$), 0.76 (s, 3H, 18-CH$_3$); $^{13}$C NMR (75.5 MHz, CDCl$_3$) δ111.47, 109.02, 68.68, 64.98, 64.17, 64.04, 63.35, 63.10, 62.90, 57.80, 57.01, 55.22,

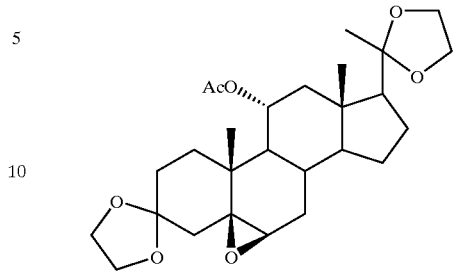

20b:

$^1$H NMR (300 MHz, CDCl$_3$) δ5.07 (td, J=10.9, 4.8 Hz, 1H, 11β-H), 3.99–3.83 (m, 8H, OCH$_2$CH$_2$O), 3.08 (d, J=2.7 Hz, 1H, 6α-H), 2.01 (s, 3H, CH$_3$COO), 1.24 (s, 3H, 21-CH$_3$), 1.02 (s, 3H, 19-CH$_3$), 0.82 (s, 3H, 18-CH$_3$); $^{13}$C NMR (75.5 MHz, CDCl$_3$) δ169.76, 111.42, 108.87, 72.38, 64.96, 64.28, 64.17, 63.16, 63.02, 62.69, 57.73, 55.09, 53.57, 45.36, 42.23, 41.86, 37.02, 35.85, 31.56, 30.70, 28.09, 24.46, 23.52, 23.19, 21.87, 16.06, 13.58.

Determination of the Ratio of β/α-epoxides

The ratio of β/α-epoxides was determined by integration of the C(6) proton signals in the $^1$H NMR spetra (300 or 500 MHz) of crude residues (δ3.00–3.15 ppm for β-epoxides and δ 2.75–2.95 ppm for α-epoxides). The authentic samples of 5a/5b–20a/20b were prepared by epoxidation of substrates 5–20 with mCPBA according to the literature procedure.

EXAMPLES

Example 1

5β,6β-Epoxycholestan-3β-ol (Catalyzed by Ketone 4)

To a solution of cholesterol (116 mg 0.3 mmol) and ketone 4 (41 mg, 0.09 mmol) in dimethoxymethane (9 mL) and acetonitrile (3 mL) at room temperature was added an aqueous Na$_2$.EDTA solution (6 mL, 4×10$^{-4}$ M). To this mixture was added in portions a mixture of Oxone® (922 mg, 1.5 mmol) and sodium bicarbonate (391 mg, 4.65 mmol) over the reaction period. The reaction mixture was poured into water, and extracted with ethyl acetate three times. The combined organic layers were dried over anhydrous MgSO$_4$ and filtered through a pad of silica gel. $^1$H NMR analysis of the product showed that the ratio of β/α-epoxides was 15.1:1. Pure products were obtained after flash column chromatography on silica gel (99 mg, 82% yield).

Example 2

5β,6β-Epoxyandrostene-3,17-dione 3,17-diethylene Ketal (Catalyzed by Ketone 1)

To a solution of 5-androstene-3,17-dione 3,17-diethylene ketal (112 mg 0.3 mmol) in dimethoxymethane (9 mL) and acetonitrile (3 mL) was added an aqueous Na$_2$·EDTA solution (6 mL, 4×10$^{-4}$ M), the resulting solution was cooled to 0–1° C., followed by addition of 1,1,1-trifluoroacetone (0.54 mL, 6 mmol). To this solution was added in portions a mixture of Oxone® (922 mg, 1.5 mmol) and sodium bicarbonate (391 mg, 4.65 mmol) over a period of 0.5 h. The reaction was complete in 1 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the crude residue showed that the ratio of β/α-epoxides was >99:1. 5β,6β-Epoxyandrostene-3,17-dione 3,17-diethylene ketal was obtained after flash column chromatography on silica gel (101 mg, 86% yield).

Example 3

5β,6β-Epoxyandrostene-3,17-dione 3,17-diethylene Ketal (Catalyzed by Ketone 2)

To a solution of 5-androstene-3,17-dione 3,17-diethylene ketal (112 mg 0.3 mmol) and tetrahydrothiopyran-4-one (1.7 mg, 0.015 mmol) in dimethoxymethane (9 mL) and acetonitrile (3 mL) at room temperature was added an aqueous Na$_2$.EDTA solution (6 mL, 4×10$^{-4}$ M). To this mixture was added in portions a mixture of Oxone® (922 mg, 1.5 mmol) and sodium bicarbonate (391 mg, 4.65 mmol) over a period of 1.5 h. The reaction was complete in 2 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the crude residue showed that the ratio of β/α-epoxides was 96:1. 5β,6β-Epoxyandrostene-3,17-dione 3,17-diethylene ketal was obtained after flash column chromatography on silica gel (110 mg, 94% yield).

Example 4

5β,6β-Epoxyandrostene-3,17-dione 3,17-diethylene Ketal (Catalyzed by Ketone 3)

To a solution of 5-androstene-3,17-dione 3,17-diethylene ketal (112 mg 0.3 mmol) and ketone 3 (9 mg, 0.03 mmol) in dimethoxymethane (9 mL) and acetonitrile (3 mL) at room temperature was added an aqueous Na$_2$·EDTA solution (6 mL, 4×10$^{-4}$ M). To this mixture was added in portions a mixture of Oxone® (922 mg, 1.5 mmol) and sodium bicarbonate (391 mg, 4.65 mmol) over a period of 1 h. The reaction was complete in 1.5 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the crude residue showed that the ratio of β/α-epoxides was 49:1. 5β,6β-Epoxyandrostene-3,17-dione 3,17-diethylene ketal was obtained after flash column chromatography on silica gel (109 mg, 93% yield).

Example 5

5β,6β-Epoxyandrostene-3,17-dione 3,17-diethylene Ketal (Catalyzed by Acetone)

To a solution of 5-androstene-3,17-dione 3,17-diethylene ketal (112 mg 0.3 mmol) and acetone (522 mg, 9 mmol) in dimethoxymethane (9 mL) and acetonitrile (3 mL) at room temperature was added an aqueous Na$_2$·EDTA solution (6 mL, 4×10$^{-4}$ M). To this mixture was added in portions a mixture of Oxone® (922 mg, 1.5 mmol) and sodium bicarbonate (391 mg, 4.65 mmol) over a period of 4 h. The reaction was complete in 5 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the crude residue showed that the ratio of β/α-epoxides was >99:1. 5β,6β-Epoxyandrostene-3,17-dione 3,17-diethylene ketal was obtained after flash column chromatography on silica gel (110 mg, 94% yield).

Example 6

5β,6β-Epoxyandrostene-3,17-dione 3,17-diethylene Ketal (Acetone as Catalyst and Cosolvent)

To a solution of 5-androstene-3,17-dione 3,17-diethylene ketal (112 mg 0.3 mmol) in actone (15 mL) at room temperature was added an aqueous Na$_2$.EDTA solution (5 mL, 4×10$^{-4}$ M). To this mixture was added in portions a mixture of Oxone® (922 mg, 1.5 mmol) and sodium bicarbonate (391 mg, 4.65 mmol) over a period of 1.5 h. The reaction was complete in 2 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the crude residue showed that the ratio of β/α-epoxides was >99:1. 5β,6β-Epoxyandrostene-3,17-dione 3,17-diethylene ketal was obtained after flash column chromatography on silica gel (105 mg, 90% yield).

Example 7

5β,6β-Epoxy-3β-Hydroxypregnan-20-one (Catalyzed by Ketone 4)

To a solution of pregnenolone (3.17 g 10 mmol) and ketone 4 (1.37 g, 3 mmol) in dimethoxymethane (300 mL) and acetonitrile (100 mL) at room temperature was added an aqueous Na$_2$.EDTA solution (200 mL, 4×10$^{-4}$ M). To this mixture was added in portions a mixture of Oxone® (30.74 g, 50 mmol) and sodium bicarbonate (13.02 g, 155 mmol) over a period of 8 h. The reaction was complete in 10 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the product showed that the ratio of β/α-epoxides was 16.0:1. Pure products were obtained after flash column chromatography on silica gel (2.86 g, 86% yield).

Example 8

5β,6β-Epoxy-11α-hydroxypregnene-3,20-dione 3-diethylene Ketal (Catalyzed by Ketone 2)

To a solution of 5-pregnene-3,20-dione 3,20-diethylene ketal (4.03 g 10 mmol) and tetrahydrothiopyran-4-one (58 mg, 0.5 mmol) in dimethoxymethane (300 mL) and acetonitrile (100 mL) at room temperature was added an aqueous Na$_2$·EDTA solution (200 mL, 4×10$^{-4}$ M). To this mixture was added in portions a mixture of Oxone® (30.74 mg, 50 mmol) and sodium bicarbonate (13.02 g, 155 mmol) over a period of 4 h. The reaction was complete in 5 h as shown by TLC. The reaction mixture was poured into water, and extracted with ethyl acetate three times. The combined organic layers were dried over anhydrous MgSO$_4$ and filtered through a pad of silica gel. $^1$H NMR analysis of the crude residue showed that the ratio of β/α-epoxides was >99:1. 5β,6β-Epoxypregnene-3,20-dione 3,20-diethylene ketal was obtained after flash column chromatography on silica gel (3.68 g, 88% yield).

Example 9

5β,6β-Epoxy-3β-hydroxyandrostan-17-one (Catalyzed by Ketone 4)

Following the procedure of Example 1 above, dehydroisoandrosterone was epoxidized to 5β,6β-epoxy-3β-hydroxyandrostan-17-one.

Example 10

5β,6β-Epoxy-16,16-dimethyl-3β-methoxyandrostan-17-one (Catalyzed by Ketone 4)

Following the procedure of Example 1 above, 16,16-dimethyl-3β-methoxy-5-androsten-17-one was epoxidized to 5β,6β-epoxy-16,16-dimethyl-3β-methoxyandrostan-17-one.

Example 11

5β,6β-Epoxyandrostane-3β,17β-diol (Catalyzed by Ketone 4)

Following the procedure of Example 1 above, 5-androstene-3β,17β-diol was epoxidized to 5β,6β-epoxyandrostane-3β,17β-diol.

Example 12

5β,6β-Epoxy-3β-methoxymethoxypregnan-20-one (Catalyzed by Ketone 4)

Following the procedure of Example 1 above, 3β-methoxymethoxy-5-pregnen-20-one was epoxidized to 5β,6β-epoxy-3β-methoxymethoxypregnan-20-one.

Example 13

5β,6β-Epoxycholestan-3α-ol (Catalyzed by Ketone 4)

Following the procedure of Example 1 above, epicholesterol was epoxidized to 5β,6β-epoxycholestan-3α-ol.

Example 14

5β,6β-Epoxy-3β-acetoxycholestane (Catalyzed by Ketone 2)

Following the procedure of Example 3 above, 3α-acetoxycholest-5-ene was epoxidized to 5β,6β-epoxy-3α-acetoxycholestane.

Example 15

5β,6β-Epoxy-3α-acetoxycholestane (Catalyzed by Ketone 4)

Following the procedure of Example 1 above, 3α-acetoxycholest-5-ene was epoxidized to 5β,6β-epoxy-3α-acetoxycholestane.

Example 16

5β,6β-Epoxycholestane-3-one 3-ethylene Ketal (Catalyzed by Ketone 2)

Following the procedure of Example 3 above, 5-cholestene-3-one 3-ethylene ketal was epoxidized to 5β,6β-epoxycholestane-3-one 3-ethylene ketal.

Example 17

5β,6β-Epoxycholestane-3-one 3-ethylene Ketal (Catalyzed by Ketone 4)

Following the procedure of Example 1 above, 5-cholestene-3-one 3-ethylene ketal was epoxidized to 5β,6β-epoxycholestane-3-one 3-ethylene ketal.

Example 18

5β,6β-Epoxy-17β-hydroxyandrostan-3-one 3-ethylene Ketal (Catalyzed by Ketone 2)

Following the procedure of Example 3 above, 17β-hydroxyandrost-5-en-3-one 3-ethylene ketal was epoxidized to 5β,6β-epoxy-17β-hydroxyandrostan-3-one 3-ethylene ketal.

Example 19

5β,6β-Epoxy-17β-hydroxyandrostan-3-one 3-ethylene Ketal (Catalyzed by Ketone 4)

Following the procedure of Example 1 above, 17β-hydroxyandrost-5-en-3-one 3-ethylene ketal was epoxidized to 5β,6β-epoxy-17β-hydroxyandrostan-3-one 3-ethylene ketal.

Example 20

5β,6β-Epoxy-17β-acetoxyandrostan-3-one 3-ethylene Ketal (Catalyzed by Ketone 2)

Following the procedure of Example 3 above, 17β-acetoxyandrost-5-en-3-one 3-ethylene ketal was epoxidized to 5β,6β-epoxy-17β-acetoxyandrostan-3-one 3-ethylene ketal.

Example 21

5β,6β-Epoxy-17β-acetoxyandrostan-3-one 3-ethylene Ketal (Catalyzed by Ketone 4)

Following the procedure of Example 1 above, 17β-acetoxyandrost-5-en-3-one 3-ethylene ketal was epoxidized to 5β,6β-epoxy-17β-acetoxyandrostan-3-one 3-ethylene ketal.

Example 22

5β,6β-Epoxypregnene-3,20-dione 3,20-diethylene Ketal (Catalyzed by Ketone 2)

Following the procedure of Example 3 above, 5-pregnene-3,20-dione 3,20-diethylene ketal was epoxidized to 5β,6β-epoxypregnene-3,20-dione 3,20-diethylene ketal.

Example 23

5β,6β-Epoxypregnene-3,20-dione 3,20-diethylene Ketal (Catalyzed by Ketone 4)

Following the procedure of Example 1 above, 5-pregnene-3,20-dione 3,20-diethylene ketal was epoxidized to 5β,6β-epoxypregnene-3,20-dione 3,20-diethylene ketal.

Example 24

5β,6β-Epoxypregnene-3,20-dione 3-diethylene Ketal (Catalyzed by Ketone 2)

Following the procedure of Example 3 above, 5-pregnene-3,20-dione 3-ethylene ketal was epoxidized to 5β,6β-epoxypregnene-3,20-dione 3-ethylene ketal.

Example 25

5β,6β-Epoxypregnene-3,20-dione 3-diethylene Ketal (Catalyzed by Ketone 4)

Following the procedure of Example 1 above, 5-pregnene-3,20-dione 3-ethylene ketal was epoxidized to 5β,6β-epoxypregnene-3,20-dione 3-ethylene ketal.

Example 26

5β,6β-Epoxy-11α-hydroxypregnene-3,20-dione 3-diethylene Ketal (Catalyzed by Ketone 2)

Following the procedure of Example 3 above, 11α-hydroxy-5-pregnene-3,20-dione 3-ethylene ketal was epoxidized to 5β,6β-epoxy-11α-hydroxypregnene-3,20-dione 3-diethylene ketal.

Example 27

5β,6β-Epoxy-11α-hydroxypregnene-3,20-dione 3-diethylene Ketal (Catalyzed by Ketone 4)

Following the procedure of Example 1 above, 11α-hydroxy-5-pregnene-3,20-dione 3-ethylene ketal was epoxidzed to 5β,6β-epoxy-11α-hydroxypregnene-3,20-dione 3-diethylene ketal.

Example 28

5β,6β-Epoxy-11α-acetoxypregnene-3,20-dione 3-diethylene Ketal (Catalyzed by Ketone 2)

Following the procedure of Example 3 above, 11α-acetoxy-5-pregnene-3,20-dione 3-ethylene ketal was epoxidized to 5β,6β-epoxy-11α-acetoxypregnene-3,20-dione 3-diethylene ketal.

Example 29

5β,6β-Epoxy-11α-acetoxypregnene-3,20-dione 3-diethylene Ketal (Catalyzed by Ketone 4)

Following the procedure of Example 1 above, 11α-acetoxy-5-pregnene-3,20-dione 3-ethylene ketal was epoxidized to 5β,6β-epoxy-11α-acetoxypregnene-3,20-dione 3-diethylene ketal.

Example 30

5β,6β-Epoxycholestan-3α-ol (catalyzed by Ketone 1)

Following the procedure of Example 2 above, epicholesterol was epoxidized to 5β,6β-epoxycholestan-3α-ol.

Example 31

5β,6β-Epoxyandrostene-3,17-dione 3,17-diethylene Ketal (Catalyzed by Ketone 4)

Following the procedure of Example 1 above 5-cholestene-3-one 3-ethylene ketal was epoxidized to 5β,6β-epoxyandrostene-3,17-dione 3,17-diethylene ketal.

Example 32

5β,6β-Epoxycholestane-3-one 3-ethylene Ketal (Catalyzed by Acetone)

Following the procedure of Example 5 above, 5-cholestene-3-one 3-ethylene ketal was epoxidized to 5β,6β-epoxycholestane-3-one 3-ethylene ketal.

Example 33

5β,6β-Epoxy-17β-acetoxyandrostan-3-one 3-ethylene Ketal (Catalyzed by Acetone)

Following the procedure of Example 5 above, 17β-acetoxyandrost-5-en-3-one 3-ethylene ketal was epoxidized to 5β,6β-epoxy-17β-acetoxyandrostan-3-one 3-ethylene ketal.

Example 34

5β,6β-Epoxypregnene-3,20-dione 3-ethylene Ketal (Catalyzed by Ketone 2)

Following the procedure of Example 3 above, 5-pregnene-3,20-dione 3-ethylene ketal was epoxidized to 5β,6β-epoxypregnene-3,20-dione 3-ethylene ketal.

Example 35

5β,6β-Epoxypregnene-3,20-dione 3-ethylene Ketal (Catalyzed by Ketone 4)

Following the procedure of Example 1 above, 5-pregnene-3,20-dione 3-ethylene ketal was epoxidized to 5β,6β-epoxypregnene-3,20-dione 3-ethylene ketal.

Example 36

5β,6β-Epoxypregnene-3,20-dione 3,20-diethylene Ketal (Catalyzed by Acetone)

Following the procedure of Example 5 above, 5-pregnene-3,20-dione 3,20-diethylene ketal was epoxidized to 5β,6β-epoxypregnene-3,20-dione 3,20-diethylene ketal.

Example 37

5β,6,-Epoxy-11α-hyrdoxypregnene-3,20-dione 3,20-diethylene Ketal (Catalyzed by Acetone)

Following the procedure of Example 5 above, 11α-hyrdoxy-5-pregnene-3,20-dione 3,20-diethylene ketal was epoxidized to 5β,6β-epoxy-11α-hyrdoxypregnene-3,20-dione 3,20-diethylene ketal.

Example 38

5β,6β-Epoxy-11α-hyrdoxypregnene-3,20-dione 3, 20-diethylene Ketal (Catalyzed by Ketone 2)

Following the procedure of Example 3 above, 11α-hyrdoxy-5-pregnene-3,20-dione 3,20-diethylene ketal was epoxidized to 5β,6β-epoxy-11α-hyrdoxypregnene-3,20-dione 3,20-diethylene ketal.

Example 39

5β,6β-Epoxy-11α-hyrdoxypregnene-3,20-dione 3, 20-diethylene Ketal (Catalyzed by Ketone 4)

Following the procedure of Example 1 above, 11α-hyrdoxy-5-pregnene-3,20-dione 3,20-diethylene ketal was epoxidized to 5β,6β-epoxy-11α-hyrdoxypregnene-3,20-dione 3,20-diethylene ketal.

Example 40

5β,6β-Epoxy-11α-acetoxypregnene-3,20-dione 3, 20-diethylene Ketal (Catalyzed by Ketone 2)

Following the procedure of Example 3 above, 11α-acetoxy-5-pregnene-3,20-diethylene ketal was epoxidized to 5β,6β-epoxy-11α-acetoxypregnene-3,20-dione 3,20-diethylene ketal.

Example 41

5β,6β-Epoxy-11α-acetoxypregnene-3,20-dione 3, 20-diethylene Ketal (Catalyzed by Ketone 4)

Following the procedure of Example 1 above, 11α-acetoxy-5-pregnene-3,20-dione 3,20-diethylene ketal was epoxidized to 5β,6β-epoxy-11α-acetoxypregnene-3,20-dione 3,20-diethylene ketal.

The invention has been described with reference to preferred embodiments. Those skilled in the art will perceive improvements, changes and modifications. Such improvements, changes and modifications are intended to be within the scope of the claims.

TABLE 1

Stereoselective epoxidation of 3β-substituted Δ⁵-steroids by dioxiranes generated in situ[a]

| entry | ketone catalyst | substrate | catalyst loading (equivalent) | reaction time (h)[b] | yield (%)[c] | β/α-epoxide ratio[d,e] |
|---|---|---|---|---|---|---|
| 1 | 1[f] | 5 | 20 | 1.5 | 91 | 1/1.1 (1/4.0) |
| 2 | 2 | 5 | 0.05 | 1.5 | 93 | 1.1/1 |
| 3 | 3 | 5 | 0.1 | 3 | 92 | 1/1.1 |
| 4 | 4 | 5 | 0.3 | 16 | 82 | 15.1/1 |
| 5 | 4 | 6 | 0.2 | 9 | 91 | 10.4/1 (1/3.9) |
| 6 | 4 | 7 | 0.2 | 20 | 88 | 9.0/1 (1/3.1) |
| 7 | 4 | 8 | 0.2 | 16 | 85 | 8.8/1 (1/3.1) |
| 8 | 4 | 9 | 0.2 | 9 | 93 | 11.6/1 (1/4.3) |
| 9[g] | 4 | 9 | 0.3 | 10 | 86 | 16.0/1 |
| 10 | 4 | 10 | 0.2 | 20 | 83 | 8.5/1 (1/3.7) |

[a]Unless otherwise indicated, reaction conditions were as follows: room temperature, 0.3 mmol of substrate, indicated amount of ketone, 1.5 mmol of Oxone ®, 4.65 mmol of $NaHCO_3$, 9 mL of dimethoxymethane (DMM), 3 mL of $CH_3CN$, and 6 mL of aqueous $Na_2.EDTA$ solution ($4 \times 10^{-4}$ M).
[b]Time for complete epoxidation as shown by TLC.
[c]Isolated yield.
[d]The ratio of β/α-epoxides was determined by $^1$H NMR spectroscopy (500 or 300 MHz).
[e]The value in parentheses was the ratio of β/α-epoxides obtained with mCPBA as the oxidant.
[f]The epoxidation reaction was carried out at 0–1° C.
[g]On a 10 mmol scale.

Note

An additional experiment was performed using ketone 4 and substrate 9 in which the catalyst loading and reaction time were 0.2 and 12 h, respectively. The subsequent epoxidation reaction resulted in an 89% yield and a β/α-epoxide ratio of 11.4/1.

TABLE 2

Stereoselective epoxidation of 3α-substituted Δ⁵-steroids by dioxiranes generated in situ[a]

| entry | ketone | substrate | catalyst loading (equivalent) | reaction time (h)[b] | yield (%)[c] | β/α-epoxide ratio[d,e] |
|---|---|---|---|---|---|---|
| 1 | 1[f] | 11 | 20 | 2 | 90 | 19:1 |
| 2 | 2 | 11 | 0.05 | 2 | 93 | 5:1 |
| 3 | 3 | 11 | 0.1 | 3.5 | 91 | 4:1 |
| 4 | 4 | 11 | 0.2 | 8 | 92 | 90:1 |
| 5 | 2 | 12 | 0.05 | 4 | 82 | 72:1(2:1) |
| 6 | 4 | 12 | 0.3 | 18 | 84[g] | >99:1 |
| 7 | 1[e] | 13 | 20 | 1 | 86 | >99:1 |
| 8 | 2 | 13 | 0.05 | 2 | 94 | 96:1 |
| 9 | 3 | 13 | 0.1 | 1.5 | 93 | 49:1 |
| 10 | 4 | 13 | 0.3 | 12 | 84 | >99:1 |
| 11 | 2 | 14 | 0.05 | 3.5 | 95 | >99:1 |
| 12 | 4 | 14 | 0.3 | 18 | 86[h] | >99:1 |
| 13 | 2 | 15 | 0.05 | 2 | 88 | 79:1 (1:1) |
| 14 | 4 | 15 | 0.2 | 10 | 83 | 86:1 |
| 15 | 2 | 16 | 0.05 | 3 | 95 | 91:1 |
| 16 | 4 | 16 | 0.2 | 12 | 82 | >99:1 |
| 17 | 2 | 17 | 0.05 | 1 | 91 | 84:1 (1:1) |
| 18 | 4 | 17 | 0.2 | 15 | 81 | 66:1 |
| 19 | 2 | 18 | 0.05 | 3.5 | 96 | 92:1 |
| 20 | 4 | 18 | 0.2 | 12 | 84 | 61:1 |
| 21 | 2 | 19 | 0.05 | 2 | 92 | 51:1 |
| 22 | 4 | 19 | 0.2 | 9 | 91 | 50:1 |
| 23 | 2 | 20 | 0.05 | 2 | 92 | 85:1(1:1) |
| 24 | 4 | 20 | 0.3 | 12 | 82 | 62:1 |

[a]Unless otherwise indicated, reaction conditions were as follows: room temperature, 0.3 mmol of substrate, indicated amount of ketone, 1.5 mmol of Oxone ®, 4.65 mmol of $NaHCO_3$, 9 mL of dimethoxymethane (DMM), 3 mL of $CH_3CN$, and 6 mL of aqueous $Na_2.EDTA$ solution ($4 \times 10^{-4}$ M).
[b]Time for complete epoxidation as shown by TLC.
[c]Isolated yield unless otherwise noted.
[d]The ratio of β/α-epoxides was determined by $^1$H NMR spectroscopy (500 or 300 MHz).
[e]The value in parentheses was the ratio of β/α-epoxides obtained with mCPBA as the oxidant.
[f]The epoxidation reaction was carried out at 0–1° C.
[g]Based on recovered starting material (82% conversion).
[h]Based on recovered starting material (61% conversion).

TABLE 3

Stereoselective epoxidation of 3α-substituted Δ⁵-steroids catalyzed by acetone.

| Entry | substrate | catalyst loading (equivalent) | reaction time (h)[b] | yield (%)[c] | β/α-epoxide ratio[d,e] |
|---|---|---|---|---|---|
| 1 | 11 | 20 | 5 | 90 | 3:1 (1:9.5) |
| 2 | 13 | 20 | 5 | 94 | >99:1[f] (1:1) |
| 3 | 14 | 20 | 6 | 93 | >99:1 (1:1) |
| 4 | 16 | 20 | 3.5 | 93 | >99:1 (1:1) |
| 5 | 18 | 20 | 6 | 92 | >99:1 (1:1) |
| 6 | 19 | 20 | 5 | 91 | 43:1 (1:1) |

[a]Unless otherwise indicated, reaction conditions were as follows: room temperature, 0.3 mmol of substrate, indicated amount of ketone, 1.5 mmol of Oxone ®, 4.65 mmol of $NaHCO_3$, 9 mL of dimethoxymethane (DMM), 3 mL of $CH_3CN$, and 6 mL of aqueous $Na_2.EDTA$ solution ($4 \times 10^{-4}$ M).
[b]Time for complete epoxidation as shown by TLC.
[c]Isolated yield.
[d]The ratio of β/α-epoxides was determined by $^1$NMR spectroscopy (500 or 300 MHz).
[e]The value in parentheses was the ratio of β/α-epoxides obtained with mCPBA as the oxidant.
[f]In another run, the ratio of β/α-epoxides was >99:1 with acetone and water (3:1) as solvents.

What is claimed is:

1. A method of producing mostly 5β,6β-epoxides of steroids from Δ⁵-unsaturated steroids by an epoxidation reaction using a ketone and an oxidizing agent under conditions effective to generate epoxides, wherein said ketone is selected from compounds of generic formula I,

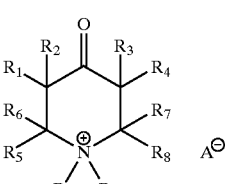

I $R_1$ or $R_4$ in formula (I) is selected from alkyl, halogenated alkyl, aryl, $OR_y$ (where $R_y$=H, alkyl or aryl), $OCOR_y$ (where $R_y$=H, alkyl or aryl), $OCOOR_y$ (where $R_y$=alkyl or aryl), $OCOOCH_2R_z$ (where $R_{z=aryl}$), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_2$ or $R_3$ in formula (I) is selected from H, alkyl, halogenated alkyl, aryl, $OR_y$ (where $R_y$=H, alkyl or aryl), OCOR$_v$ (where R$_v$=H, alkyl or aryl), OCOOR$_y$ (where R$_y$=alkyl or aryl), OCOOCH$_2$R$_z$(where R$_z$=aryl), OCONR$_u$R$_v$(where R$_u$ or R$_v$=H, alkyl or aryl), OSiR$_w$R$_x$R$_y$ (where R$_w$, R$_x$ or R$_y$=alkyl or aryl), and halogen;

R$_5$, R$_6$, R$_7$ or R$_8$ in formula (I) is selected from H, alkyl, halogenated alkyl, aryl, COOR$_v$(where R$_v$=H, alkyl or aryl), and CONR$_u$R$_v$(where R$_u$ or R$_v$=H, alkyl or aryl);

R$_9$ or R$_{10}$ in formula (I) is selected from alkyl, halogenated alkyl, and aryl; and A in formula (I) is selected from halogen, OTf, BF$_4$, OAc, NO$_3$, BPh$_4$, PF$_6$, and SbF$_6$.

2. The method of claim 1 wherein said oxidizing reagent is selected from the group consisting of potassium peroxomonosulfate, sodium hypochlorite, sodium perborate, hydrogen peroxide, and peracids.

3. The method of claim 2 wherein said epoxidation reaction is carried out using potassium peroxomonosulfate as an oxidizing agent.

4. The method of claim 1 wherein said epoxidation reaction is carried out in a homogeneous solvent system selected from dimethoxymethane-acetonitrile-water, acetonitrile-water, acetone-water, dioxane-water, dimethoxyethane-water, and tetrahydrofuran-water, or a biphasic solvent system selected from dichloromethane-water, chloroform-water, benzene-water, toluene-water, dimethoxymethane-water, or diethylether-water, or mixtures thereof.

5. The method of claim 1 wherein said epoxidation reaction is carried out at a temperature within the range from about −10° C. to about 40° C.

6. The method of claim 5 wherein said epoxidation reaction is carried out at room temperature.

7. The method of claim 1 wherein said epoxidation reaction is carried out at a pH within the range from about 7.0 to about 12.0.

8. The method of claim 7 wherein said pH is within the range from about 7.0 to about 7.5.

9. The method of claim 7 wherein said pH is controlled by using a pH-stat or a buffer.

10. The method of claim 9 wherein said buffer is selected from the group consisting of solutions of sodium bicarbonate, sodium carbonate, sodium borate, sodium hydrogenphosphate, sodium dihydrogenphosphate, sodium hydroxide, potassium hydrogenphosphate, potassium dihydrogenphosphate, potassium bicarbonate, potassium carbonate, potassium hydroxide, and mixtures thereof.

11. The method of claim 1 wherein said epoxidation reaction provides said epoxides in at least about 5:1 β/α-epoxide ratio.

12. A method of producing mostly 5β,6β-epoxides of steroids from Δ$^5$-unsaturated steroids having a substituent at the 3α-position by an epoxidation reaction using a ketone and an oxidizing agent under conditions effective to generate epoxides.

13. The method of claim 12 wherein said substituent is selected from OR$_v$(where R$_v$=H, alkyl or aryl), O(CH$_2$)$_n$OR$_v$ (where n=1, 2 or 3, R$_v$=H, alkyl or aryl), O(CH$_2$)$_m$SO$_n$R$_v$ (where m=1, 2 or 3; n=0, 1 or 2; R$_v$=H, alkyl or aryl), OSiR$_w$R$_x$R$_y$(where R$_w$, R$_x$ or R$_y$=alkyl or aryl), OSO$_n$R$_v$ (where n=0, 1 or 2; R$_v$=H, alkyl or aryl), OCO$_n$R$_v$(where n=1 or 2; R$_v$=H, alkyl or aryl), OCONR$_u$R$_v$(where R$_u$ or R$_v$=H, alkyl or aryl), OPO$_n$R$_v$(where n=2 or 3; R$_v$=alkyl or aryl), NR$_u$R$_v$(where R$_u$ or R$_v$=H, alkyl or aryl), NR$_u$CO$_n$R$_v$ (where n=1 or 2; R$_u$ or R$_v$H, alkyl or aryl), NR$_t$CONR$_u$R$_v$ (where R$_t$, R$_u$ or R$_v$=H, alkyl or aryl), NR$_v$SO$_n$R$_y$(where n=1 or 2; R$_v$=H, alkyl or aryl, R$_y$=alkyl or aryl), NPhth (Phth=phthaloyl group), $^+$NR$_t$R$_u$R$_v$(where R$_t$, R$_u$, or R$_v$=H, alkyl or aryl), SiR$_t$R$_u$R$_v$(where R$_t$, R$_u$, or R$_v$=H, alkyl or aryl), SO$_n$R$_v$(where n=0, 1 or 2; R$_v$=H, alkyl or aryl), SCO$_n$R$_v$ (where n=1 or 2; R$_v$=H, alkyl or aryl), halogen, CN, NO$_2$, alkyl, aryl, COOR$_v$(where R$_v$=H, alkyl or aryl), and CONR$_u$R$_v$ (where R$_u$ or R$_v$=H, alkyl or aryl).

14. The method of claim 12 wherein said Δ$^5$-saturated steroid having a substituent at the 3α-position is selected from the group consisting of Δ$^5$-unsaturated steroids having a ketal derivative of ketone group or a thioketal derivative of ketone group at the 3-position.

15. The method of claim 12 wherein said ketone is selected from the group consisting of compounds of generic formula II, III, IV, and V wherein

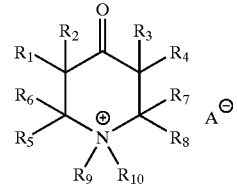

II

R$_1$, R$_2$, R$_3$, or R$_4$ in formula (II) is selected from H, alkyl, halogenated alkyl, aryl, OR$_v$(where R$_v$=H, alkyl or aryl), OCOR$_v$ (where R$_v$=H, alkyl or aryl), OCOOR$_y$ (where R$_y$=alkyl or aryl), OCONR$_u$R$_v$(where R$_u$ or R$_v$=H, alkyl or aryl), OSiR$_w$R$_x$R$_y$ (where R$_w$, R$_x$ or R$_y$=alkyl or aryl), and halogen;

R$_5$, R$_6$, R$_7$, R$_8$, R$_9$ or R$_{10}$ in formula (II) is selected from H, alkyl, halogenated alkyl, aryl, COOR$_v$(where R$_v$=H, alkyl or aryl), and CONR$_u$R$_v$ (where R$_u$ or R$_v$=H, alkyl or aryl);

A in formula (II) is selected from halogen, OTf, BF$_4$, OAc, NO$_3$, BPh$_4$, PF$_6$, and SbF$_6$;

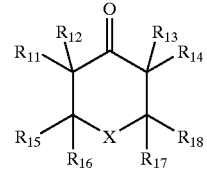

III

X in formula (III) is selected from (CR$_u$R$_v$)$_n$(where n=1, 2, 3, 4, or 5; R$_u$ or R$_v$=H, alkyl or aryl), O, S, SO, SO$_2$, and NR$_v$ (where R$_v$=H, alkyl or aryl);

R$_{11}$, R$_{12}$, R$_{13}$, or R$_{14}$ in formula (III) is selected from H, alkyl, halogenated alkyl, aryl, OR$_v$ (where R$_v$=H, alkyl or aryl), OCOR$_v$ (where R$_v$=H, alkyl or aryl), OCOOR$_y$ (where R$_y$=alkyl or aryl), OCONR$_u$R$_v$ (where R$_u$ or R$_v$=H, alkyl or aryl), OSiR$_w$R$_x$R$_y$ (where R$_w$, R$_x$ or R$_y$=alkyl or aryl), and halogen;

R$_{15}$, R$_{16}$, R$_{17}$, or R$_{18}$ in formula (III) is selected from H, alkyl, halogenated alkyl, aryl, COOR$_v$ (where R$_v$=H, alkyl or aryl), and CONR$_u$R$_v$(where R$_u$ or R$_v$=H, alkyl or aryl);

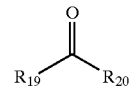

IV

R$_{19}$ or R$_{20}$ in formula (IV) is selected from alkyl, halogenated alkyl, aryl, CR$_t$R$_u$OCOR$_v$ (where R$_t$, R$_u$ or R$_v$=H, alkyl or aryl), CR$_u$R$_v$OCOOR$_y$ (where R$_u$ or R$_v$=H, alkyl or aryl; R$_y$=alkyl or aryl), CR$_t$R$_u$NR$_v$COOR$_y$(where R$_t$, R$_u$ or R$_v$=H, alkyl or aryl, R$_y$=alkyl or aryl), CR$_s$R$_t$NR$_u$COR$_v$ (where R$_s$, R$_t$, R$_u$ or R$_v$=H, alkyl or aryl), and CR$_t$R$_u$NR$_v$SO$_2$R$_y$(where R$_t$, R$_u$ or R$_v$=H, alkyl or aryl; R$_y$=alkyl or aryl); and

33

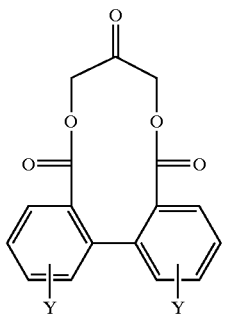

V

Y in formula (V) is selected from H, alkyl, halogenated alkyl, aryl, $NO_2$, CN, F, Cl, Br, I, $COOR_q$ (where $R_q$=H or alkyl), $OR_v$ (where $R_v$=H, alkyl or aryl), $OSO_2R_v$ (where $R_v$=H, alkyl or aryl), $OSR_v$ (where $R_v$=H, alkyl or aryl), $OSR_v$ (where $R_v$=H, alkyl or aryl), $SO_2R_v$ (where $R_v$=H, alkyl or aryl), $SO_3R_v$ (where $R_v$=H, alkyl or aryl), $SOONR_uR_v$ (where $R_u$ or $R_v$=H, alkyl or aryl), $NR_xSOOR_y$ (where $R_v$=H, alkyl or aryl; $R_y$=alkyl or aryl), $NR_xSOR_y$ (where $R_v$=H, alkyl or aryl; $R_y$=alkyl or aryl), $CR_tR_uOR_v$ (where $R_t$, $R_u$ or $R_v$=H, alkyl or aryl), $CR_q(OR_p)_2$ (where $R_q$=H or alkyl; $R_p$=alkyl), $CF_3$, $CF_2CF_3$, OTf, OTs, $OCOR_v$ (where $R_v$=H, alkyl or aryl), and $OSiR_wR_xR_y$ (where $R_w$, $R_x$ or $R_y$=alkyl or aryl).

16. The method of claim 12 wherein said epoxidation reaction is carried out in a homogeneous solvent system selected from dimethoxymethane-acetonitrile-water, acetonitrile-water, acetone-water, dioxane-water, dimethoxymethane-water, and tetrahydrofuran-water, or a biphasic solvent system selected from dichloromethane-water, chloroform-water, benzene-water, toluene-water, dimethoxymethane-water, or diethylether-water, or mixtures thereof.

17. The method of claim 12 wherein said oxidizing reagent is selected from the group consisting of potassium peroxomonosulfate, sodium hypochlorite, sodium perborate, hydrogen peroxide, and peracids.

18. The method of claim 17 wherein said epoxidation reaction is carried out using potassium peroxomonosulfate as an oxidizing agent.

19. The method of claim 12 wherein said epoxidation reaction is carried out at a temperature within the range from about −10° C. to about 40° C.

20. The method of claim 19 wherein said epoxidation reaction is carried out at room temperature.

21. The method of claim 12 wherein said epoxidation reaction is carried out at a pH within the range from about 7.0 to about 12.0.

22. The method of claim 21 wherein said pH is within the range from about 7.0 to about 7.5.

23. The method of claim 21 wherein said pH is controlled by using a pH-stat or a buffer.

24. The method of claim 23 wherein said buffer is selected from the group consisting of solutions of sodium bicarbonate, sodium carbonate, sodium borate, sodium hydrogenphosphate, sodium dihydrogenphosphate, sodium hydroxide, potassium hydrogenphosphate, potassium dihydrogenphosphate, potassium bicarbonate, potassium carbonate, potassium hydroxide, and mixtures thereof.

25. The method of claim 12 wherein said epoxidation reaction provides said epoxides in at least about 5:1 β/α-epoxide ratio.

26. A method of producing mostly 5β,6β-epoxides of steroids from $\Delta^5$-unsaturated steroids by an epoxidation reaction using a dioxirane under conditions effective to generate epoxides,

34 wherein said dioxirane is selected from compounds of generic formula VI,

VI

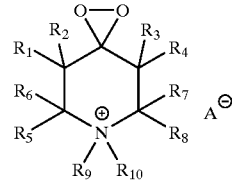

$R_1$ or $R_4$ in formula (VI) is selected from alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2R_z$ (where $R_z$=aryl), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_2$ or $R_3$ in formula (VI) is selected from H, alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2R_z$ (where $R_z$=aryl), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_5$, $R_6$, $R_7$ or $R_8$ in formula (VI) is selected from H, alkyl, halogenated alkyl, aryl, $COOR_v$ (where $R_v$=H, alkyl or aryl), and $CONR_uR_v$ (where $R_u$ or $R_v$=H, alkyl or aryl);

$R_9$ or $R_{10}$ in formula (VI) is selected from alkyl, halogenated alkyl, and aryl; and A in formula (VI) is selected from halogen, OTf, $BF_4$, OAc, $NO_3$, $BPh_4$, $PF_6$, and $SbF_6$.

27. The method of claim 26 wherein said dioxirane is generated in situ from a ketone and an oxidizing agent selected from potassium peroxomonosulfate, sodium hypochlorite, sodium perborate, hydrogen peroxide, and peracids, wherein said ketone is selected from compounds of generic formula I,

I

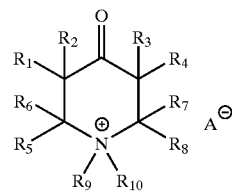

$R_1$ or $R_4$ in formula (I) is selected from alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2R_z$ (where $R_z$=aryl), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_2$ or $R_3$ in formula (I) is selected from H, alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2R$ (where $R_z$=aryl), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_5$, $R_6$, $R_7$ or $R_8$ in formula (I) is selected from H, alkyl, halogenated alkyl, aryl, $COOR_v$ (where $R_v$=H, alkyl or aryl), and $CONR_uR_v$ (where $R_u$ or $R_v$=H, alkyl or aryl);

$R_9$ or $R_{10}$ in formula (I) is selected from alkyl, halogenated alkyl, and aryl; and A in formula (I) is selected from halogen, OTf, $BF_4$, OAc, $NO_3$, $BPh_4$, $PF_6$, and $SbF_6$.

28. The method of claim 26 wherein said epoxidation reaction is carried out in a solvent selected from acetonitrile, dimethoxymethane, acetone, dioxane, dimethoxyethane, tetrahydrofuran, dichloromethane, chloroform, benzene, toluene, diethylether, water, and mixtures thereof.

29. The method of claim 26 wherein said epoxidation reaction is carried out at a temperature within the range from about −40° C. to about 40° C.

30. The method of claim 26 wherein said epoxidation reaction is carried out at a pH within the range from about 7.0 to about 12.0.

31. The method of claim 26 wherein said epoxidation reaction provides said epoxides in at least about 5:1 β/α-epoxide ratio.

32. A method of producing mostly 5β,6β-epoxides of steroids from $\Delta^5$-unsaturated steroids having a substituent at the 3α-position by an epoxidation reaction using a dioxirane under conditions effective to generate epoxides.

33. The method of claim 32 wherein said substituent is selected from $OR_v$ (where $R_v$=H, alkyl or aryl), $O(CH_2)_n OR_v$ (where n=1, 2 or 3, $R_v$=H, alkyl or aryl), $O(CH_2)_m SO_n R_v$ (where m=1, 2 or 3; n=0, 1 or 2; $R_v$=H, alkyl or aryl), $OSiR_w R_x R_y$ (where $R_w$, $R_x$ or $R_y$=alkyl or aryl), $OSO_n R_v$ (where n=0, 1 or 2; $R_v$=H, alkyl or aryl), $OCO_n R_v$ (where n=1 or 2; $R_v$=H, alkyl or aryl), $OCONR_u R_v$ (where $R_u$ or $R_v$=H, alkyl or aryl), $OPO_n R_y$ (where n=2 or 3; $R_y$=alkyl or aryl), $NR_u R_v$ (where $R_u$ or $R_v$=H, alkyl or aryl), $NR_u CO_n R_v$ (where n=1 or 2; $R_u$ or $R_v$=H, alkyl or aryl), $NR_t CONR_u R_v$ (where $R_t$, $R_u$ or $R_v$=H, alkyl or aryl), $NR_y SO_n R_y$ (where n=1 or 2; $R_v$=H, alkyl or aryl, $R_y$=alkyl or aryl), NPhth (Phth=phthaloyl group), $^{+NR_t}R_u R_v$ (where $R_t$, $R_u$, or $R_v$=H, alkyl or aryl), $SiR_t R_u R_v$ (where $R_t$, $R_u$, or $R_v$=H, alkyl or aryl), $SO_n R_v$ (where n=0, 1 or 2; $R_v$=H, alkyl or aryl), $SCO_n R_v$ (where n=1 or 2; $R_v$=H, alkyl or aryl), halogen, CN, $NO_2$, alkyl, aryl, $COOR_v$ (where $R_v$=H, alkyl or aryl), and $CONR_u R_v$ (where $R_u$ or $R_v$=H, alkyl or aryl).

34. The method of claim 32 wherein said $\Delta^5$-unsaturated steroid having a substituent at the 3α-position is selected from the group consisting of $\Delta^5$-unsaturated steroids having a ketal derivative of ketone group or a thioketal derivative of ketone group at the 3-position.

35. The method of claim 32 wherein said dioxirane is selected from the group consisting of compounds of generic formula VII, VIII, IX and X, wherein

VII

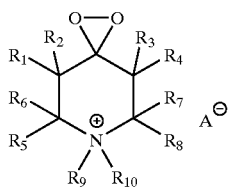

$R_1$, $R_2$, $R_3$, or $R_4$ in formula (VII) is selected from H, alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2 R_z$ (where $R_z$=aryl), $OCONR_u R_v$ (where $R_u$ or $R_v$=H, alkyl or aryl), $OSiR_w R_x R_y$ (where $R_w$, $R_x$ or $R_y$=alkyl or aryl), and halogen;

$R_5$, $R_6$, $R_7$, $R_8$, $R_9$ or $R_{10}$, in formula (VII) is selected from H, alkyl, halogenated alkyl, aryl, $COOR_v$ (where $R_v$=H, alkyl or aryl), and $CONR_u R_v$ (where $R_u$ or $R_v$=H, alkyl or aryl);

A in formula (VII) is selected from halogen, OTf, $BF_4$, OAc, $NO_3$, $BPh_4$, $PF_6$, and $SbF_6$;

VIII

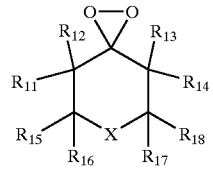

X in formula (VIII) is selected from $(CR_u R_v)_n$ (where n=1, 2, 3, 4, or 5; $R_u$ or $R_v$=H, alkyl or aryl), O, S, SO, $SO_2$, and $NR_v$ (where $R_v$=H, alkyl or aryl);

$R_{11}$, $R_{12}$, $R_{13}$, or $R_{14}$ in formula (VIII) is selected from H, alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2 R_z$ (where $R_z$=aryl), $OCONR_u R_v$ (where $R_u$ or $R_v$=H, alkyl or aryl), $OSiR_w R_x R_y$ (where $R_w$, $R_x$ or $R_y$=alkyl or aryl), and halogen;

$R_{15}$, $R_{16}$, $R_{17}$, or $R_{18}$ in formula (VIII) is selected from H, alkyl, halogenated alkyl, aryl, $COOR_v$ (where $R_v$=H, alkyl or aryl), and $CONR_u R_v$ (where $R_u$ or $R_v$=H, alkyl or aryl);

IX

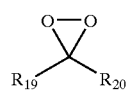

$R_{19}$ or $R_{20}$ in formula (IX) is selected from alkyl, halogenated alkyl, aryl, $CR_t R_u OCOR_v$ (where $R_t$, $R_u$ or $R_v$=H, alkyl or aryl), $CR_u R_v OCOOR_y$ (where $R_u$ or $R_v$=H, alkyl or aryl; $R_y$=alkyl or aryl), $CR_t R_u NR_v COOR_y$ (where $R_t$, $R_u$ or $R_v$=H, alkyl or aryl, $R_y$=alkyl or aryl), $CR_s R_t NR_u COR_v$ (where $R_s$, $R_t$, $R_u$ or $R_v$=H, alkyl or aryl), $CR_t R_u NR_v SO_2 R_y$ (where $R_t$, $R_u$ or $R_v$=H, alkyl or aryl; $R_y$=alkyl or aryl); and

X

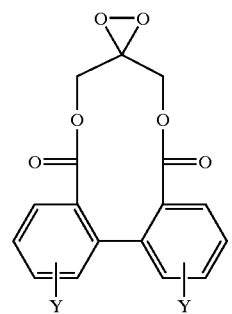

Y in formula (X) is selected from H, alkyl, halogenated alkyl, aryl, $NO_2$, CN, F, Cl, Br, I, $COOR_q$ (where $R_q$=H or alkyl), $OR_v$ (where $R_v$=H, alkyl or aryl), $OSO_2 R_v$ (where $R_v$=H, alkyl or aryl), $OSOR_v$ (where $R_v$=H, alkyl or aryl), $OSR_v$ (where $R_v$=H, alkyl or aryl), $SO_2 R_v$ (where $R_v$=H, alkyl or aryl), $SO_3 R_v$ (where $R_v$=H, alkyl or aryl), $SOONR_u R_v$ (where $R_u$ or $R_v$=H, alkyl or aryl), $NR_v SOOR_y$ (where $R_v$=H, alkyl or aryl; $R_y$=alkyl or aryl), $NR_v SOR_y$ (where $R_v$=H, alkyl or aryl; $R_y$=alkyl or aryl), $CR_t R_u OR_v$ (where $R_t$, $R_u$ or $R_v$=H, alkyl or aryl), $CR_q(OR_p)_2$ (where $R_q$=H or alkyl; $R_p$=alkyl), $CF_3$, $CF_2 CF_3$, OTf, OTs, $OCOR_v$ (where $R_v$=H, alkyl or aryl), and $OSiR_w R_x R_y$ (where $R_w$, $R_x$ or $R_y$=alkyl or aryl).

36. The method of claim 32 wherein said dioxirane is generated in situ from a ketone and an oxidizing agent selected from potassium peroxomonosulfate, sodium hypochlorite, sodium perborate, hydrogen peroxide, and peracids.

37. The method of claim 36 wherein said ketone is selected from the group consisting of compounds of generic formula II, III, IV, and V,

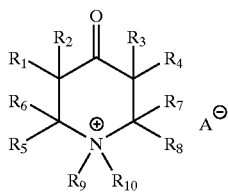

II $R_1, R_2, R_3,$ or $R_4$ in formula (II) is selected from H, alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2R_z$ (where $R_z$=aryl), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_5, R_6, R_7, R_8, R_9$ or $R_{10}$ in formula (II) is selected from H, alkyl, halogenated alkyl, aryl, $COOR_v$ (where $R_v$=H, alkyl or aryl), and $CONR_uR_v$ (where $R_u$ or $R_v$=H, alkyl or aryl);

A in formula (II) is selected from halogen, OTf, $BF_4$, OAc, $NO_3$, $BPh_4$, $PF_6$, and $SbF_6$;

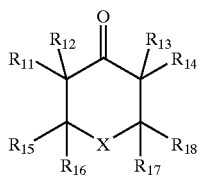

III

X in formula (III) is selected from $(CR_uR_v)_n$ (where n=1, 2, 3, 4, or 5; $R_u$ or $R_v$=H, alkyl or aryl), O, S, SO, $SO_2$, and $NR_v$ (where $R_v$=H, alkyl or aryl);

$R_{11}, R_{12}, R_{13},$ or $R_{14}$ in formula (III) is selected from H, alkyl, halogenated alkyl, aryl, $OR_v$ (where $R_v$=H, alkyl or aryl), $OCOR_v$ (where $R_v$=H, alkyl or aryl), $OCOOR_y$ (where $R_y$=alkyl or aryl), $OCOOCH_2R_z$ (where $R_z$=aryl), $OCONR_uR_v$ (where $R_u$ or $R_v$=H, alkyl or aryl), $OSiR_wR_xR_y$ (where $R_w$, $R_x$ or $R_y$=alkyl or aryl), and halogen;

$R_{15}, R_{16}, R_{17},$ or $R_{18}$ in formula (III) is selected from H, alkyl, halogenated alkyl, aryl, $COOR_v$ (where $R_v$=H, alkyl or aryl), and $CONR_uR_v$ (where $R_u$ or $R_v$=H, alkyl or aryl);

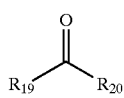

IV $R_{19}$ or $R_{20}$ in formula (IV) is selected from alkyl, halogenated alkyl, aryl, $CR_tR_uOCOR_v$ (where $R_t$, $R_u$ or $R_v$=H, alkyl or aryl), $CR_uR_vOCOOR_y$ (where $R_u$ or $R_v$=H, alkyl or aryl; $R_y$=alkyl or aryl), $CR_tR_uNR_v$-$COOR_y$ (where $R_t$, $R_u$ or $R_v$=H, alkyl or aryl, $R_y$=alkyl or aryl), $CR_sR_tNR_uCOR_v$ (where $R_s$, $R_t$, $R_u$ or $R_v$=H, alkyl or aryl), $CR_tR_uNR_vSO_2R_y$ (where $R_t$, $R_u$ or $R_v$=H, alkyl or aryl; $R_y$=alkyl or aryl); and

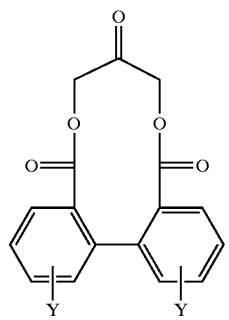

V

Y in formula (V) is selected from H, alkyl, halogenated alkyl, aryl, $NO_2$, CN, F, Cl, Br, I, $COOR_q$ (where $R_q$=H or alkyl), $OR_v$ (where $R_v$=H, alkyl or aryl), $OSO_2R_v$ (where $R_v$=H, alkyl or aryl), $OSOR_v$ (where $R_v$=H, alkyl or aryl), $OSR_v$ (where $R_v$=H, alkyl or aryl), $SO_2R_v$ (where $R_v$=H, alkyl or aryl), $SO_3R_v$ (where $R_v$=H, alkyl or aryl), $SOON R_uR_v$ (where $R_u$ or $R_v$=H, alkyl or aryl), $NR_vSOOR_y$ (where $R_v$=H, alkyl or aryl; $R_y$=alkyl or aryl), $NR_vSOR_y$ (where $R_v$=H, alkyl or aryl; $R_y$=alkyl or aryl), $CR_tR_uOR_v$ (where $R_t$, $R_u$ or $R_v$=H, alkyl or aryl), $CR_q(OR_p)_2$ (where $R_q$=H or alkyl; $R_p$=alkyl), $CF_3$, $CF_2CF_3$, OTf, OTs, $OCOR_v$ (where $R_v$=H, alkyl or aryl), and $OSiR_wR_xR_y$ (where $R_w$, $R_x$ or $R_y$=alkyl or aryl).

38. The method of claim 32 wherein said epoxidation reaction is carried out in a solvent selected from acetonitrile, dimethoxymethane, acetone, dioxane, dimethoxyethane, tetrahydrofuran, dichloromethane, chloroform, benzene, toluene, diethylether, water and mixtures thereof.

39. The method of claim 32 wherein said epoxidation reaction is carried out at a temperature within the range from about −40° C. to about 40° C.

40. The method of claim 32 wherein said epoxidation reaction is carried out at a pH within the range from about 7.0 to about 12.0.

41. The method of claim 32 wherein said epoxidation reaction provides said epoxides in at least about 5:1 β/α-epoxide ratio.

42. A method comprising:
producing mostly 5β,6β-epoxides of steroids by epoxidation reactions of $\Delta^5$-unsaturated steroids of generic formula XI catalyzed by ketones of generic formula XII, wherein

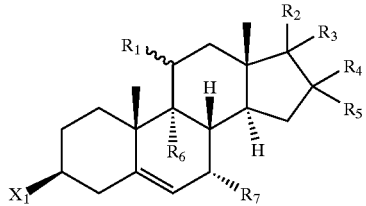

XI $X_1$ in formula (XI) is selected from H, $OR_q$ (where $R_q$=H or alkyl), $OCH_2OCH_3$, $OCOR_v$ (where $R_y$=alkyl or aryl), $OSiR_wR_xR_y$ (where $R_w$, $R_x$ or $R_y$=alkyl or aryl), halogen, CN, alkyl, aryl, and $COOR_v$ (where $R_v$=H, alkyl or aryl);

$R_1$ in formula (XI) is selected from H, $OR_q$ (where $R_q$=H or alkyl), $OCOR_y$ (where $R_y$=alkyl or aryl), $OCH_2OCH_3$, halogen, $CF_3$, and $CF_2CF_3$;

$R_2$ and $R_3$ in formula (XI) are each selected from the group consisting of H, alkyl, aryl, halogen, $OR_q$ (where $R_q$=H or alkyl), $OCOR_y$ (where $R_y$=alkyl or aryl), $OSiR_wR_xR_y$ (where $R_w$, $R_x$ or $R_y$=alkyl or aryl), $COR_p$ (where $R_p$=alkyl), $COCH_2OR_q$ (where $R_q$=H or alkyl), $COCH_2OCOR_y$ (where $R_y$=alkyl or aryl), $COCH_2F$, $COOR_q$ (where $R_q$=H or alkyl), $C(OCH_2CH_2O)R_p$ (where $R_p$=alkyl), $C(OCH_2CH_2O)CH_2OR_q$ (where $R_q$=H or alkyl), $C(OCH_2CH_2O)CH_2OCOR_y$ (where $R_y$=alkyl or aryl), and $C(OCH_2CH_2O)CH_2F$; or, are selected from the group consisting of O, $OCH_2CH_2O$, and $OCH_2CH_2CH_2O$;

$R_4$ in formula (XI) is selected from H, $C_1$–$C_4$ alkyl, halogen, $OR_q$ (where $R_q$=H or alkyl), $OCOR_y$ (where $R_y$=alkyl or aryl), and $OSiR_w$, $R_x$ $R_y$ (where $R_w$, $R_x$ or $R_y$=alkyl or aryl);

$R_5$ in formula (XI) is selected from H, $C_1$–$C_4$ alkyl, halogen, $OR_q$ (where $R_q$=H or alkyl), $OCOR_y$ (where $R_y$=alkyl or aryl), and $OSiR_wR_xR_y$ (where $R_w$, $R_x$ or $R_y$=alkyl or aryl);

$R_6$ in formula (XI) is selected from H, halogen, $OR_q$ (where $R_q$=H or alkyl), and $OCOR_y$ (where $R_y$=alkyl or aryl);

$R_7$ in formula (XI) is selected from H, halogen, $OR_q$ (where $R_q$=H or alkyl), and $OCOR_y$ (where $R_y$=alkyl or aryl);

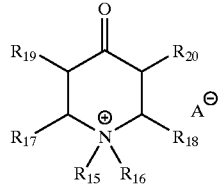
XII $R_{15}$ and $R_{16}$ in formula (XII) are each selected from alkyl and aryl;

$R_{17}$ and $R_{18}$ in formula (XII) are each selected from H, alkyl, aryl, $COOR_y$ (where $R_y$=H, alkyl or aryl), and $CONR_uR^v$ (where $R_u$ or $R_v$=H, alkyl or aryl);

$R_{19}$ and $R_{20}$ in formula (XII) are each selected from $C_1$–$C_4$ alkyl, halogenated alkyl, and halogen; and A in formula (XII) is selected from OTf, $BF_4$, OAc, $NO_3$, $BPh_4$, $PF_6$, and $SbF_6$.

43. The method of claim 42 wherein said $C_1$–$C_4$ alkyl is selected from the group consisting of methyl, ethyl, normal-propyl, iso-propyl, normal-butyl, iso-butyl, sec-butyl, and tert-butyl; and said aryl is selected from the group consisting of phenyl, substituted phenyl, naphthyl, and substituted naphthyl groups.

44. The method of claim 42 wherein said epoxidation reactions are carried out in a homogeneous solvent system selected from the group consisting of dimethoxymethane-acetonitrile-water, acetonitrile-water, acetone-water, dioxane-water, dimethoxyethane-water, tetrahydrofuran-water, and mixtures thereof.

45. The method of claim 42 wherein said epoxidation reactions are carried out in a biphasic solvent system selected from the group consisting of dichloromethane-water, chloroform-water, benzene-water, toluene-water, dimethoxymethane-water, and diethylether-water, and mixtures thereof.

46. The method of claim 42 wherein said oxidizing reagent is selected from the group consisting of potassium peroxomonosulfate, sodium hypochlorite, sodium perborate, hydrogen peroxide, and peracids.

47. The method of claim 42 wherein said epoxidation reactions are carried out at a temperature within the range from about –10° C. to about 40° C.

48. The method of claim 47 wherein said epoxidation reactions are carried out at room temperature.

49. The method of claim 42 wherein said epoxidation reactions are carried out at a pH within the range from about 7.0 to about 12.0.

50. The method of claim 49 wherein said pH is within the range from 7.0 to 7.5.

51. The method of claim 49 wherein said pH is controlled by using a pH-stat or a buffer.

52. The method of claim 51 wherein said buffer is selected from the group consisting of sodium bicarbonate, sodium carbonate, sodium borate, sodium hydrogenphosphate, sodium dihydrogenphosphate, sodium hydroxide, potassium hydrogenphosphate, potassium dihydrogenphosphate, potassium bicarbonate, potassium carbonate, potassium hydroxide, and mixtures thereof.

53. A method comprising:
producing mostly 5β,6β-epoxides of steroids by epoxidation reactions of Δ$^5$-unsaturated steroids of generic formula XIII catalyzed by ketones of generic formula XIV, XV, XVI, and XVII, wherein

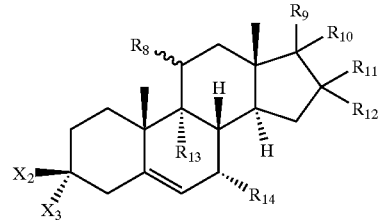
XIII $X_2$ in formula (XIII) is selected from the group consisting of H, $OR_q$ (where $R_q$=H or alkyl), $OCH_2OCH_3$, $OCOR_y$ (where $R_y$=alkyl or aryl), $OSiR_wR_xR_y$ (where $R_w$, $R_x$ or $R_y$=alkyl or aryl), halogen, CN, alkyl, aryl, and $COOR_y$ (where $R_y$=H, alkyl or aryl), and, $X_3$ in formula (XIII) is selected from the group consisting of $OR_q$ (where $R_q$=H or alkyl), $OCH_2OOH_3$, $OCOR_y$ (where $R_y$=alkyl or aryl), $OSiR_wR_xR_y$ (where $R_w$, $R_x$ or $R_y$=alkyl or aryl), halogen, CN, $NO_2$, alkyl, and aryl; or, $X_2$ and $X_3$ in formula (XIII) are selected from the group consisting of O, $OCH_2CH_2O$, and $OCH_2CH_2CH_2O$;

$R_8$ in formula (XIII) is selected from H, $OR_q$ (where $R_q$=H or alkyl), $OCOR_y$ (where $R_y$=alkyl or aryl), $OCH_2OCH_3$, halogen, $CF_3$, and $CF_2CF_3$;

$R_9$ and $R_{10}$ in formula (XIII) are each selected from the group consisting of H, alkyl, aryl, halogen, $OR_q$ (where $R_q$=H or alkyl), $OCOR_y$ (where $R_y$=alkyl or aryl), $OSiR_wR_xR_y$ (where $R_w$, $R_x$ or $R_y$=alkyl or aryl), $COR_p$ (where $R_p$=alkyl), $COCH_2OR_q$ (where $R_q$ H or alkyl), $COOH_2OCOR_y$ (where $R_y$=alkyl or aryl), $COOH_2F$, $COOR_q$ (where $R_q$=H or alkyl), $C(OCH_2CH_2O)R_p$ (where $R_p$=alkyl), $C(OCH_2CH_2O)CH_2OR_q$ (where $R_q$=H or alkyl), $C(OCH_2CH_2O)CH_2OCOR_y$ (where $R_y$=alkyl or aryl), and $C(OCH_2CH_2O)CH_2F$; or $R_9$ and $R_{10}$ in formula (XIII) are selected from the group consisting of O, $OCH_2CH_2O$, and $OCH_2CH_2CH_2O$;

$R_{11}$ and $R_{12}$ in formula (XIII) are each selected from the group consisting of H, $C_1$–$C_4$ alkyl, halogen, $OR_q$ (where $R_q$=H or alkyl), $OCOR_y$ (where $R_y$=alkyl or aryl), and $OSiR_wR_xR_y$ (where $R_w$, $R_x$ or $R_y$=alkyl or aryl);

$R_{13}$ and $R_{14}$ in formula (XIII) are each selected from the group consisting of H, halogen, $OR_q$ (where $R_q$=H or alkyl), and $OCOR_y$ (where $R_y$=alkyl or aryl);

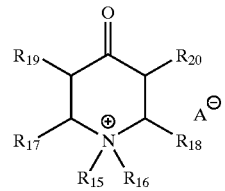
XIV $R_{15}$ or $R_{16}$ in formula (XIV) is selected from alkyl and aryl;

$R_{17}$ or $R_{18}$ in formula (XIV) is selected from H, alkyl, aryl, $COOR_y$ (where $R_y$=H, alkyl or aryl), and $CONR_uR_v$ (where $R_u$ or $R_v$=H, alkyl or aryl);

$R_{19}$ or $R_{20}$ in formula (XIV) is selected from H, $C_1$–$C_4$ alkyl, halogenated alkyl, and halogen; and A in formula (XIV) is selected from OTf, $BF_4$, OAc, $NO_3$, $BPh_4$, $PF_6$, and $SbF_6$;

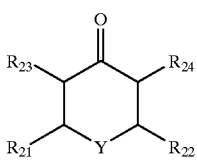

XV

Y in formula (XV) is selected from $CH_2$, O, S, SO, $SO_2$, and $NR_q$ (where $R_q$=H or alkyl);

$R_{21}$ or $R_{22}$ in formula (XV) is selected from H, alkyl, aryl, $COOR_v$ (where $R_v$=H, alkyl or aryl), and $CONR''R^v$ (where $R_u$ or $R_v$=H, alkyl or aryl);

$R_{23}$ or $R_{24}$ in formula (XV) is selected from H, halogen, $C_1$–$C_4$ alkyl, halogenated alkyl, and $OCOR_y$ (where $R_y$=alkyl or aryl);

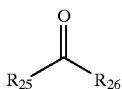

XVI $R_{25}$ or $R_{26}$ in formula (XVI) is selected from $C_1$–$C_4$ alkyl, halogenated alkyl, $CH_2OCOR_y$ (where $R_y$=alkyl or aryl); and

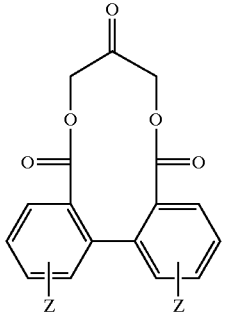

XVII

Z in formula (XVII) is selected from H, $C_1$–$C_4$ alkyl, aryl, $NO_2$, CN, F, Cl, Br, I, $COOR_p$ (where $R_p$=alkyl), $CH_2OR_q$ (where $R_q$=H or alkyl), $CH(OR_p)_2$ (where $R_p$=alkyl), $CF_3$, $CF_2CF_3$, OTf, OTs, $OCOR_y$ (where $R_y$=alkyl or aryl), and $OSiR_wR_xR_y$ (where $R_w$, $R_x$ or $R_y$=alkyl or aryl).

54. The method of claim 53 wherein said $C_1$–$C_4$ alkyl is selected from the group consisting of methyl, ethyl, normal-propyl, iso-propyl, normal-butyl, iso-butyl, sec-butyl, and tert-butyl; and said aryl is selected from the group consisting of phenyl, substituted phenyl, naphthyl, and substituted naphthyl groups.

55. The method of claim 53 wherein said epoxidation reactions are carried out in a homogeneous solvent system selected from the group consisting of dimethoxymethane-acetonitrile-water, acetonitrile-water, acetone-water, dioxane-water, dimethoxyethane-water, and tetrahydrofuran-water, and mixtures thereof.

56. The method of claim 53 wherein said epoxidation reactions are carried out in a biphasic solvent system selected from the group consisting of dichloromethane-water, chloroform-water, benzene-water, toluene-water, dimethoxymethane-water, and diethylether-water, and mixtures thereof.

57. The method of claim 53 wherein said oxidizing reagent is selected from the group consisting of potassium peroxomonosulfate, sodium hypochlorite, sodium perborate, hydrogen peroxide, and peracids.

58. The method of claim 53 wherein said epoxidation reactions are carried out at a temperature within the range from about –10° C. to about 40° C.

59. The method of claim 58 wherein said epoxidation reactions are carried out at room temperature.

60. The method of claim 53 wherein said epoxidation reactions are carried out at a pH within the range from about 7.0 to about 12.0.

61. The method of claim 60 wherein said pH is within the range from 7.0 to 7.5.

62. The method of claim 60 wherein said pH is controlled by using a pH-stat or a buffer.

63. The method of claim 62 wherein said buffer is selected from the group consisting of sodium bicarbonate, sodium carbonate, sodium borate, sodium hydrogenphosphate, sodium dihydrogenphosphate, sodium hydroxide, potassium hydrogenphosphate, potassium dihydrogenphosphate, potassium bicarbonate, potassium carbonate, potassium hydroxide, and mixtures thereof.

\* \* \* \* \*

UNITED STATES PATENT AND TRADEMARK OFFICE
CERTIFICATE OF CORRECTION

PATENT NO. : 6,841,665 B2
DATED : January 11, 2005
INVENTOR(S) : Yang et al.

It is certified that error appears in the above-identified patent and that said Letters Patent is hereby corrected as shown below:

<u>Column 30,</u>
Line 63, delete "$_{oconru}R_v$" and insert -- $OCONR_u$ --.

<u>Column 31,</u>
Line 61, delete "RvH," and insert -- Rv=H, --.
Line 61, delete $NR_1CONR_uR_v$" and insert -- $NR_1CONR_uR_v$ --.

<u>Column 32,</u>
Line 3, delete "$\Delta^5$-saturated" and insert -- $\Delta^5$-unsaturated --.
Line 24, delete "$R_{w1}Rx$" and insert -- Rw Signed and Sealed this Tenth Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,841,665 B2
DATED : January 11, 2005
INVENTOR(S) : Yang et al.

It is certified that error appears in the above-identified patent and that said Letters Patent is hereby corrected as shown below:

Column 30,
Line 63, delete "$_{OCONR_uR_v}$" and insert -- $OCONR_u$ --.

Column 31,
Line 61, delete "$R_vH$," and insert -- $R_v=H$, --.
Line 61, delete "$NR_1CONR_uR_v$" and insert -- $NR_lCONR_uR_v$ --.

Column 32,
Line 3, delete "$\Delta^5$-saturated" and insert -- $\Delta^5$-unsaturated --.
Line 24, delete "$R_w,R_x$" and insert -- $R_w, R_x$ --.

Column 33,
Line 18, delete "$OSR_v$" and insert -- $OSOR_v$ --.

Column 35,
Line 30, delete "$^{+NR}{}_tR_uR_v$" and insert -- $^+NR_tR_uR_v$ --.

Column 39,
Line 19, delete "$CONR_uR^v$" and insert -- $CONR_uR_v$ --.

Column 41,
Line 12, delete "$R^uR^v$" and insert -- $R_uR_v$ --.

Signed and Sealed this

Fourteenth Day of June, 2005

JON W. DUDAS
*Director of the United States Patent and Trademark Office*